US008012466B2

(12) United States Patent
Morita et al.

(10) Patent No.: US 8,012,466 B2
(45) Date of Patent: Sep. 6, 2011

(54) IMMUNOGENIC COMPOSITIONS FOR ACTIVATING γδ T CELLS

(75) Inventors: Craig T. Morita, Iowa City, IA (US); Bradley D. Jones, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 237 days.

(21) Appl. No.: 12/362,968

(22) Filed: Jan. 30, 2009

(65) Prior Publication Data
US 2009/0196887 A1 Aug. 6, 2009

Related U.S. Application Data

(60) Provisional application No. 61/025,145, filed on Jan. 31, 2008.

(51) Int. Cl.
*A01N 63/00* (2006.01)
*A01N 65/00* (2006.01)
(52) U.S. Cl. ............... 424/93.1; 424/93.2; 424/93.4
(58) Field of Classification Search .................. None
See application file for complete search history.

(56) References Cited

U.S. PATENT DOCUMENTS

| 2006/0079487 A1 | 4/2006 | Sanders et al. | |
|---|---|---|---|
| 2007/0025960 A1 | 2/2007 | Pauza et al. | |
| 2008/0241268 A1* | 10/2008 | Gaiger et al. | 424/499 |
| 2010/0297187 A1* | 11/2010 | Stoloff et al. | 424/272.1 |

FOREIGN PATENT DOCUMENTS

| CA | 2 444 955 A1 | 11/2002 |
|---|---|---|
| WO | 02083720 | 10/2002 |
| WO | 02/095011 A3 | 11/2002 |
| WO | 2004/050096 A2 | 6/2004 |
| WO | 2006/017954 A1 | 2/2006 |
| WO | 2006/103568 A2 | 10/2006 |
| WO | 2007/028047 A2 | 3/2007 |
| WO | 2007/028047 A3 | 3/2007 |

OTHER PUBLICATIONS

Plotkin et al (Vaccines W. B. Saunders Company, 1988, p. 571).*
Altincicek, Boran et al, "LytB, a Novel Gene of the 2-C-methyl-D-erythritol 4-phosphate Pathway of Isoprenoid Biosynthesis in *Escherichia coli*", FEBS Letters 499 (2001) pp. 37-40.
Altincicek, Boran et al, "Cutting Edge: Human Gamma Delta T Cells Are Activated by Intermediates of the 2-C-methyl-D-erythritol 4-phosphate Pathway of Isoprenoid Biosynthesis", The Journal of Immunology, pp. 3655-3658; published at least as early as Dec. 31, 2001.
Hintz, Martin et al, "Identification of (E)-4-hydroxy-3-methyl-but-2-enyl pyrophosphate as a Major Activator for Human Gamma Delta T Cells in *Escherichia coli*", FEBS Letters 509 (2001) pp. 317-322.
Eberl, Matthias et al, "Accumulation of a Potent Gamma Delta T-Cell Stimulator After Deletion of the lytB Gene in *Escherichia coli*", Immunology (2002) 106, pp. 200-211.
Poquet, Yannick et al, "Expansion of VGamma9VDelta2 T Cells Is Triggered by *Francisella tularensis*-Derived Phosphoantigens in Tularemia but Not After Tularemia Vaccination", Infection and Immunity, May 1998, vol. 66, No. 5, pp. 2107-2114.
Shin, Sung Jae et al, "Identification of Novel Virulence Determinants in *Mycobacterium paratuberculosis* by Screening a Library of Insertional Mutants", Infection and Immunity, Jul. 2006, vol. 74, No. 7, pp. 3825-3833.
Morita, Craig T. et al, "Nonpeptide Antigens, Presentation Mechanisms, and Immunological Memory of Human VGamma2VDelta2 T Cells: Discriminating Friend from Foe Through the Recognition of Prenyl Pyrophosphate Antigens", Immunological Reviews, 2007, vol. 215, pp. 57-76.
Dieli, Francesco et al, "Targeting Human Gamma Delta T Cells with Zoledronate and Interleukin-2 for Immunotherapy of Hormone-Refractory Prostate Cancer", Cancer Research, 2007, 67: (15), Aug. 1, 2007, pp. 7450-7457, including Supplementary Material pp. 1-6.
Wilhelm, Martin et al, "Gamma Delta T Cells for Immune Therapy of Patients with Lymphoid Malignancies", Immunobiology, Blood, Jul. 1, 2003, vol. 102, No. 1, pp. 200-206.
Berndt, Angela et al, "Circulating Gamma Delta T Cells in Response to *Salmonella enterica* Serovar Enteritidis Exposure in Chickens", Infection and Immunology, Jul. 2006, vol. 74, No. 7, pp. 3967-3978.
Puan, Kia-Joo et al, "Preferential Recognition of a Microbial Metabolite by Human VGamma2VDelta2 T Cells", International Immunology, 2007, vol. 19, No. 5, pp. 657-673.
Begley, M., et al., "The interplay between classical and alternative isoprenoid biosynthesis controls gammadelta T cell bioactivity of *Listeria monocytogenes*," FEBS Letters, vol. 561, pp. 99-104, 2004.
Begley, M., et al., "Analysis of the isoprenoid biosynthesis pathways in *Listeria monocytogenes* reveals a role for the alternative 2-C-methl-D-erythritol 4-phosphate pathway in murine infection", Infection and Immunity, vol. 76, No. 11, pp. 5392-5401, Nov. 2008.
Eberl, M., et al., "Microbial isoprenoid biosynthesis and human gammadelta T cell activation", FEBS Letters, vol. 544, pp. 4-10, 2003.
International Search Report for PCT/US2009/032581 dated Nov. 20, 2009.
Chen, Zheng W. and Letvin, Norman L., "Vgamma2Vdelta2+ T Cells and Anti-Microbial Immune Responses", Microbes and Infection 5 (2003) 491-498.

* cited by examiner

*Primary Examiner* — Albert Navarro
(74) *Attorney, Agent, or Firm* — Andrus, Sceales, Starke & Sawall, LLP

(57) ABSTRACT

Disclosed are compositions, kits, and methods for activating, expanding, or stimulating γδ T cells that include recombinant attenuated microbes. The compositions may include pharmaceutical compositions that are used as γδ T cell stimulating immunogenic compositions.

26 Claims, 26 Drawing Sheets

| MEASURED MASS | CALCULATED MASS | COMPOSITION | ERROR (ppm) |
|---|---|---|---|
| 260.993655 | 260.993468 | C5H11O8P2 | +0.72 |
| | 260.995836 | C12H6O5P1 | −8.35 |
| | 260.992237 | C9H13O3P4 | +5.43 |

# IMMUNOGENIC COMPOSITIONS FOR ACTIVATING γδ T CELLS

CROSS-REFERENCE TO RELATED APPLICATIONS

The present application claims the benefit of priority under 35 U.S.C. §119(e) to U.S. Provisional Patent Application No. 61/025,145, filed on Jan. 31, 2008, the content of which is incorporated by reference herein in its entirety.

STATEMENT REGARDING RESEARCH OR DEVELOPMENT SPONSORED BY THE U.S. GOVERNMENT

This invention was made with U.S. government support under grant no. RO1 AR45504 from the National Institute of Arthritis and Musculoskeletal and Skin Disease, and grant no. U54 AI057160 from the National Institute of Allergy and Infectious Diseases. The U.S. government has certain rights in the invention.

BACKGROUND

The present invention relates generally to the field of compositions, kits, and methods for activating, expanding, or stimulating T cells. In particular, the present invention relates to pharmaceutical compositions that may be useful as vaccines or immunogenic compositions for activating, expanding, or stimulating γδ T cells.

Human γδ T cells, such as Vγ2Vδ2 T cells, are stimulated by prenyl pyrophosphates, such as isopentenyl pyrophosphate (IPP), and play important roles in mediating immunity against microbial pathogens and have potent anti-tumor activity. (E)-4-hydroxy-3-methyl-but-2-enyl pyrophosphate (HMBPP) has been identified as a metabolite in the 2-C-methyl-D-erythritol-4 phosphate (MEP) pathway for isoprenoid biosynthesis that is used by many bacteria and protozoan parasites. Here, it is found that HMBPP is the major Vγ2Vδ2 T cell antigen for many bacteria, including *Mycobacterium tuberculosis, Yersinia enterocolitica*, and *Escherichia coli*. HMBPP was a 30,000-fold more potent antigen than IPP. Using mutant bacteria, it is shown that bacterial antigen levels for Vγ2Vδ2 T cells are controlled by MEP pathway enzymes and no evidence for the production of 3-formyl-1-butyl pyrophosphate was found. Moreover, HMBPP-reactivity required only germ-line encoded Vγ2Vδ2 TCR elements and is present at birth. Bacterial HMBPP levels were shown to correlate with an ability to expand Vγ2Vδ2 T cells in vivo upon engraftment into severe combined immunodeficiency-beige (SCID-beige) mice. Thus, the production of HMBPP by a microbial-specific isoprenoid pathway plays a major role in determining whether bacteria will stimulate Vγ2Vδ2 T cells in vivo. This preferential stimulation by a common microbial isoprenoid metabolite may allow Vγ2Vδ2 T cells to respond to a broad array of pathogens using this pathway.

Another synthetic phosphoantigen, bromohydrin pyrophosphate (BrHPP)/Phosphostim, was found to transiently expand Vγ9/Vδ2 in cynomolgus monkeys, which were used as a non-human primate model. (See Sicard et al. In Vivo Immonmanipulation of Vγ9Vδ2 T cells with a Synthetic Phosphoantigen in a Preclincal Nonhuman Primate Model. J. Immunol. 2005, 175: 5471-5480). However, this transient expansion was found to return to baseline within 10-15 days. Furthermore, succession infusions of BrHPP induced less vigorous expansions, suggesting that progressive exhaustion of the response was occurring. Therefore, vaccines and immunogenic compositions that induce more long-lasting expansions of γδ T cells and that do not result in exhaustion are desirable.

SUMMARY

Disclosed are pharmaceutical compositions, kits, and methods for inducing an immunogenic response. The pharmaceutical compositions may be useful as vaccines or immunogenic compositions for activating, expanding, or stimulating γδ T cells.

The disclosed compositions include vaccines or immunogenic compositions comprising: (a) an effective amount of a recombinant attenuated microbe for activating, expanding, or stimulating γδ T cells in a subject, wherein the microbe comprises a mutation in lytB and the microbe comprises one or more heterologous genes for production of mevalonate; (b) an excipient, carrier, or diluent; and optionally (c) an adjuvant. Microbes may include bacteria (e.g., selected from a group consisting of *Salmonella* spp., *Listeria* spp., *Shigella* spp., *Yersinia* spp, and *Escherichia* spp.) and protozoa. In further embodiments, the recombinant attenuated microbe is a strain of *Salmonella enterica* (e.g., *Salmonella enterica* serovar *Typhimurium* or *Typhi*.).

The compositions may be utilized as vaccines or immunogenic compositions for preventing or treating a microbial infection or disease (e.g., mycobacterial infection, infection with a Gram-negative bacteria, anthrax infection, tularemia (e.g., infection by *Francisella tularensis*), plague, malaria, toxoplasmosis, and infection with Cyclospora, infection with other bacteria that utilize the MEP or mevalonate pathway for isoprenoid biosynthesis, and infection with Apicomplexan protozoa). The compositions also may be utilized to prevent or treat a cancer or non-cancerous hyperplasia.

The recombinant attenuated microbes of the disclosed compositions have a mutation in the lytB gene (e.g., a deletion, insertion, or substitution). Typically, the mutations results in a mutant lytB polypeptide having enzymatic activity that is reduced as compared to wild type lytB polypeptide (e.g., by at least about 50%, 70%, 90%, 95%, or 99%). In some embodiments, the mutation is a deletion of at least a portion of the lytB gene.

The recombinant attenuated microbes of the disclosed compositions may include one or more heterologous genes for production of mevalonate. For example, the recombinant attenuated microbes may include one or more of 3-hydroxy-3-methyl-glutaryl-coenzyme A (HMG-CoA) synthase, HMG-CoA reductase, isopentenyl diphosphate isomerase (i.e., IPP isomerase), mevalonate kinase (i.e., MVA kinase), 5-phospho-mevalonate kinase (i.e., PMVA kinase), and phosphomevalonate decarboxylase (i.e., DPMVA decarboxylase).

In some embodiments, the recombinant attenuated microbes of the disclosed compositions may have a mutation in the lytB gene and may produce an elevated amount of (E)-4-hydroxy-3-methyl-but-enyl-pyrophosphate (HMBPP) relative to a microbe having a wild type lytB gene. The recombinant attenuated microbe having the mutation in the lytB gene further may accumulate HMBPP.

The disclosed compositions may include a recombinant attenuated microbe and further may include an antigen. For example the composition may include an antigen for vaccinating against a microbial infection or cancer. In some embodiments, the disclosed compositions may include a recombinant attenuated microbe that expresses a heterologous antigen for vaccinating against a microbial infection or cancer.

The disclosed compositions may be utilized as vaccines or immunogenic compositions for activating, expanding, or stimulating γδ T cells (e.g., as Vγ2Vδ2 T cell vaccines or immunogenic compositions, or Vγ9Vδ2 T cell vaccines or immunogenic compositions). In some embodiments, the disclosed compositions may include a recombinant attenuated microbe and further may include one or more additional agents for activating, expanding, or stimulating γδ T cells (e.g., pyrophosphate compounds such as prenyl pyrophosphates, bisphosphonates, and alkylamines).

Also disclosed are kits that may include the pharmaceutical compositions disclosed herein or that may be used to prepare the pharmaceutical compositions disclosed herein. The kits may be used to practice the methods disclosed herein and may include as components: the pharmaceutical compositions disclosed herein, additional therapeutic or prophylactic agents, and implements for administering the kit components.

DETAILED DESCRIPTION

Figure 1:
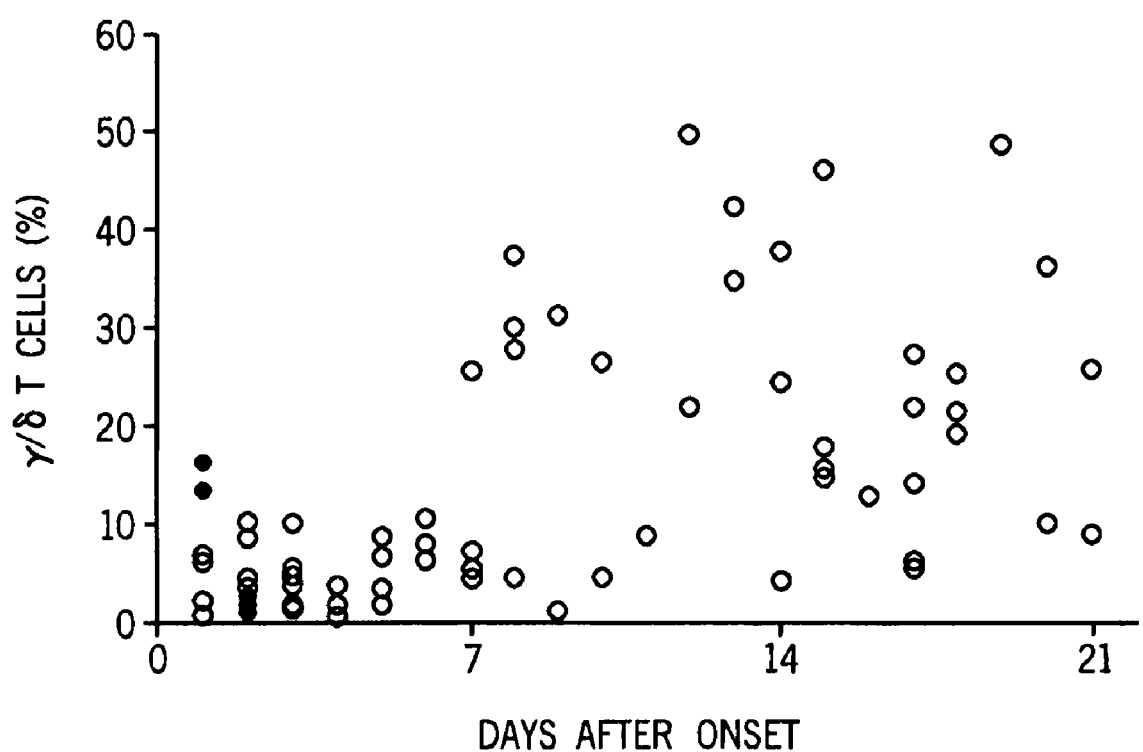
FIG. 1. Blood γδ T cell levels after tularemia infection (as % of CD3 T cells). Increases are due to Vγ2Vδ2 T cells. Figure from Kroca, M., A. Tärnvik, and A. Sjöstedt. 2000, *Clin. Exp. Immunol.* 120: 280-4.

Disclosed are composition, kits, and methods for treating or preventing infection or hyperplasia diseases such as cancer. The compositions may include pharmaceutical compositions that are useful as vaccines or immunogenic compositions for stimulating γδ T cells such as Vγ2Vδ2 T cells.

The compositions may include recombinant attenuated microbes such as a vaccine strain of *Salmonella* (e.g., *Salmonella enterica* serovar *Typhimurium* or *Typhi*.). The disclosed vaccines or immunogenic compositions may be utilized to stimulate human Vγ2Vδ2 T cells due to the overproduction of a microbial metabolite, HMBPP. For example the disclosed vaccines or immunogenic compositions may be administered in vivo to a patient or subject in order to stimulate human Vγ2Vδ2 T cell expansion, where the recombinant attenuated microbes produce HMBPP in vivo after administration to the patient or subject.

Also disclosed are methods for generating recombinant microbes (e.g., bacteria and protozoa). The methods may include mutating the lytB gene (e.g., by deleting at least a portion of the lytB gene). The methods further may include introducing one or more genes of the mevalonate pathway. The methods may be performed in order to generate a live vaccine for stimulating human Vγ2Vδ2 T cells.

Vγ2Vδ2 T cells are important in providing early microbial immunity to most bacteria and parasitic infections including mycobacteria infections, infections with Gram-negative bacteria, anthrax, tularemia (e.g., infection by *Francisella tularensis*), plague, protozoan infections that cause malaria, toxoplasmosis, infection with Cyclospora, infection with other bacteria that utilize the MEP or mevalonate pathway for isoprenoid biosynthesis, and infection with Apicomplexan protozoa. Thus, the disclosed pharmaceutical compositions may be useful for preventing or treating one or more of the afore-mentioned infections or diseases. The disclosed pharmaceutical compositions further may include one or more antigens or recombinant attenuated bacteria present in the compositions may express one or more antigens for inducing an immune response against one or more of the afore-mentioned pathogens.

Vγ2Vδ2 T cells also can mediate tumor immunity and Vγ2Vδ2 T cells can recognize and kill a wide variety of hematopoietic and solid tumors. The disclosed pharmaceutical compositions one or more antigens or recombinant attenuated bacteria present in the compositions may express one or more antigens for inducing an immune response against one or more of the afore-mentioned cancers.

The disclosed pharmaceutical compositions may be useful for providing non-exhaustive immunity. Small molecule vaccines for stimulating Vγ2Vδ2 T cells (e.g., comprising pyrophosphates such as prenyl pyrophosphates, bisphosphonates, and alkylamines) may cause immune exhaustion after 3-4 vaccinations. The presently disclosed compositions may be used as live bacterial vaccines or immunogenic compositions that mimic natural immunity to bacterial infections, which does not exhaust and may persist for months or years.

The present invention is described herein using definitions, as set forth below and throughout the application.

DEFINITIONS

Unless otherwise specified or indicated by context, the terms "a," "an," and "the," mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≦10% of the particular term and "substantially" and "significantly" will mean plus or minus >10% of the particular term.

As used herein, the terms "include" and "including" have the same meaning as the terms "comprise" and "comprising."

A "subject," "patient," or "host" refers to a human or non-human animal having or at risk for acquiring, a microbial infection or cancer. The terms "subject," "patient," or "host" may be used interchangeably. Human or non-human animals may include primates. Individuals who are treated with the pharmaceutical compositions disclosed herein may be at risk for infection or cancer or may have already acquired the infection or cancer. A "subject," "patient," or "host" may include a human or non-human in need of a treatment whereby γδ T cells are activated, expanded, or stimulated (e.g., whereby V2γVδ2 T cells or V9γVδ2 T cells are activated, expanded, or stimulated.

As used herein, "3FBPP" refers to 3-formyl-1-butyl pyrophosphate.

As used herein, "HMBPP" refers to (E)-4-hydroxy-3-methyl-but-2-enyl pyrophosphate.

As used herein, "IPP" refers to isopentenyl pyrophosphate.

As used herein, "MEP" refers to 2-C-methyl-D-erythritol-4 phosphate.

As used herein, "PBMC" refers to peripheral blood mononuclear cells.

As used herein, "SCID" refers to severe combined immunodeficiency.

As used herein, "LytB" refers to an enzyme of the methylerythritol phosphate (MEP) pathway for isoprenoid biosynthesis which is utilized to convert E)-4-hydroxy-3-methyl-but-2-enyl pyrophosphate to isopentenyl pyrophosphate (IPP) and dimethylallyl pyrophosphate (DMAPP). The disclosed recombinant attenuated microbes have a mutation in the lytB gene (e.g., a deletion, insertion, or substitution) that results in reduced activity for the encoded enzyme in comparison to wild type enzyme (e.g., reduced at least about 50%, 70%, 90%, 95%, or 99% in comparison to wild type enzyme) as measured by methods known in the art. (See, e.g., Altincicek, FEBS Letters, Volume 532, Issue 3, Page 437, incorporated by reference herein in its entirety).

Recombinant Attenuated Bacteria

The pharmaceutical compositions disclosed herein typically include a recombinant attenuated microbe (e.g., recombinant attenuated bacteria such as *Salmonella* spp., *Shigella* spp., *Listeria* spp., *Yersinia* spp., and *Escherichia* spp.). Recombinant bacterial vaccines and vectors are described in Daudel et al., "Use of attenuated bacteria as delivery vectors for DNA vaccines," Expert Review of Vaccines, Volume 6, Number 1, February 2007, pp. 97-110(14); Shata et al., "Recent advances with recombinant bacterial vaccine vectors," Molec. Med. Today (2000), Volume 6, Issue 2, 1 Feb. 2000, pages 66-71; Clare & Dougan, "Live Recombinant Bacterial Vaccines," Novel Vaccination Strategies, Apr. 16, 2004 (Editor Stefan H. E. Kaufman); Gentschev et al., "Recombinant Attenuated Bacteria for the Delivery of Subunit Vaccines," Vaccine, Volume 19, Issues 17-19, 21 Mar. 2001, Pages 2621-2628; Garmory et al., "The use of live attenuated bacteria as a delivery system for heterologous antigens," J. Drug Target. 2003; 11(8-10):471-9; U.S. Pat. Nos. 6,383,496; and 6,923,958 (which all are incorporated by reference herein in their entireties).

Formulation of the Pharmaceutical Compositions

The pharmaceutical compositions disclosed herein may be formulated as vaccines or immunogenic compositions for administration to a subject in need thereof. Such compositions can be formulated and/or administered in dosages and by techniques well known to those skilled in the medical arts taking into consideration such factors as the age, sex, weight, and condition of the particular patient, and the route of administration. The compositions may include pharmaceutical carriers, diluents, or excipients as known in the art. Further, the compositions may include anti-microbial or anti-bacterial agents (e.g., benzalkonium chloride) or adjuvants.

The pharmaceutical compositions may be administered prophylactically or therapeutically. In prophylactic administration, the vaccines or immunogenic compositions may be administered in an amount sufficient to induce T cell and antibody responses for protecting against infection. In therapeutic applications, the vaccines or immunogenic compositions are administered to a patient in an amount sufficient to elicit a therapeutic effect (e.g., T cell and antibody responses that cure or at least partially arrest or slow symptoms and complications of an infection or cancer as a "therapeutically effective dose").

The compositions included in the vaccine regimen of the invention can be co-administered or sequentially administered with other immunological, antigenic or therapeutic compositions, including an antigen, adjuvant, a chemical or biological agent. The compositions may include additional agents for activating, expanding, or stimulating $\gamma\delta$ T cells such as pyrophosphate compounds, bisphosphonates, alkylamines, and mixtures thereof.

The pharmaceutical composition disclosed herein may be delivered via a variety of routes. Typical delivery routes include oral administration, intranasal, intravaginal, and intrarectal routes. Other routes include parenteral administration (e.g., intradermal, intramuscular or subcutaneous delivery). The pharmaceutical composition may be formulated for intranasal or pulmonary delivery. Formulations of the pharmaceutical compositions may include liquid formulations (e.g., for oral, nasal, anal, vaginal, etc. administration, including suspensions, syrups or elixirs) and preparations for parenteral, subcutaneous, intradermal, intramuscular or intravenous administration (e.g., injectable administration) such as sterile suspensions or emulsions. Formulations of the bacteria may also be prepared for oral delivery as done for the vaccine strain, *Salmonella enterica* serovar *Typhi* strain Ty21a. Here, bacteria are grown, harvested by centrifugation, mixed with a stabilizer containing sucrose, amino acids, and ascorbic acid, followed by lyophilization. The lyophilized bacteria are mixed with lactose and magnesium stearate as excipients and loaded into enteric-coated gelatin capsules that are coated with an organic solution to render them resistant to stomach acid.

Adjuvants

The term "adjuvant" refers to a compound or mixture that enhances the immune response to an antigen. An adjuvant can serve as a tissue depot that slowly releases the antigen and also as a lymphoid system activator that non-specifically enhances the immune response. Examples of adjuvants which also may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lip or liposomal carrier. Other adjuvants include, but are not limited to, nonionic block co-polymer adjuvants (e.g., CRL1005), aluminum phosphates (e.g., $AlPO_4$), R-848 (a Th1-like adjuvant), imiquimod, PAM3CYS, poly (I:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Prime-Boost Vaccination Regimen

As used herein, a "prime-boost vaccination regimen" refers to a regimen in which a subject is administered a first composition one or more times (e.g., two or three times with about 2, 3, or 4 weeks between administrations) and then after a determined period of time (e.g., about 2 weeks, about 4 weeks, about 2 months, about 3 months, about 4 months, about 5 months, about 6 months, or longer), the subject is administered a second composition, which may be the same as the first composition or different than the first composition. The second composition may also be administered more than once, with at least 2, 3, or 4 weeks between administrations.

Illustrative Embodiments

The following list of embodiments is illustrative and is not intended to limit the scope of the claimed subject matter.

Embodiment 1. An immunogenic composition comprising: (a) an effective amount of a recombinant attenuated microbe for activating, expanding, or stimulating $\gamma\delta$ T cells in a subject, wherein the microbe comprises a mutation in lytB and the microbe comprises one or more heterologous genes for production of mevalonate; (b) an excipient, carrier, or diluent; and optionally (c) an adjuvant.

Embodiment 2. The composition of embodiment 1, wherein the microbe is a bacteria.

Embodiment 3. The composition of embodiment 1 or 2, wherein the bacteria is a *Salmonella* spp.

Embodiment 4. The composition of any of embodiments 1-3, wherein the *Salmonella* spp. is *Salmonella enterica* (e.g. *Salmonella enterica* serovar *Typhimurium* or *Typhi*.).

Embodiment 5. The composition of any of embodiments 1-4, wherein the microbe is a protozoa.

Embodiment 6. The composition of any of embodiments 1-5, wherein the composition is a vaccine that prevents or treats a microbial infection or disease.

Embodiment 7. The vaccine of embodiment 6, wherein the microbial infection or disease is selected from the group consisting of mycobacterial infection, infection with a Gram-negative bacteria, anthrax infection, tularemia (e.g., infection by *Francisella tularensis*), plague, malaria, toxoplasmosis, infection with Cyclospora, infection with other bacteria that utilize the MEP or mevalonate pathway for isoprenoid biosynthesis, and infection with Apicomplexan protozoa.

Embodiment 8. The composition of any of embodiments 1-7, wherein the composition is a vaccine that prevents or treats cancer or a non-cancerous hyperplasia.

Embodiment 9. The composition of any of embodiments 1-8, wherein the mutation results in a mutant lytB polypeptide having enzymatic activity reduced at least about 50% as compared to wild type lytB polypeptide.

Embodiment 10. The composition of any of embodiments 1-9, wherein the mutation results in a mutant lytB polypeptide having enzymatic activity reduced at least about 90% as compared to wild type lytB polypeptide.

Embodiment 11. The composition of any of embodiments 1-10, wherein the mutation is a deletion.

Embodiment 12. The composition of any of embodiments 1-11, wherein the mutation is an insertion.

Embodiment 13. The composition of embodiment 12, wherein the insertion is a gene for antibiotic resistance.

Embodiment 14. The composition of any of embodiments 1-13, wherein the one or more heterologous genes for production of mevalonate are selected from the group consisting of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

Embodiment 15. The composition of embodiment 14, wherein the microbe comprises heterologous genes for production of mevalonate including each of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

Embodiment 16. The composition of any of embodiments 1-15, wherein the recombinant attenuated microbe having the mutation in the lytB gene produces an elevated amount of (E)-4-hydroxy-3-methyl-but-enyl-pyrophosphate (HMBPP) relative to a microbe having a wild type lytB gene.

Embodiment 17. The composition of any of embodiments 1-16, wherein the recombinant attenuated microbe having the mutation in the lytB gene accumulates HMBPP.

Embodiment 18. The composition of any of embodiments 1-17, further comprising an antigen for vaccinating against a microbial infection or cancer.

Embodiment 19. The composition of any of embodiments 1-18, wherein the microbe expresses a heterologous antigen for vaccinating against a microbial infection or cancer.

Embodiment 20. The composition of any of embodiments 1-19, further comprising one or more additional agents for activating, expanding, or stimulating γδ T cells.

Embodiment 21. The composition of embodiment 20, wherein the additional agent is selected from a group consisting of pyrophosphate compounds, bisphosphonates, and alkylamines.

Embodiment 22. The composition of any of embodiments 1-21, wherein the γδ T cells are human Vγ2Vδ2 T cells.

Embodiment 23. A method for activating, expanding, or stimulating γδ T cells in a subject, the method comprising administering to the subject the composition of any of embodiments 1-22.

Embodiment 24. The method of embodiment 23, wherein the γδ T cells are human Vγ2Vδ2 T cells.

Embodiment 25. A recombinant attenuated *Salmonella* spp. bacteria, wherein the bacteria comprises a mutation in lytB and the bacteria comprises one or more heterologous genes for production of mevalonate.

Embodiment 26. The bacteria of embodiment 25, wherein the *Salmonella* spp. bacteria is *Salmonella enterica* (e.g., *Salmonella enterica* serovar *Typhimurium* or *Typhi*.).

Embodiment 27. The bacteria of embodiment 25 or 26, wherein the mutation results in a mutant lytB polypeptide having enzymatic activity reduced at least about 50% as compared to wild type lytB polypeptide.

Embodiment 28. The bacteria of any of embodiments 25-27, wherein the mutation results in a mutant lytB polypeptide having enzymatic activity reduced at least about 90% as compared to wild type lytB polypeptide.

Embodiment 29. The bacteria of any of embodiments 25-28, wherein the mutation is a deletion.

Embodiment 30. The bacteria of any of embodiments 25-29, wherein the mutation is an insertion.

Embodiment 31. The bacteria of embodiment 30, wherein the insertion is a gene for antibiotic resistance.

Embodiment 32. The bacteria of any of embodiments 25-31, wherein the one or more heterologous genes for production of mevalonate are selected from the group consisting of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

Embodiment 33. The bacteria of embodiment 32, wherein the microbe comprises heterologous genes for production of mevalonate including each of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

EXAMPLES

The following Examples are illustrative and are not intended to limit the scope of the claimed subject matter.

Example 1

Preparation of Vaccine Against *Francisella tularensis* Using Live Attenuated *Salmonella* Strain Background

*Francisella* tularensis infects at local sites before being disseminated throughout the body via bacteremia and infected macrophages. The first few days of infection are often critical in determining whether or not the host will survive. Positioned at the interface between innate and adaptive immunity, NK cells and γδ T cells are present in large numbers and respond rapidly to infection by a variety of viruses, bacteria, and parasites. These "rapid response" lymphocytes kill infected cells and secrete large amounts of IFN-γ and TNF-α that stimulate infected macrophages to kill intracellular bacteria. Human Vγ2Vδ2 T cells expand rapidly during tularemia infections to very high levels (22-50% of circulating T cells) supporting their important role in this infection. It has been shown that identical expansions of monkey Vγ2Vδ2 T cells have characteristics of memory T cell responses and that these expansions coincide with the resolution of mycobacterial infections. Further, it has been found that Vγ2Vδ2 T cells use their TCRs to recognize bacterial and protozoal infections by responding to a common microbial metabolic intermediate, (E)-4-hydroxy-3-methyl-but-2-enyl pyrophosphate (HMBPP). In support of T cell memory for γδ T cells, it further has been found that adult Vγ2Vδ2 T cells are almost exclusively memory cells that are divided into 3 subsets, central memory, effector memory, and effector CD45RA$^+$ memory.

Despite the importance of Vγ2Vδ2 T cells in human tularemia, there are no vaccines that stimulate this T cell subset. It has been found that bacteria with deletions of the enzyme, lytB, overproduce HMBPP, and therefore, these recombinant bacteria may serve as live bacterial vaccines. The proposed studies will elucidate the critical role of Vγ2Vδ2 T cells in tularemia and will develop vaccines that target Vγ2Vδ2 T cells. Specific aims include: Aim I. Test Vγ2Vδ2 T cell recognition of *F. tularensis* infected epithelial cells, monocytes, and macrophages (a. assess cytolysis of infected cells; b. measure IFN-γ secretion in response to infected cells; c. assess killing of intracellular *F. tularensis*); Aim II. Determine the contribution of Vγ2Vδ2 T cell to the survival of huPBMC-SCID-beige mice infected with *F. tularensis*; Aim III. Derive live bacterial vaccines for Vγ2Vδ2 T cells that overproduce HMBPP from attenuated *Salmonella*; Aim IV. Test HMBPP/adjuvant vaccines and live bacterial vaccines for their ability to stimulate Vγ2Vδ2 T cells in a primate model (a. determine the ability of HMBPP vaccines to expand Vγ2Vδ2 T cells in vivo; b. assess the effects of HMBPP vaccines on Vγ2Vδ2 T cell naïve and memory subsets; c. determine the ability of HMBPP vaccines to increase the reactivity of Vγ2Vδ2 T cells to nonpeptide antigens in vitro; d. determine the ability of Vγ2Vδ2 T cells to mount memory responses upon subsequent HMBPP vaccination in vivo).

*Francisella* tularensis infects locally before being disseminated throughout the body via bacteremia and infected macrophages. (See Malkovska, V., F. K. Cigel, N. Armstrong, B. E. Storer, and R. Hong. 1992. Antilymphoma activity of human γδ T-cells in mice with severe combined immune deficiency. Cancer Res. 52: 5610-6; Malkovska, V., F. Cigel, and B. E. Storer. 1994. Human T cells in hu-PBL-SCID mice proliferate in response to Daudi lymphoma and confer anti-tumour immunity. Clin. Exp. Immunol. 96: 158-65; and Wang, L., A. Kamath, H. Das, L. Li, and J. F. Bukowski. 2001. Antibacterial effect of human Vγ2Vδ2 T cells in vivo. J. Clin. Invest. 108: 1349-57). In skin infections, *F. tularensis* first infects epithelial cells (keratinocytes) before spreading to macrophages. (See Ellis, J., P. C. Oyston, M. Green, and R. W. Titball. 2002. Tularemia. Clin. Microbiol. Rev. 15: 631-46). With an infectious dose of less than 10 CFU in human skin, *F. tularensis* infection has a mortality rate of 5-6% in untreated individuals. (See id.). *F. tularensis* also infects through the eye, the oropharynx, gastrointestinal (GI) tract, and the lung. The oropharynx and GI tract are relevant to potential contamination of food and water supplies by bioterrorists. (See Dennis, D. T., T. V. Inglesby, D. A. Henderson, J. G. Bartlett, M. S. Ascher, E. Eitzen, A. D. Fine, A. M. Friedlander, J. Hauer, M. Layton, S. R. Lillibridge, J. E. McDade, M. T. Osterholm, T. O'Toole, G. Parker, T. M. Perl, P. K. Russell, and K. Tonat. 2001. Tularemia as a biological weapon: medical and public health management. JAMA 285: 2763-73). The ability of aerosols to infect the lungs may be the biggest bioterrorism threat. (See Ellis et al. supra; and Dennis et al. supra).

At least in mice, control of tularemia infection may require both CD4 and CD8 T cells. (See Ellis et al. supra). Similar to viruses and other bacteria, adaptive CD4 and CD8 T cell responses appear to have little role in protecting naive hosts early in infection. When mortality was measured 10 days post infection, the LD$_{50}$ for intradermal *F. tularensis* challenge was identical for αβ T cell-deficient nude mice and normal mice. (See Elkins, K. L., T. Rhinehart-Jones, C. A. Nacy, R. K. Winegar, and A. H. Fortier. 1993. T-cell-independent resistance to infection and generation of immunity to *Francisella* tularensis. Infect. Immun. 61: 823-9). However, αβ T cells prevented later mortality. This pattern is reminiscent of the immune response to *Listeria monocytogenes* in which T cells are required for long-term survival, but NK cells are needed for short-term survival. (See Bancroft, G. J., R. D. Schreiber, and E. R. Unanue. 1991. Natural immunity: a T-cell-independent pathway of macrophage activation, defined in the SCID mouse. Immunol. Rev. 124: 5-24). The parallel between these two intracellular pathogens suggests the possibility that γδ T cells expressing Vγ2Vδ2 T cell receptors and NK cells are required to control *F. tularensis* early in human infection. IFN-γ is critical for control of *F. tularensis* infection in vivo and this cytokine is produced at high levels by human Vγ2Vδ2 T cells. (See Elkins et al. supra; Wang et al. supra; and García, V. E., P. A. Sieling, J.-H. Gong, P. F. Barnes, Y. Tanaka, B. R. Bloom, C. T. Morita, and R. L. Modlin. 1997. Single cell cytokine analysis of γδ T cell responses to nonpeptide mycobacterial antigens. J. Immunol. 159: 1328-35). In vitro, low-dose IFN-γ induces mouse alveolar and peritoneal macrophages and human monocytes to kill intracellular *F. tularensis*. (See Ellis et al. supra; and Fortier, A. H., S. J. Green, T. Polsinelli, T. R. Jones, R. M. Crawford, D. A. Leiby, K. L. Elkins, M. S. Meltzer, and C. A. Nacy. 1994. Life and death of an intracellular pathogen: *Francisella* tularensis and the macrophage. Immunol Ser. 60: 349-61). In the human system, the IFN-γ effect could not be reproduced by a variety of other stimulatory agents known to activate monocytes, such as IFN-α, TNF-α, IL-1β, IL-2, IL-4, IL-6, M-CSF, GM-CSF, TGF-β, LPS, and PMA. (See Fortier et al. supra).

Figure 2:
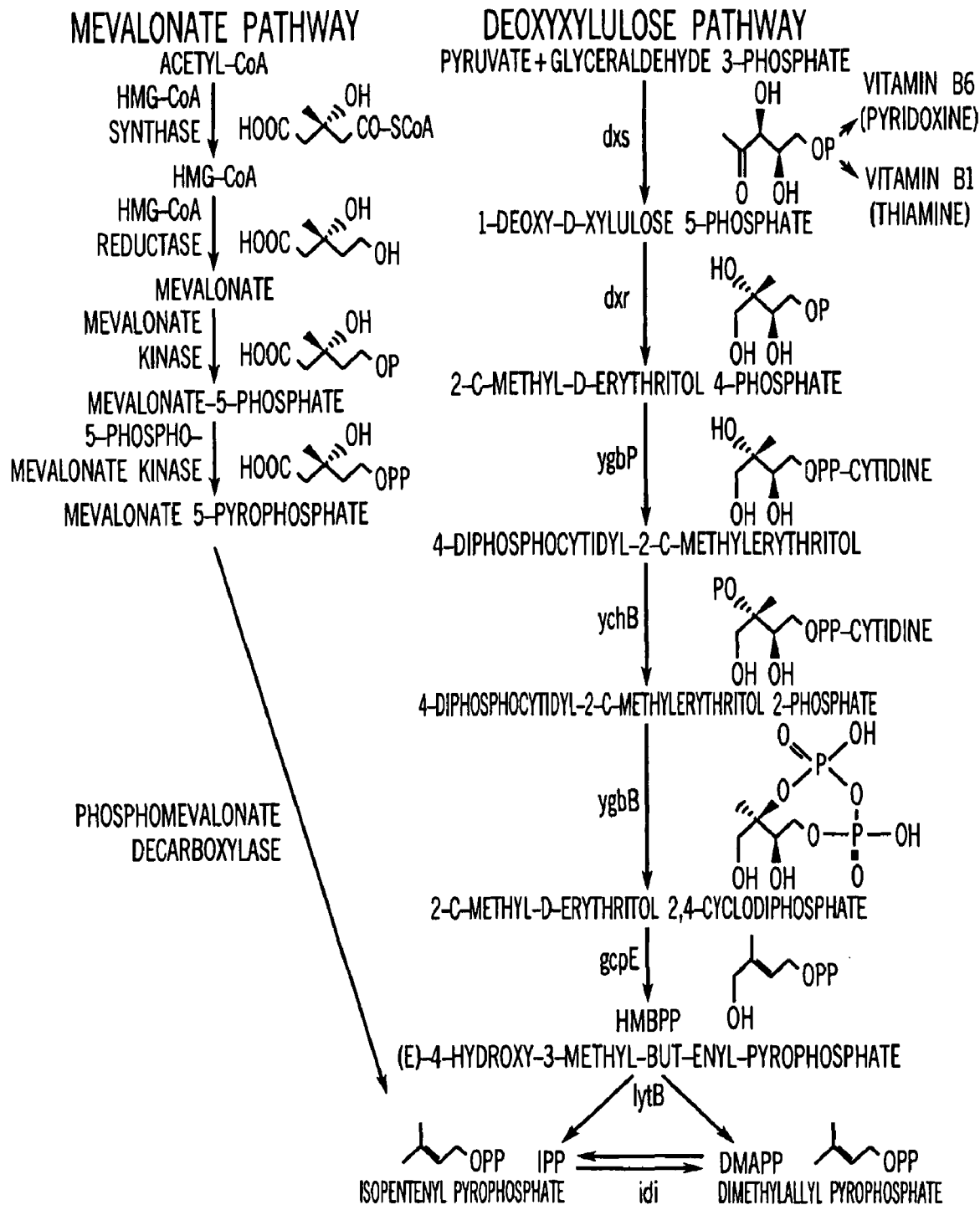
FIG. 2. Two pathways for the synthesis of IPP. Most Eubacteria and some Eukayotic parasitic protozoa, such as malaria and *toxoplasma*, use the deoxyxylulose pathway to synthesize IPP. Most Eukayotic species including humans and Archibacteria use the mevanolate pathway to make IPP. Vγ2Vδ2 T cells recognize the metabolite, HMBPP, which is produced by gcpE and converted by lytB to IPP and DMAPP.

Available evidence strongly suggests that Vγ2Vδ2 T cells are important in human immune responses to *F. tularensis*. Both γδ T cells and NK cells respond rapidly to many types of infection and secrete abundant IFN-γ. Within a week of tularemia onset, patients had elevated levels of circulating Vγ2Vδ2 T cells (FIG. 1). The infection leads to very high levels of Vγ2Vδ2 T cells such that the mean levels in patients two weeks after infection are between 22-50% of total T cells and these increases can persist for over 1 year. (See Sumida, T., T. Maeda, H. Takahashi, S. Yoshida, F. Yonaha, A. Sakamoto, H. Tomioka, T. Koike, and S. Yoshida. 1992. Predominant expansion of Vγ9/Vδ2 T cells in a tularemia patient. Infect. Immun. 60: 2554-8; Poquet, Y., M. Kroca, F. Halary, S. Stenmark, M.-A. Peyrat, M. Bonneville, J. J. Fournié, and A. Sjöstedt. 1998. Expansion of Vγ9Vδ2 T cells is triggered by *Francisella* tularensis-derived phosphoantigens in tularemia but not after tularemia vaccination. Infect. Immun. 66: 2107-14; and Kroca, M., A. Tärnvik, and A. Sjöstedt. 2000). The proportion of circulating γδ T cells increases after the first week of onset of tularaemia and remains elevated for more than a year. Clin. Exp. Immunol. 120: 280-4 Vγ2Vδ2 T cell responses in tularemia were linked to phosphatase-sensitive *F. tularensis* antigens. (See Poquet et al. supra). It now has been shown that these Vγ2Vδ2 T cell responses are due to the recognition of an intermediate, (E)-4-hydroxy-3-methyl-but-2-enyl pyrophosphate (HMBPP), from the metabolic pathway that produces isopentenyl pyrophosphate in Gram negative, many Gram positive bacteria, and some parasitic protozoa (FIG. 2).

The first few days of infection are often critical in determining whether or not the host will survive. Positioned at the interface between innate and adaptive immunity, NK cells and γδ T cells are present in large numbers and respond rapidly to infection by a variety of viruses, bacteria, and parasites. These "rapid response" lymphocytes kill infected cells and secrete considerable IFN-γ, stimulating infected macrophages to kill intracellular bacteria. These early "bridge" responses limit the spread of infected cells and allow the host to survive until adaptive T and B cell immune responses are activated. In addition, the adaptive responses are shaped by IFN-γ and other cytokines secreted by NK cells and γδ T cells. An understanding of how γδ T cells recognize *F. tularensis* and the development of vaccines stimulating these cells will boost the response of these cells in the critical early days of infection following a bioterrorist attack.

Results and Discussion (E)-4-hydroxy-3-methyl-but-2-enyl pyrophosphate (HMBPP) is the major bacterial and protozoal antigen for Vγ2Vδ2 T cells and is an intermediate in the deoxyxylulose pathway for isopentenyl pyrophosphate synthesis—We have isolated and identified the major prenyl pyrophosphate antigen from *M. smegmatis* and *M. fortuitum* as HMBPP by HPLC and mass spectrometry. HMBPP is an intermediate in the deoxyxylulose synthetic pathway for IPP and DMAPP (FIG. 2). *Mycobacteria, Salmonella, Neisseria meningitidis, Ehrlichia chaffeensis*, and *Francisella* tularensis all use the deoxyxylulose pathway as do the eukaryotic Apicomplexan protozoal parasites, such as *plasmodium* and *toxoplasma*. These infections are all associated with Vγ2Vδ2 T cells expansions. We have found that synthetic HMBPP is extremely potent, stimulating ½ max proliferation at a concentration of 31.6 pM; ~30,000 fold more active than IPP on a molar basis. (See Tanaka, Y., C. T. Morita, Y. Tanaka, E. Nieves, M. B. Brenner, and B. R. Bloom. 1995. Natural and synthetic non-peptide antigens recognized by human γδ T cells. Nature 375: 155-8). The recognition by γδ T cells of a bacterial and protozoal metabolic intermediate is analogous to the innate immune system's recognition of pathogen-associated molecular patterns. This pattern recognition of adaptive γδ T cells allows the expansion of memory T cells that can then respond early in infections to produce Th1 cytokines and to kill infected cells and bacteria. In this way, γδ T cells may provide bridge immunity between innate and adaptive immune responses by providing adaptive, secondary T cell immunity to primary infections. (See Morita, C. T., R. A. Mariuzza, and M. B. Brenner. 2000. Antigen recognition by human γδ T cells: pattern recognition by the adaptive immune system. Springer Semin. Immunopathol. 22: 191-218).

Figure 3:
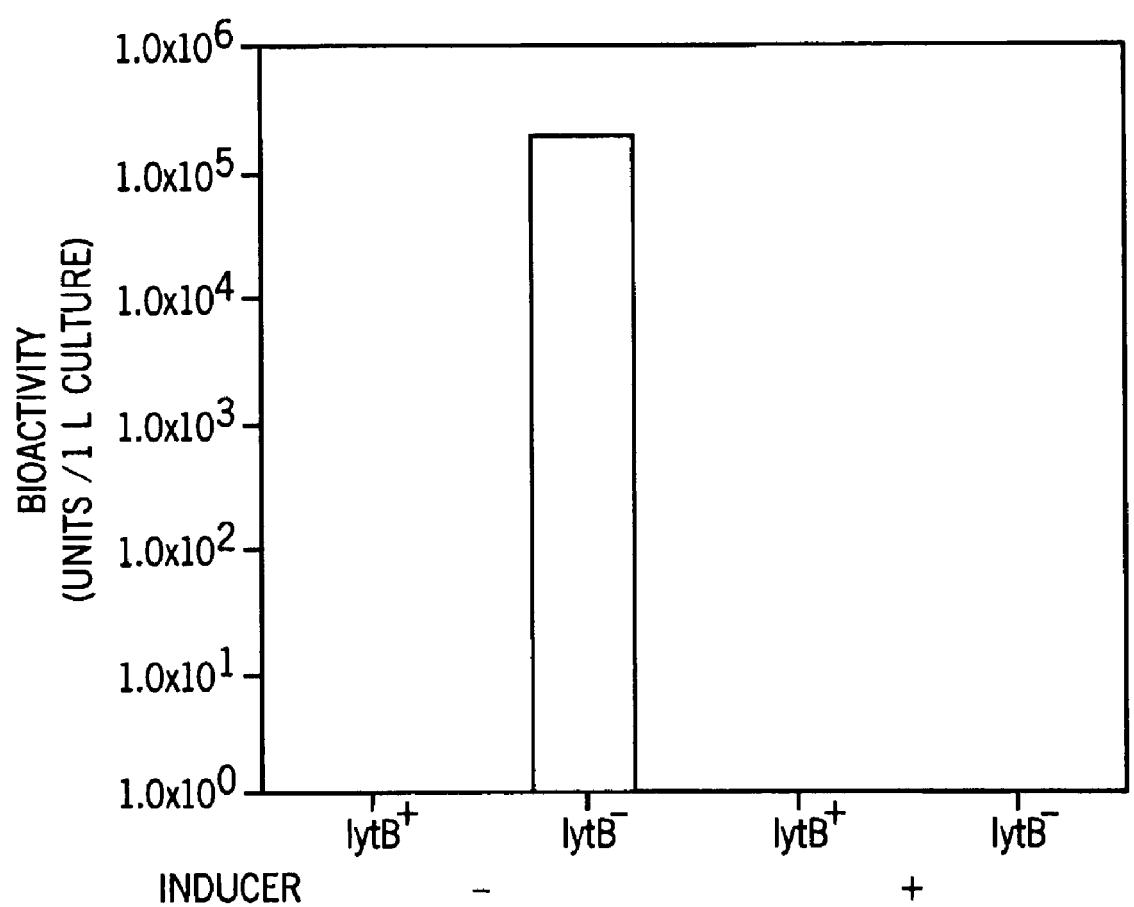
FIG. 3. Deletion of lytB in the *Salmonella typhimurium* SL7207 vaccine strain greatly increases HMBPP levels. After lytB gene was deleted in *S. typhimurium* SL7207 by homologous recombination, lytB was introduced on an arabinose-inducible plasmid that is slightly "leaky" for lytB transcription. 1 unit of bioactivity corresponds to 3 attamoles of HMBPP.

Live vaccine strain, *Salmonella typhimurium* strain SL7207, can be genetically modified to overproduce HMBPP—Several bacterial strains used for live immunizations are reported to have low levels of bioactivity for Vγ2Vδ2 T cells. (See Poquet et al. supra; and Constant, P., Y. Poquet, M.-A. Peyrat, F. Davodeau, M. Bonneville, and J.-J. Fournié. 1995. The antituberculous *Mycobacterium bovis* BCG vaccine is an attenuated mycobacterial producer of phosphorylated nonpeptidic antigens for human γδ T cells. Infect. Immun. 63: 4628-33). Therefore, we altered the deoxyxylulose pathway in a live vaccine strain of *Salmonella* (*Salmonella typhimurium* strain SL7207) to derive a strain that overproduces HMBPP. First, the lytB homolog in this vaccine strain was deleted and lytB was placed under an inducible promoter. HMBPP levels were increased from barely detectable to 190,000 bioactivity units/L culture (FIG. 3). Induction of lytB with arabinose decreased HMBPP levels to barely detectable levels. Similar increases in HMBPP after lytB deletion were noted in the pathogenic *Salmonella typhimurium* strain SL 1344 (data not shown).

Figure 4:
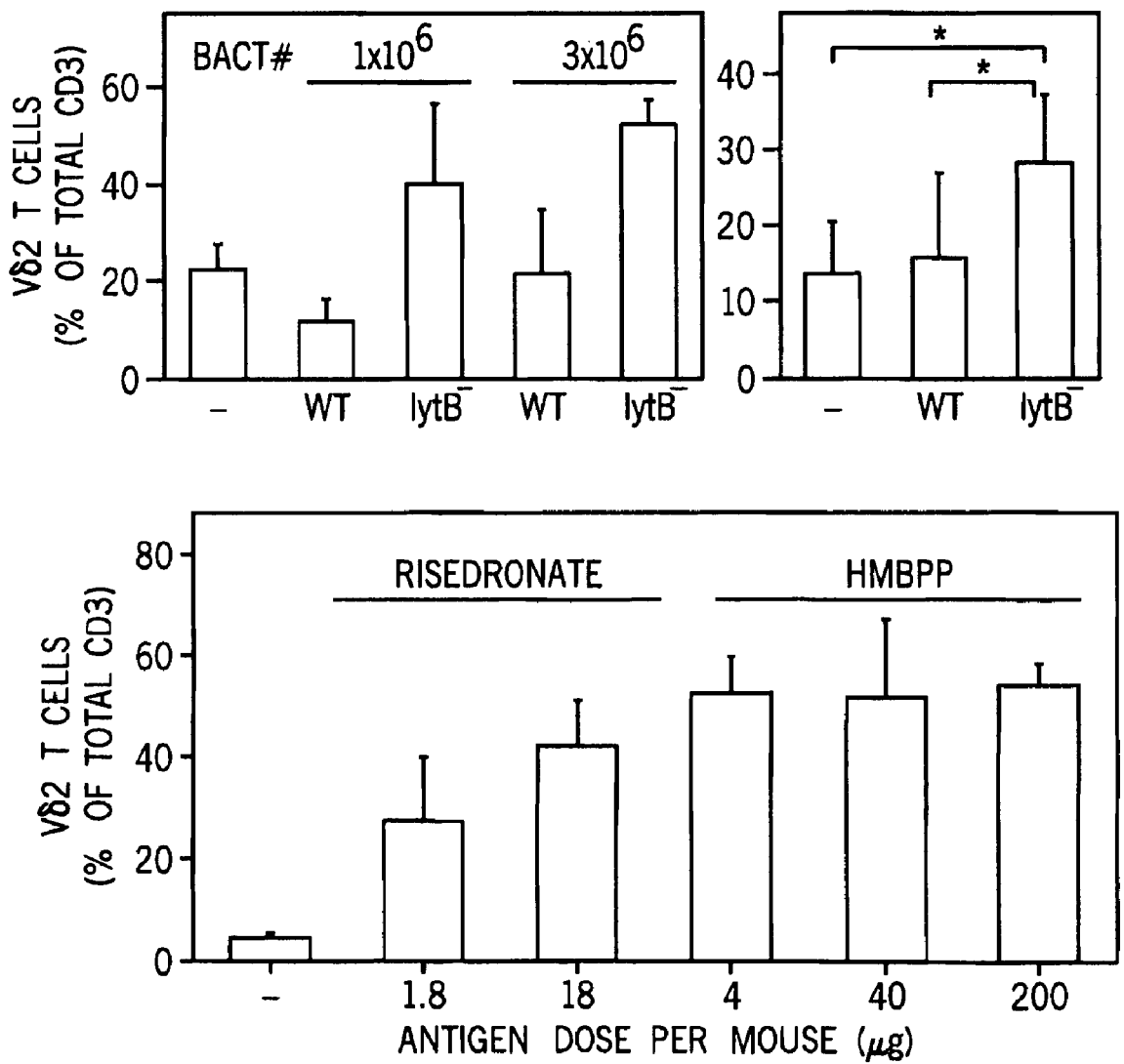
FIG. 4. In vivo expansion of Vγ2Vδ2 T cells in huPBMC-SCID-beige mice. (Top) SCID-beige mice were reconstituted with $3 \times 10^7$ freshly isolated PBMC i.p. and challenged with $1 \times 10^6$ or $3 \times 10^6$ (left) or $1 \times 10^6$ (right) wt or lytB− *E. coli*. On d9 the peritoneum was lavaged and Vγ2Vδ2 T cells determined by FACS. Different donors were used for Exp. 1 and 2. *p<0.01. (Bottom) HMBPP and the bisphosphonate, risedronate, expand Vγ2Vδ2 T cells in huPBMC-SCID-beige mice. Mice were reconstituted as above and immunized with HMBPP or risedronate with CpG ODN 2216 (10 μg/mouse). The mice also received rIL-2 (5000 IU i.p. QOD).

HMBPP overproducing bacteria stimulate Vγ2Vδ2 T cells from PBMC in the hu-PBMC-SCID-beige mouse model; Implications for live vaccines—While not exactly mimicking the human situation, the human PBMC-SCID-beige mouse model can provide insights into in vivo γδ T cell functions. (See Wang et al. supra). We used this model to determine if HMBPP levels plays a role in determining a bacteria's ability to stimulate Vγ2Vδ2 T cells in vivo. When freshly isolated adult PBMC were transplanted into SCID-beige mice, the lytB⁻ (high HMBPP) mutant stimulated significant Vγ2Vδ2 T cell expansion (FIG. 4, top). Direct immunization with HMBPP or with the bisphosphonate, risedronate, also expanded Vγ2Vδ2 T cells (FIG. 4, bottom). Thus, HMBPP levels clearly play roles in determining Vγ2Vδ2 T cell activation in this model.

Derivation of a new mutant *Salmonella typhimurium* strain SL7207 that constitutively overproduces large amounts of HMBPP—To derive a live bacterial vaccine for Vγ2Vδ2 T cells, we mutated attenuated *Salmonella* to overproduce HMBPP by deleting the gene for the downstream LytB enzyme in the deoxyxylulose pathway. For these studies, we used the plasmid pTMV19, which expresses enzymes for the mevalonate pathway from *Streptomyces* sp. strain CL190. We previously used this plasmid successfully to complement mutant *Escherichia coli* that had mutations in the deoxyxylulose pathway. However, our similar attempt using the vaccine strain *Salmonella typhimurium* SL7207 was unsuccessful. Therefore, we further attempted to use the pMBIS plasmid (courtesy of Dr. Jay Keasling). This plasmid encodes mevalonate pathway enzymes from the yeast *Saccoromyces cerviciae*. Dr. Keasling has reported that the prenyl pyrophosphate intermediates, isopentenyl pyrophosphate (IPP) and dimethylallyl pyrophosphate (DMAPP), are toxic for bacteria if produced in large amounts. To overcome this toxicity, Dr. Keasling used plasmids that were present at low copy number in bacteria or introduced plasmids for downstream enzymes that use IPP and DMAPP to synthesize isoprenoid compounds. However, our attempts to use the pMBIS plasmid to derive a lytB⁻ *Salmonella* mutant of *Salmonella typhimurium* SL7207 also were unsuccessful.

Figure 5:
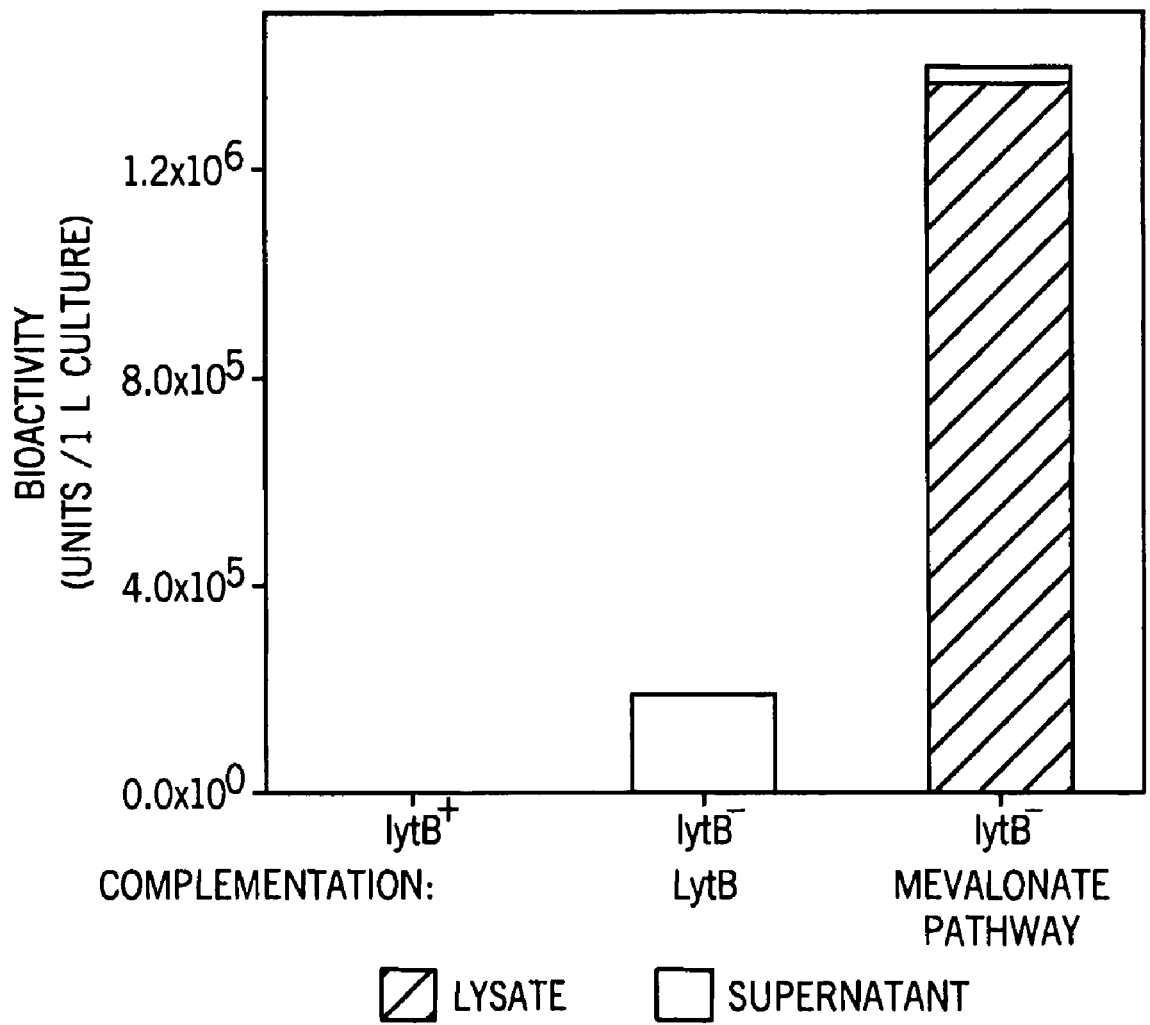
FIG. 5. Deletion of lytB in the *Salmonella typhimurium* vaccine strain SL7207 complemented by the mevalonate pathway leads to very high levels of intracellular HMBPP. Bioactivity levels were 7.2 fold higher than those achieved with complementation with inducible LytB. 1 unit/ml is equivalent to 6 pM HMBPP.

Based on the hypothesis that overproduction of IPP and DMAPP was toxic for *Salmonella*, we obtained the plasmids pMMV19 and pMMV22 (courtesy Dr. Tomohisa Kuzuyama). These plasmids are derived from the plasmid pSC101, which is maintained at low copy number in bacteria (only 1-5 copies per bacteria). The plasmid pMMV19 includes the full mevalonate pathway operon from *Streptomyces* sp. strain CL190 (i.e., genes for HMG-CoA synthase, HMG-CoA reductase, MVA kinase, PMVA kinase, DPMVA decarboxylase, and IPP isomerase). The plasmid pMMV22 includes a portion of the mevalonate pathway operon from *Streptomyces* sp. strain CL190 (i.e., genes for MVA kinase, PMVA kinase, DPMVA decarboxylase, and IPP isomerase). Using pMMV22, we successfully created a deletion in the lytB gene of *Salmonella typhimurium* SL7207. The lytB⁻ *Salmonella* mutant derived as such expressed an increased amount of the HMBPP intermediate. Bioactivity for Vγ2Vδ2 T cells increased from undetectable levels in wild type *Salmonella typhimurium* SL7207 to $1.39 \times 10^6$ units for the mutant (1 unit/ml is equivalent to 6 pM) (FIG. 5). This level is 7.2× fold higher than the level of the lytB⁻ mutant which was complemented with LytB on an inducible plasmid as described above. Also, the bioactivity found with lytB⁻ mutants complemented with LytB was in the supernatant whereas almost all of the bioactivity found with lytB⁻ mutants complemented with the mevalonate pathway was located inside the bacteria (FIG. 5).

Figure 6:
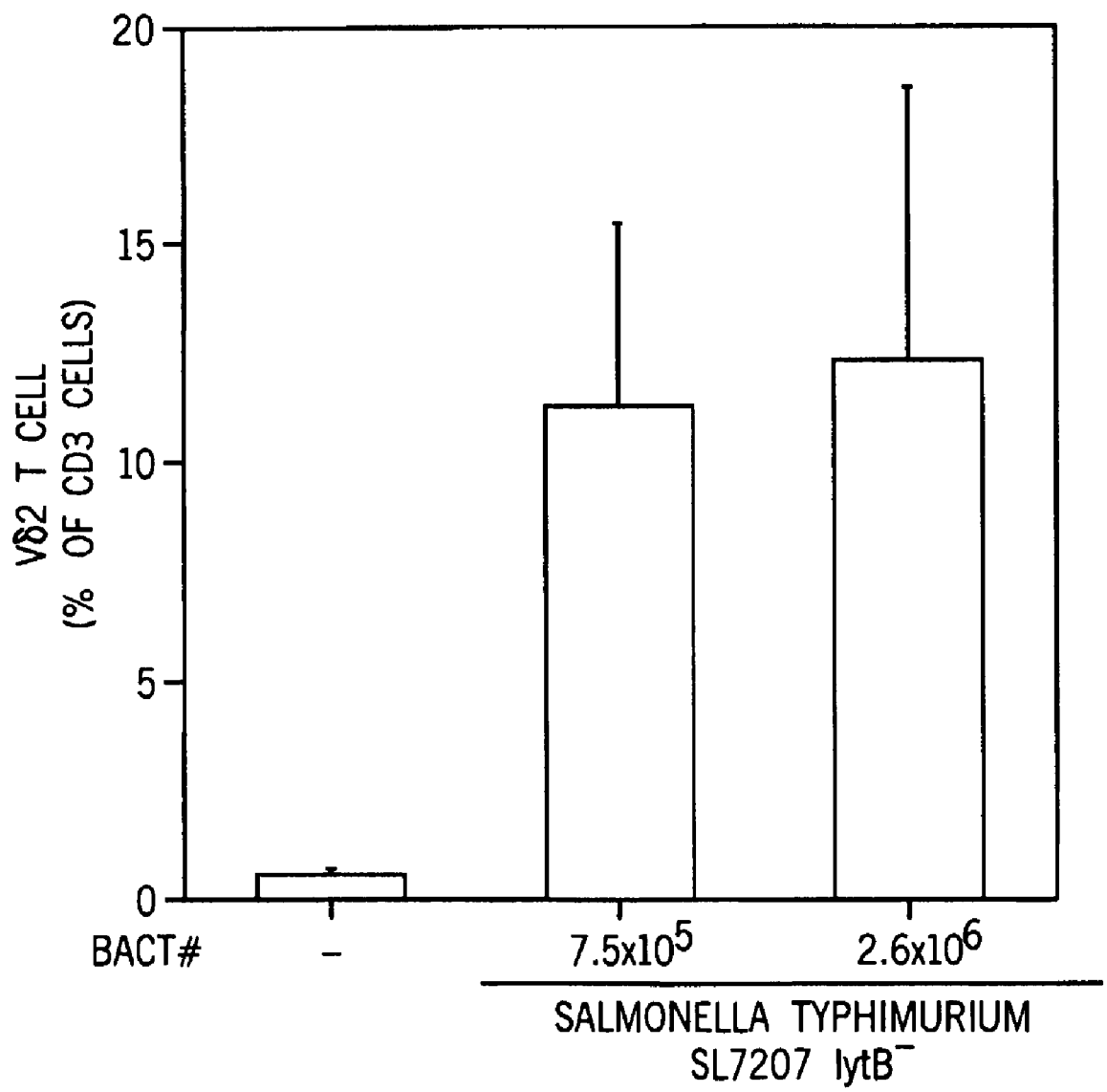
FIG. 6. Immunization by lytB− *Salmonella typhimurium* vaccine strain SL7207 complemented by the mevalonate pathway leads to expansion of Vγ2Vδ2 T cells in huPBL-SCID-beige mice. SCID-beige mice were reconstituted with $3 \times 10^7$ PBMC i.p. and challenged with $7.5 \times 10^5$ or $2.6 \times 10^6$ lytB− *Salmonella*. On d9 the peritoneum was lavaged and Vγ2Vδ2 T cells determined by FACS.

To determine if lytB⁻ *Salmonella typhimurium* SL7207 complemented with the mevalonate pathway could stimulate Vγ2Vδ2 T cell in vivo, we infected SCID-beige mice with the lytB⁻ or wild type *Salmonella typhimurium* SL7207 in the presence of PBMC from a normal donor. Whereas no expansion of Vγ2Vδ2 T cells was noted in the absence of the bacteria, with the lytB⁻ bacteria, Vγ2Vδ2 T cells expanded from 0.5% to 11.3% and 12.4% of CD3⁺ T cells (FIG. 6). Thus, the presence of high levels of HMBPP in the mutant bacteria was associated with in vivo expansion of human Vγ2Vδ2 T cells.

Figure 7A:
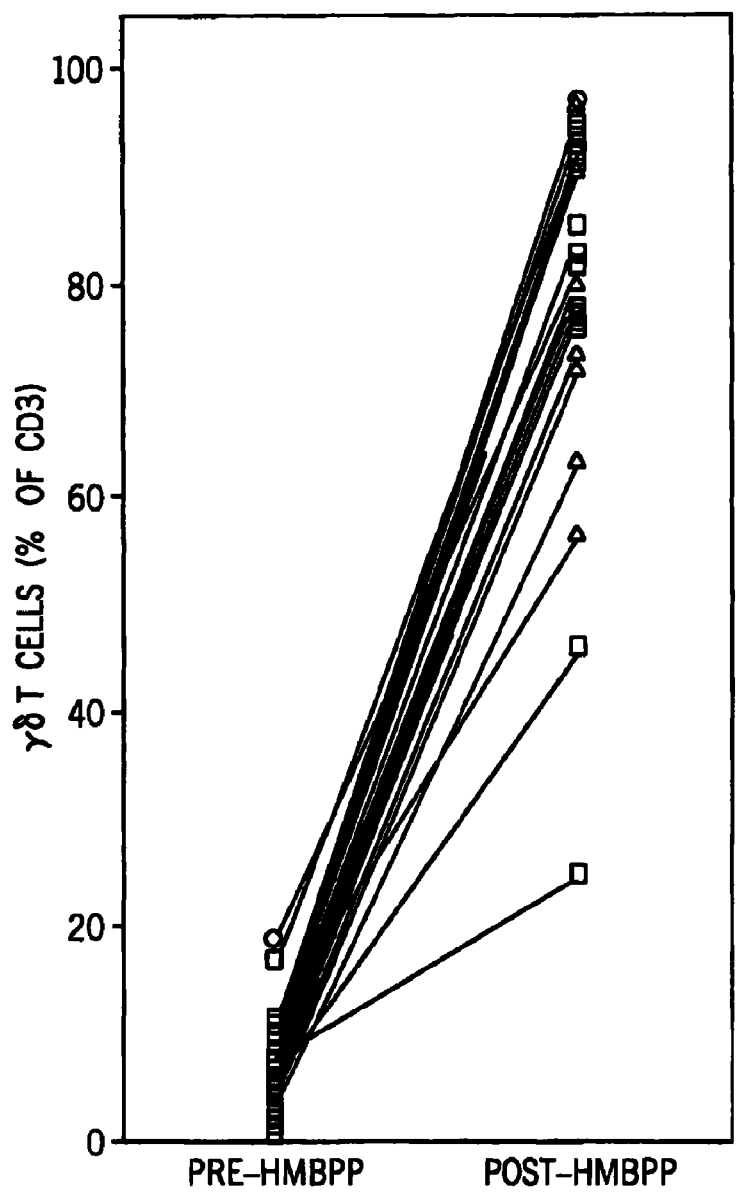
FIG. 7. Characteristics of rhesus monkey Vγ2Vδ2 T cells. (A). Large in vitro HMBPP responses by Vγ2Vδ2 T cells from most rhesus monkeys. Expansion of Vγ2Vδ2 T cells to >40% were observed in 32/33 monkeys after stimulation of PBMC with 100 nM HMBPP. (B). Uniform memory subset distribution of rhesus monkey Vγ2Vδ2 T cells. PBMC from 22 monkeys were stained for Vδ2, CD28, and CD28. Vδ2+ cells were divided in 4 groups based on their expression of CD28 and CD27.
Figure 7B:
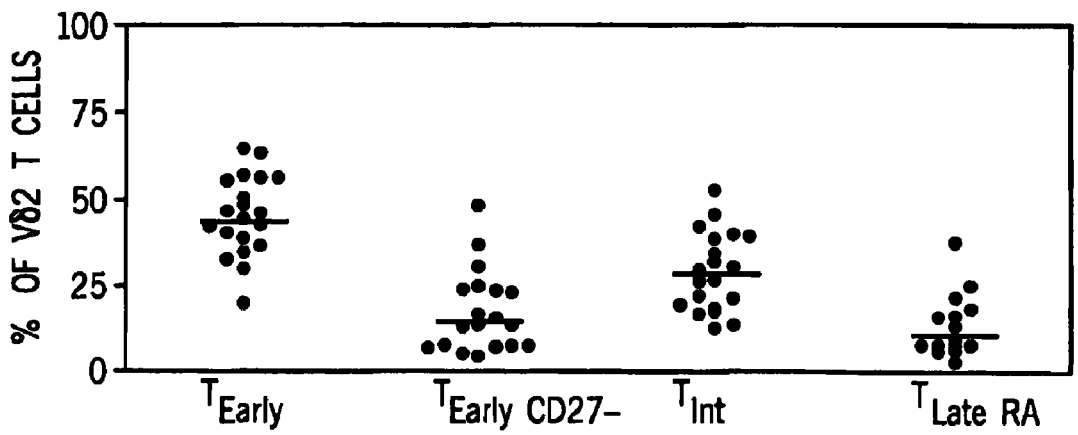

Memory subset distribution and HMBPP response of rhesus monkey Vγ2Vδ2 T cells—In preparation for in vivo immunization of rhesus monkey, we screened 33 monkeys for their ability to respond to HMBPP in vitro, γδ T cells levels, V gene expression, and memory subset distribution. Expansion of Vγ2Vδ2 T cells to >40% were observed in 32/33 monkeys after stimulation of PBMC with 100 nM HMBPP in vitro (FIG. 7A). Like human Vγ2Vδ2 T cells, monkey Vγ2Vδ2 T cells also could be divided into 4 subsets based on expression of CD28 and CD27 ($T_{Early}$=central memory=CD28⁺27⁺, $T_{Early\ CD27-}$=CD28⁺27⁻, $T_{Intermediate}$=CD28⁻27⁺, and $T_{Late\ CD45RA+}$=CD28⁻27⁻). However, unlike human donors, there were very few monkeys with a predominance of the $T_{Late\ RA}$ subset. Moreover, whereas Vγ2Vδ2 T cells constituted 73% of human adult γδ T cells, Vγ2Vδ2 T cells constituted only 29% of monkey γδ T cells consistent with our earlier study. (See Morita, C. T., C. M. Parker, M. B. Brenner, and H. Band. 1994. T cell receptor usage and functional capabilities of human γδ T cells at birth. J. Immunol. 153: 3979-88; Wang, H., H. K. Lee, J. F. Bukowski, H. Li, R. A. Mariuzza, Z. W. Chen, K.-H. Nam, and C. T. Morita. 2003. Conservation of nonpeptide antigen recognition by rhesus monkey Vγ2Vδ2 T cells. J. Immunol. 170: 3696-706). These results suggest that these 5-9 year old monkeys are less exposed to bacterial infections that expand and differentiate human Vγ2Vδ2 T cells. (See Parker, C. M., V. Groh, H. Band, S. A. Porcelli, C. Morita, M. Fabbi, D. Glass, J. L. Strominger, and M. B. Brenner. 1990. Evidence for extrathymic changes in the T cell receptor γ/δ repertoire. J. Exp. Med. 171: 1597-612). Given the high level of reactivity, rhesus monkeys are excellent animal models to test immunization strategies for Vγ2Vδ2 T cells. Twelve monkeys were received for testing vaccines that include lytB⁻ bacteria. In addition to live vaccine, Zometa (zolendronate), IL-2, and synthesized HMBPP will be tested in vaccine trials.

Aim I. Test Vγ2Vδ2 T Cell Recognition of *F. tularensis* Infected Epithelial Cells, Monocytes, and Macrophages (a. Assess Cytolysis of Infected Cells; b. Measure IFN-γ Secretion in Response to Infected Cells; c. Assess Killing of Intracellular *F. tularensis*).

Human Vγ2Vδ2 T cell lines/clones. Approximately 30 T cell clones expressing Vγ2Vδ2 and other γδ TCR are available in the lab for these studies as aliquots of frozen cells. (See Morita, C. T., S. Verma, P. Aparicio, C. Martinez-A., H. Spits, and M. B. Brenner. 1991. Functionally distinct subsets of human γ/δ T cells. Eur. J. Immunol. 21: 2999-3007; Tanaka, Y., S. Sano, E. Nieves, G. De Libero, D. Roca, R. L. Modlin, M. B. Brenner, B. R. Bloom, and C. T. Morita. 1994. Nonpeptide ligands for human γδ T cells. Proc. Natl. Acad. Sci. USA 91: 8175-79). Short term Vγ2Vδ2 lines can also be readily made by stimulation with isopentenyl pyrophosphate or HMBPP. Primary human Vγ2Vδ2 T cells will be isolated either positive or negative magnetic bead selection by our standard techniques. First, blood αβ and γδ T cells and NK cells will be enriched using T cell enrichment columns (R & D Systems, Minneapolis, Minn.). γδ T cells will be purified by positive selection using haptenated anti-γδ mAbs and anti-hapten magnetic beads using the Miltenyi Biotec kit. γδ T cells and NK cells may also be purified by negative selection using the anti-αβ TCR mAb, BMA-031, and goat anti-mouse IgG-microbeads.

Vγ2Vδ2 T cell recognition—Cytolytic Assays. Infected cells will be tested at the peak of infection and 2 days before the peak of infection. *F. tularensis* infected- and mock-infected human cells will be labeled with $^{51}$Cr and cultured with varying numbers of Vγ2Vδ2 T cells in our standard 4 hour cytolytic assay. (See Morita et al. 1991 supra). The mitogen PHA and the nonpeptide antigen, HMBPP, will be used as positive controls.

Vγ2Vδ2 T cell recognition—IFN-γ Production. IFN-γ production in response to *F. tularensis* infected cells will be determined by measuring IFN-γ levels in the supernatant after 24-48 hours by commercial ELISA kits or by intracellular IFN-γ expression (Pharmingen) as routinely preformed in our lab. Vγ2 Vδ2 T cell recognition—Killing of intracellular and extracellular *F. tularensis*. The killing of intracellular *F. tularensis* by Vγ2Vδ2 T cells will be determined by incubating infected cells at the peak of infection and 2 days before the peak of infection with Vγ2Vδ2 T cells for 24 hours. Cells will then be washed to remove free bacteria, lysed with SDS, and CFU determined. Extracellular *F. tularensis* will be directly cultured with Vγ2Vδ2 T cells for 12-24 hours and CFU determined.

Aim II. Determine the Contribution of Vγ2Vδ2 T Cell to the Survival of huPBMC-SCID-Beige Mice Infected with *F. tularensis*

Human PBMC-SCID-beige mouse model. To determine the contribution of human Vγ2Vδ2 T cells to early immunity to *F. tularensis* in vivo, 3×10⁷ PBMC from buffy coats obtained from normal blood donors will either be incubated overnight with HMBPP or IPP to activate Vγ2Vδ2 T cells or injected directly. The cells will be injected i.p. into 5-10 SCID-beige mice followed by i.p. injection of varying numbers of *F. tularensis* LVS. After 16 hours, *F. tularensis* CFU will be determined from the peritoneal cavity, spleen, and liver. Also, expansion of Vγ2Vδ2 T cells will be assessed by flow cytometry at various time points following infection. To determine the importance of Vγ2Vδ2 T cells, Vγ2Vδ2 will be deleted using either mouse anti-human Vδ2 (BB3) or an isotype-matched control mAb (P3), and MACS anti-mouse Ig microbeads or the MACS γδ T cell microbead kit according to the manufacturer's instructions. Greater than 95% of Vγ2Vδ2 T cells can be depleted, as confirmed by surface marker staining and flow cytometry. This model system is routinely used to assess the ability of different nonpeptide antigens and mutant bacteria to activate Vγ2Vδ2 T cells. Clearly, data obtained from the human PBMC-SCID-beige mouse model will need to be interpreted cautiously because of incompatibilities between the mouse and human immune systems and possible graft versus host reactions after 2-3 months by transplanted human cells. Trafficking of human cells in the mouse may also be abnormal since some adhesion and chemokine receptors are not compatible. However, the immunodeficiency of SCID-beige mice allows engraftment of human PBMC 100% of the time and this model system is the best small animal model to study human immunity. Our preliminary data and those of others have shown it is possible to get Vγ2Vδ2 T cell responses in huPBMC-SCID-beige mice in the 1-3 week period which is well before significant graft versus host reactions. (See Malkovska et al. 1992 supra; Malkovska et al. 1994 supra; and Wang et al. 2001 supra). While not exactly recapitulating the human situation, the huPBMC-SCID-beige mouse model can provide important insights into γδ T cell functions that are pertinent to their immunity to human infections.

Aim III. Derive Live Bacterial Vaccines for Vγ2Vδ2 T Cells that Overproduce HMBPP from Attenuated *Salmonella*

Rationale: Bacteria that are used as live vaccines, including *Salmonella typhimurium/typhi, Francisella tularensis* LVS, and *Mycobacterium bovis* BCG, all use the deoxyxylulose pathway and contain lytB homologues. The process of making a bacteria avirulent appears to diminish its ability to stimulate Vγ2Vδ2 T cell responses. For example, s.c. vaccination with *Francisella* tularensis LVS or *M. bovis* BCG did not expand human Vγ2Vδ2 T cells. (See Poquet et al. supra; and Hoft, D. F., R. M. Brown, and S. T. Roodman. 1998. Bacille Calmette-Guérin vaccination enhances human γδ T cell responsiveness to mycobacteria suggestive of a memory-like phenotype. J. Immunol. 161: 1045-54). The lack of expansion by *M. bovis* BCG may be due to the fact that BCG has lower levels of phosphoantigens than other mycobacteria and that they are given in lower numbers compared with our studies using large numbers of bacteria given intravenously. (See Constant et al. supra; Shen, Y., D. Zhou, L. Qiu, X. Lai, M. Simon, L. Shen, Z. Kou, Q. Wang, L. Jiang, J. Estep, R. Hunt, M. Clagett, P. K. Sehgal, Y. Li, X. Zeng, C. T. Morita, M. B. Brenner, N. L. Letvin, and Z. W. Chen. 2002. Adaptive immune response of Vγ2Vδ2+T cells during mycobacterial infections. Science 295: 2255-8).

Derivation of attenuated *Salmonella typhimurium* and *Salmonella* strains that overproduce HMBPP by targeted deletion of the lytB gene—The lytB gene codes for the enzyme that metabolizes HMBPP to IPP and DMAPP. (See Rohdich, F., S. Hecht, K. Gartner, P. Adam, C. Krieger, S. Amslinger, D. Arigoni, A. Bacher, and W. Eisenreich. 2002. Studies on the nonmevalonate terpene biosynthetic pathway: metabolic role of IspH (LytB) protein. Proc. Natl. Acad. Sci. USA 99: 1158-63). It has been shown that deletion of lytB can increase bioactivity levels for Vγ2Vδ2 T cells up to 1,500 fold as compared with wild type bacteria. (See FIG. 3; and Eberl, M., B. Altincicek, A.-K. Kollas, S. Sanderbrand, U. Bahr, A. Reichenberg, E. Beck, D. Foster, J. Wiesner, M. Hintz, and H. Jomaa. 2002. Accumulation of a potent γδ T-cell stimulator after deletion of the lytB gene in *Escherichia coli. Immunology* 106: 200-11). HMBPP is secreted from the bacteria as evidenced by its accumulation in the culture media. A *Salmonella typhimurium* SL7207 vaccine strain having a targeted deletion in the lytB gene overproduces HMBPP (FIG. 3). This vaccine strain also has deletions in the aroA gene that makes the bacteria non-replicating in the host where it can persist for >20 days. *Salmonella typhimurium* SL7207 may be particularly useful for preparing a vaccine for activating Vγ2Vδ2 T cells in vivo because *Salmonella typhimurium* SL7207 has been used extensively for the development of human vaccines and *Salmonella typhi* Ty21a is the strain used for human immunization for typhoid fever. (See Malkovska et al. 1992 supra; and Malkovska et al. 1994 supra). These additional lytB deletion mutants will be transfected with heterologous genes encoding for enzymes of the mevalonate pathway to complement the loss of lytB. These mutants may have higher HMBPP levels and may persist longer in the host to provide an enhanced and long-lasting activation of Vγ2Vδ2 T cells.

Creation of lytB⁻ *Salmonella* mutants. A lytB deletion mutant may be constructed in the chromosome of *Salmonella* using the standard "one-step inactivation" procedure described by Datsenko and Wanner. (See Datsenko, K. A., and B. L. Wanner. 2000. One-step inactivation of chromosomal genes in *Escherichia coli* K-12 using PCR products. Proc. Natl. Acad. Sci. USA 97: 6640-5). The pTMV19km$^r$ plasmid carrying all of the mevalonate synthesis genes and ampicillin resistance (amp$^r$) will be introduced into the strains to transcomplement for the absence of the lytB gene. (See Takagi, M., T. Kuzuyama, S. Takahashi, and H. Seto. 2000. A gene cluster for the mevalonate pathway from *Streptomyces* sp. Strain CL190. J. Bacteriol. 182: 4153-7). PCR primers have been made with 50 bp of homology to the 5' and 3' ends of the lytB gene and with an additional 20 bp of homology to the plasmid template pKD3. PCR amplification with these primers will generate a 1.1 kb linear fragment encoding the chloramphenicol gene flanked by 50 bp of lytB gene homology on either end. This linear PCR fragment will be electroporated into electrocompetent *Salmonella* carrying the mevalonate synthesis plasmid and pKD46. Plasmid pKD46 encodes the λ protein γ, β, exo that protect the ends of linear DNA from degradation. Successfully transformed bacteria will be selected with chloramphenicol plus ampicillin. PCR tests on multiple independent bacterial colonies will be performed to confirm that the lytB gene is disrupted. The bacteria should also be resistant to fosmidomycin, an antibiotic that targets the dexoyxylulose pathway for IPP synthesis. The supernatants and sonicates of the mutant and wild type bacteria will be tested for antigenic activity for Vγ2Vδ2 T cells in a 12G12 Vγ2Vδ2 T cell clone proliferation assay that is standardized with IPP and ethyl-pyrophosphate control compounds. Toxicity of the attenuated bacteria will be assessed by oral inoculation of mice. Initial testing for antigenicity of the bacterial vaccines will be in the huPBMC-SCID-beige mouse model as detailed above.

Aim IV. Test HMBPP/Adjuvant Vaccines and Live Bacterial Vaccines for Their Ability to Stimulate Vγ2Vδ2 T Cells in a Primate Model (a. Determine the Ability of HMBPP Vaccines to Expand Vγ2Vδ2 T Cells In Vivo; b. Assess the Effects of HMBPP Vaccines on Vγ2Vδ2 T Cell Naïve and Memory Subsets; c. Determine the Ability of HMBPP Vaccines to Increase the Reactivity of Vγ2Vδ2 T Cells to Nonpeptide Antigens in Vitro; d. Determine the Ability of Vγ2Vδ2 T Cells to Mount Memory Responses Upon Subsequent HMBPP Vaccination in vivo)

Rationale. It has been shown that rhesus monkeys exhibit identical nonpeptide antigen responses to humans due to their strict conservation of the Vγ2Vδ2 TCR and that monkeys from closed monkey colonies have naïve Vγ2Vδ2 T cells (see id.) and may be excellent candidates to evaluate the stimulation of Vγ2Vδ2 T cells in vivo. (See Wang et al. 2003 supra). Studies of i.v. *M bovis* BCG infections provide evidence that Vγ2Vδ2 T cells develop adaptive immune responses. (See Shen et al. supra). Therefore, HMBPP/adjuvant combinations and live vaccines overproducing HMBPP will be used to vaccinate rhesus monkeys as a model system for human immunization. The adjuvants CpG and R-848 may be utilized because of the effectiveness of CpG at enhancing peptide immunization for CD8 αβ T cells in vivo. (See Vasilakos, J. P., R. M. Smith, S. J. Gibson, J. M. Lindh, L. K. Pederson, M. J. Reiter, M. H. Smith, and M. A. Tomai. 2000. Adjuvant activities of immune response modifier R-848: comparison with CpG ODN. Cell. Immunol. 204: 64-74; and Heil, F., P. Ahmad-Nejad, H. Hemmi, H. Hochrein, F. Ampenberger, T. Gellert, H. Dietrich, G. Lipford, K. Takeda, S. Akira, H. Wagner, and S. Bauer. 2003. The Toll-like receptor 7 (TLR7)-specific stimulus loxoribine uncovers a strong relationship within the TLR7, 8 and 9 subfamily. Eur. J. Immunol. 33: 2987-97). Depot adjuvants also may be utilized (e.g., Montanide ISA 720) to make a water-in-oil emulsion with nonpeptide antigen/CpG or R-848. Montanide ISA 720 has been reported to increase the effectiveness of a peptide antigen/CpG vaccine for malaria and the adjuvant is well tolerated in humans and in monkeys. (See Kumar, S., T. R. Jones, M. S. Oakley, H. Zheng, S. P. Kuppusamy, A. Taye, A. M. Krieg, A. W. Stowers, D. C. Kaslow, and S. L. Hoffman. 2004. CpG oligodeoxynucleotide and Montanide ISA 51 adjuvant combination enhanced the protective efficacy of a subunit malaria vaccine. Infect. Immun. 72: 949-57).

Figure 8:
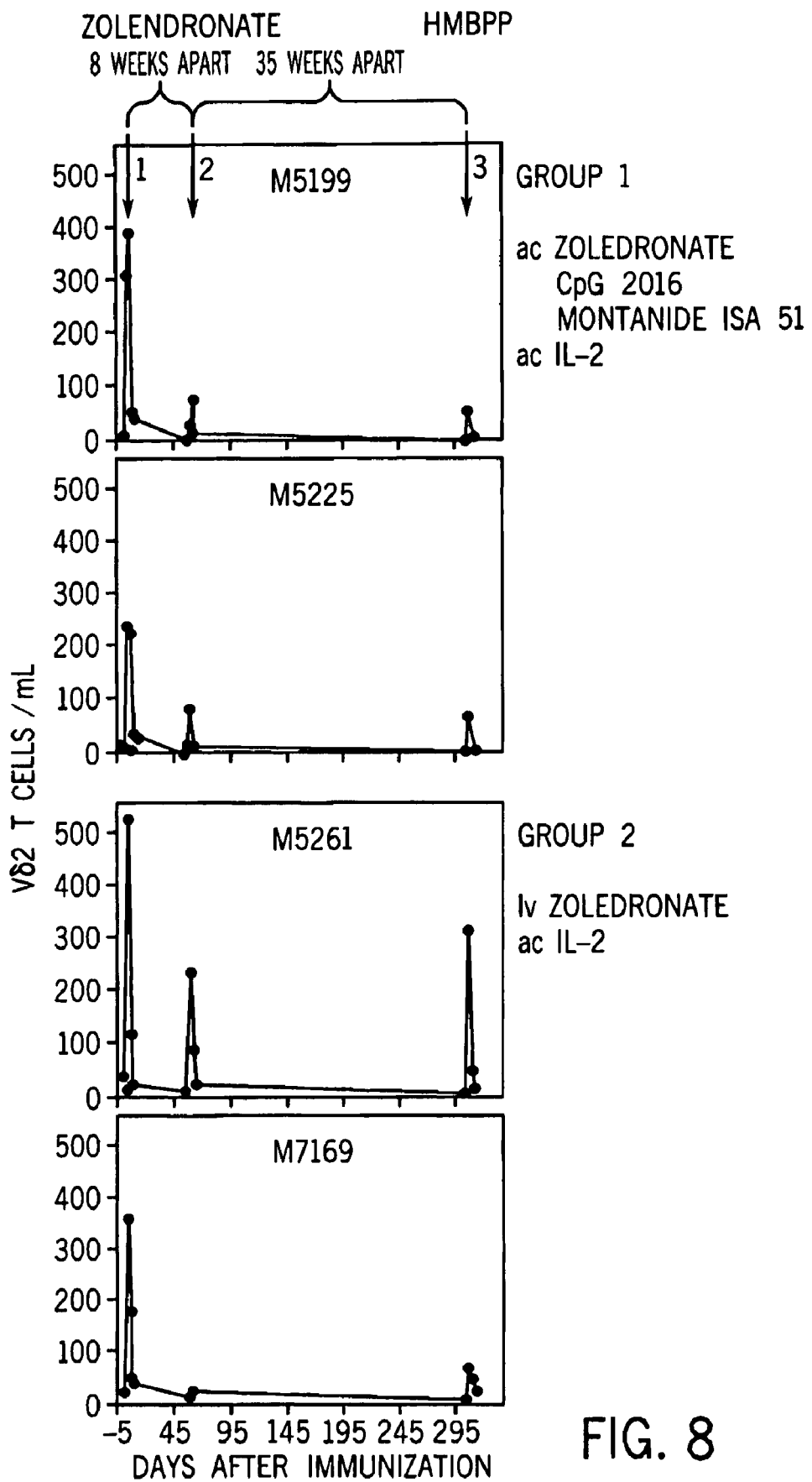
FIG. 8. Immunization with the bisphosphonate, zoledronate, and HMBPP leads to immune exhaustion. Rhesus monkeys were immunized with 0.06 mg/kg sc zoledronate with CpG in a lipid adjuvant top 2 panels) or with an equal amount of iv zoledronate (bottom 2 panels) twice, 2 months apart. Both groups were then immunized with HMBPP (70 mg/kg iv) 35 weeks later. SC IL-2 was given daily for 4 days for each immunization. Vγ2Vδ2 T cells were assessed by flow cytometry.
Figure 9:
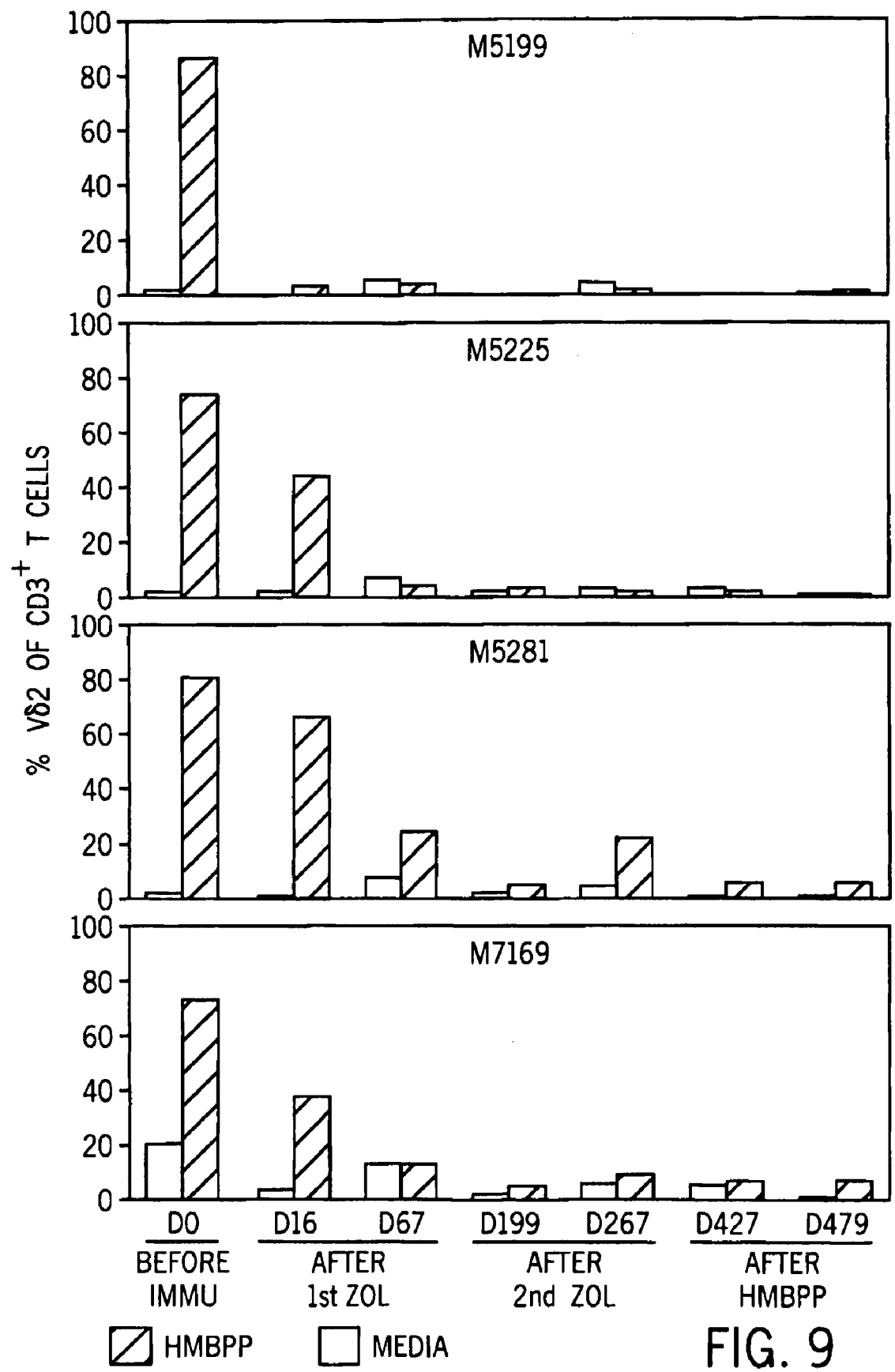
FIG. 9. Expansion of monkey Vγ2Vδ2 T cells by immunization with the bisphosphonate, zoledronate, or HMBPP given with sc IL-2 leads to loss of in vitro reactivity to HMBPP. Rhesus monkeys were immunized with 0.06 mg/kg sc zoledronate with CpG in a lipid adjuvant top 2 panels) or with an equal amount of iv zoledronate (bottom 2 panels) twice, 2 months apart, followed by HMBPP (70 mg/kg iv). SC IL-2 was given daily for 4 days for each immunization. PBMC were isolated before and ~2 weeks after each immunization. The cells were cultured with HMBPP for 9 days followed by analysis by flow cytometry.
Figure 10:
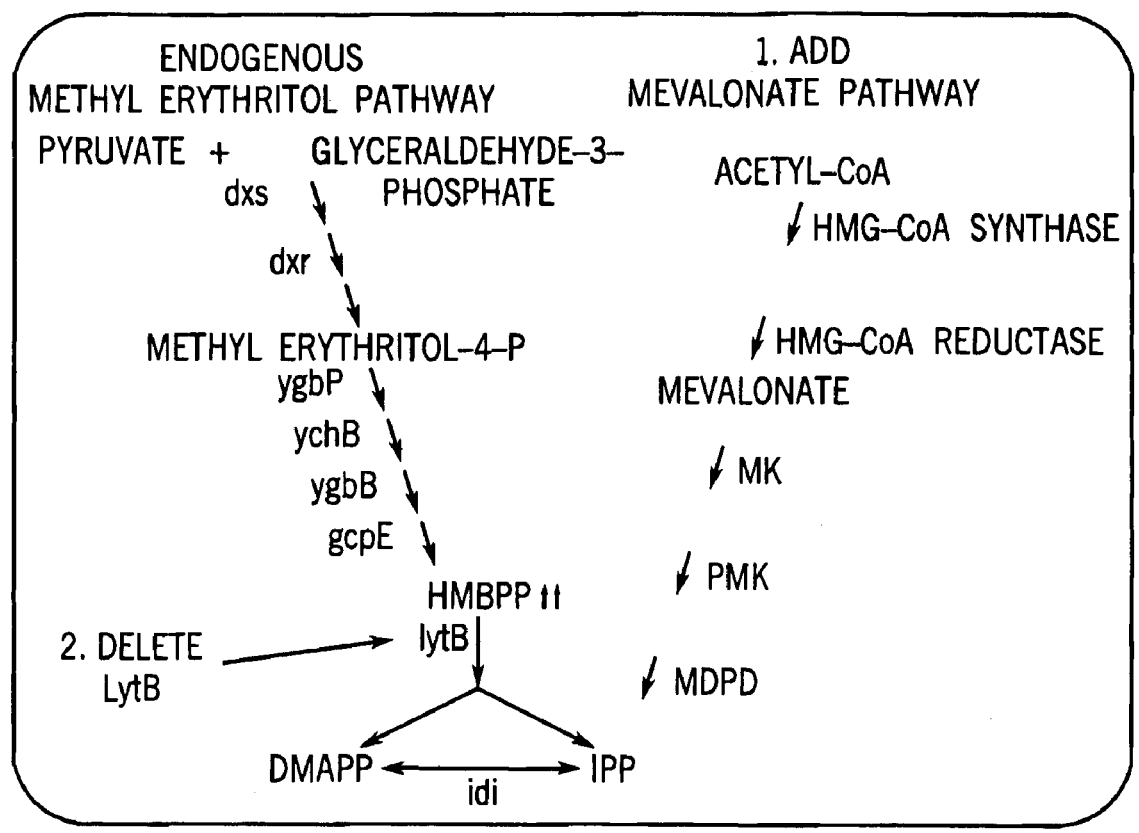
FIG. 10. Simplified schematic of the process of genetically engineering a microbe to overproduce HMBPP by complementation with the mevalonate pathway and deletion of lytB.
Figure 11:
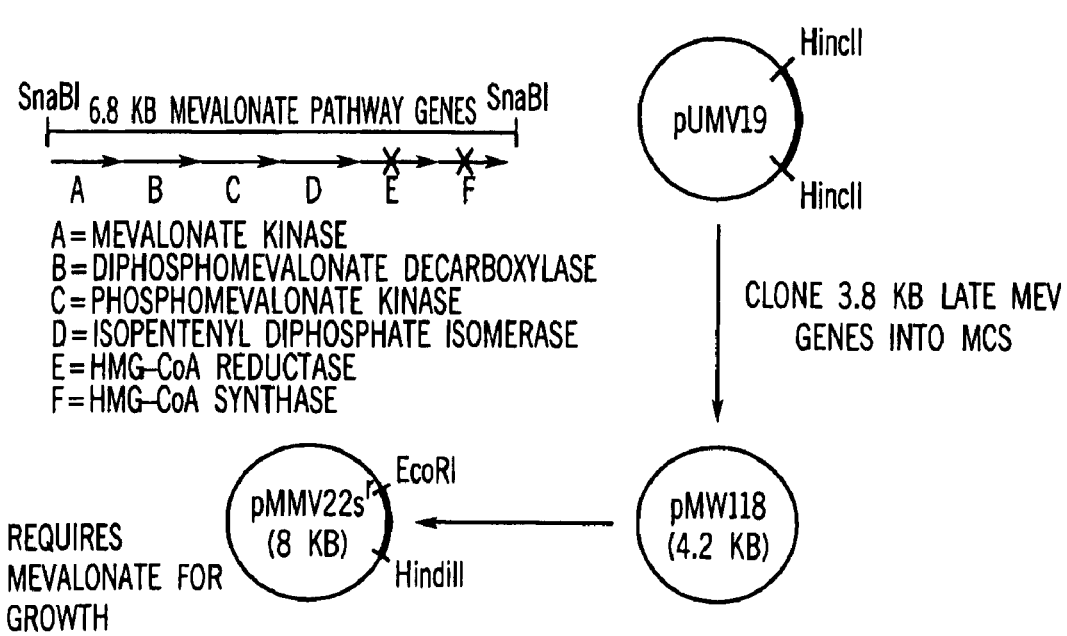
FIG. 11. Cloning scheme for creating pMMV22spec$^r$ based on low copy number plasmid pMW118. The four mevalonate pathway genes were derived from *Streptomyces* sp. strain CL190.

Current trials of nonpeptide antigens by Innate Pharma in monkeys and in human subjects with B cell malignancies have focused on giving phosphoantigens (Phosphostim) or the bisphosphonates, pamidronate or zoledronate, intravenously with or without IL-2. (See Wilhelm, M., V. Kunzmann, S. Eckstein, P. Reimer, F. Weissinger, T. Ruediger, and H.-P. Tony. 2003. γδ T cells for immune therapy of patients with lymphoid malignancies. Blood 102: 200-6; Dieli, F., N. Gebbia, F. Poccia, N. Caccamo, C. Montesano, F. Fulfaro, C. Arcara, M. R. Valerio, S. Meraviglia, C. Di Sano, G. Sireci, and A. Salerno. 2003. Induction of γδ T-lymphocyte effector functions by bisphosphonate zoledronic acid in cancer patients in vivo. Blood 102: 2310-1; and data not shown). Although such immunizations when given with IL-2, do result in Vγ2Vδ2 T cell expansions (sometimes to high levels), these immunizations are limited in that repeated immunization under these conditions results in anergy or deletion of Vγ2Vδ2 T cells. Intravenous immunization without IL-2 generally does not result in Vγ2Vδ2 T cells expansion beyond 1 immunization. (See Wilhelm et al. supra; and Dieli et al. supra). Instead, there was an increase in IFN-γ production that reflected the increasing differentiation to effector CD45RA$^+$ memory cells. We found similar findings with intravenous immunization with zoledronate in monkeys (FIG. 8) with increased differentiations to effector memory cells (data not shown) and loss of in vivo (FIG. 8) and in vitro proliferation by Vγ2Vδ2 T cells to antigenic stimulation (FIG. 9).

HMBPP is similar to peptides recognized by CD8 αβ T cells since peptides do not require processing or internalization and act on a T cell population that needs CD4 T cell help for efficient activation and expansion. If given alone, peptides for CD8 αβ T cells are poorly immunogenic probably because they do not activate CD4 T cells or innate immune cells. Because our initial trial with CpG 2016 in Montanide ISA 54 did not demonstrate adequate adjuvant activity, we will infect monkeys with the live lytB$^-$ *Salmonella* vaccine by intranasal instillation. For our initial studies, we will use the present lytB$^-$ *Salmonella enterica* Serovar *Typhimurium* strain that we have generated. We would predict later peak responses and less loss of reactivity on subsequent immunizations.

Adjuvants from GlaxoSmithKline (GSK) will be utilized. GSK has developed new immunostimulatory adjuvants, AS021/AS02, for use in humans. These adjuvants are formulated to give strong T cell responses. (See Pinder, M., W. H. Reece, M. Plebanski, P. Akinwunmi, K. L. Flanagan, E. A. Lee, T. Doherty, P. Milligan, A. Jaye, N. Tornieporth, R. Ballou, K. P. McAdam, J. Cohen, and A. V. Hill. 2004. Cellular immunity induced by the recombinant *Plasmodium falciparum* malaria vaccine, RTS,S/AS02, in semi-immune adults in The Gambia. Clin. Exp. Immunol. 135: 286-93). These adjuvants will be combined with QS-21 (a saponin from *Quillaya saponaria*), with the TLR4 ligand, and monophosphoryl lipid A, in a lipid or liposomal carrier. We propose to test these adjuvants with HMBPP in our monkey model. We will also try adding CpG to the AS02 adjuvant as is currently being tested for other vaccines. R-848 is very similar to CpG in its effects in mice so this will also be tried.

As an alternative approach to preserve early memory Vγ2Vδ2 T cells after immunization with HMBPP, we will try varying the γ$_C$ cytokine from IL-2 to IL15. IL-15 has been reported to enhance in vivo activity of murine anti-tumor T cells, improve survival of the murine CD8 αβ memory cell pool, and induce primate CD4 and CD8 αβ effector memory cells to proliferate and emigrate into tissues much more efficiently than IL-2. (See Klebanoff, C. A., S. E. Finkelstein, D. R. Surman, M. K. Lichtman, L. Gattinoni, M. R. Theoret, N. Grewal, P. J. Spiess, P. A. Antony, D. C. Palmer, Y. Tagaya, S. A. Rosenberg, T. A. Waldmann, and N. P. Restifo. 2004. IL-15 enhances the in vivo antitumor activity of tumor-reactive CD8$^+$ T cells. Proc. Natl. Acad. Sci. USA 101: 1969-74; Melchionda, F., T. J. Fry, M. J. Milliron, M. A. McKirdy, Y. Tagaya, and C. L. Mackall. 2005. Adjuvant IL-7 or IL-15 overcomes immunodominance and improves survival of the CD8$^+$ memory cell pool. J. Clin. Invest. 115: 1177-87; and Picker, L. J., E. F. Reed-Inderbitzin, S. I. Hagen, J. B. Edgar, S. G. Hansen, A. Legasse, S. Planer, M. Piatak, Jr., J. D. Lifson, V. C. Maino, M. K. Axthelm, and F. Villinger. 2006. IL-15 induces CD4 effector memory T cell production and tissue emigration in nonhuman primates. J. Clin. Invest. 116: 1514-24). We had earlier showed that IL-15 enhanced Vγ2Vδ2 T cell responses to prenyl pyrophosphates in vitro by activation of STAT1. (See García, V. E., D. Jullien, M. Song, K. Uyemura, K. Shuai, C. T. Morita, and R. L. Modlin. 1998. IL-15 enhances the response of human γδ T cell responses to nonpeptide microbial antigens. J. Immunol. 160: 4322-9). Since we have also found that resting Vγ2Vδ2 T cell respond to IL-15 in vitro, we tested the ability of human memory Vγ2Vδ2 T cells to respond in vivo in the huPBMC-SCID-beige mouse model. IL-15 was able to support homeostatic expansion of Vγ2Vδ2 T cells in the absence of antigen and higher levels of expansion of Vγ2Vδ2 T cells with HMBPP compared with IL-2 and IL-7 (data not shown). These results suggest IL-15 would be superior to IL-2 in maintaining and expanding Vγ2Vδ2 T cells. Thus, in this study, immunostimulatory adjuvants (e.g., subcutaneously) or live bacterial vaccines (e.g., intranasally or orally) will be administered to stimulate Vγ2Vδ2 T cells under conditions that are more physiologic and that preferably will retain central memory Vγ2Vδ2 T cells and provide a long-lasting Vγ2Vδ2 T cell activation response.

Testing HMBPP Vaccines: Preliminary testing of vaccines in huPBMC-SCID-beige mice for toxicity and immunogenicity will be done prior to their use in monkeys. To evaluate vaccine effectiveness, normal rhesus monkeys to be immunized will have blood drawn before and at various times (2-3 times per week) after immunization. Blood will be analyzed for:

1. Levels of γd T cells and their V gene expression. The γδ T cells for each monkey will be characterized with available monoclonal antibodies that have been found to react with rhesus monkey γδ, Vδ1, Vδ2, Vδ2, Vγ1.2, 1.3 1.4, Vγ1.4, Vγ1.8, Vγ2 TCR, (See Wang et al. 2003 supra; and Shen et al. supra).

2. Vγ2Vδ2 Memory T cell subsets. The Vγ2Vδ2 T cells will be analyzed with mAbs to the memory markers, CD27 (M-T271), CD28 (CD28.2), CD45RA (5H9), and CD62L (SK11) in addition to a panel of 14 chemokine receptors that react with rhesus monkeys cells by 3- and 4-color FACS. (See Pharmingen protocol; and Pitcher, C. J., S. I. Hagen, J. M. Walker, R. Lum, B. L. Mitchell, V. C. Maino, M. K. Axthelm, and L. J. Picker. 2002. Development and homeostasis of T cell memory in rhesus macaque. *J. Immunol.* 168: 29-43). It has been found that Vγ2Vδ2 T cell levels and memory subset distribution are stable in humans for several years with only minor variations so the preimmunization values of each monkey will serve as controls for immunization effectiveness.

3. Responsiveness to HMBPP. (A) Vγ2Vδ2 Expansion—PBMC will be stimulated with HMBPP in vitro for 9 days followed by cell counting and FACS analysis to measure Vγ2Vδ2 T cell expansion. (B) Production of IFN-γ and TNF-α—will be measured by staining for intracytoplasmic cytokines after stimulation with HMBPP. (C) Level of IFN-γ and TNF-α secretion—Vγ2Vδ2 T cells will be stimulated by HMBPP and IFN-γ and TNF-α supernatant levels will be determined by ELISA kits.

Dose of HMBPP Vaccines: HMBPP stimulates ½ max proliferation of Vγ2Vδ2 T cells at ~30 pM in vitro. The total weight of rhesus monkeys is approximately 5-12 kg depending on age and sex. Each monkey will be adminstered 100 μg/kg since this would give 382 nmoles/kg or 10,000× the ½ max dose if the HMBPP was in liquid. HMBPP will be provided as previously reported. (See Giner, J.-L. 2002. A convenient synthesis of (E)-4-hydroxy-3-methyl-2-butenyl pyrophosphate and its [4-13C]-labeled form. Tetrahedron Lett. 43: 5457-9). CpG adjuvant will be ODN2216 that has been used in primates and in humans and has been obtained from Dr. Art Krieg, Coley Pharmaceutical Group. R848 has been obtained from 3-M Pharmaceuticals for these studies. HMBPP will be administered as a water-in-oil emulsion with Montanide ISA 720 from Seppic, Inc to provide a depot effect. This adjuvant has already been used with monkeys and humans. HMBPP/adjuvant/oil will given at a total final volume of 500 μl injected subcutaneously (s.c.) at 4 sites in the shaved back of the monkeys. *Salmonella* vaccine will be given intranasally or orally at the standard dose either as 1 dose for SL7207 or 4 doses 48 h apart for Ty21a.

1. Pilot vaccine testing: For pilot testing 2-4 rhesus monkeys per group will be immunized with HMBPP/CpG, HMBPP/R848, and the live *Salmonella* vaccine (see above for doses). γδ T cells from each monkey will be analyzed as detailed above prior to and following immunization. Expansion of Vγ2Vδ2 T cells, change in memory subset proportions, or increased reactivity to nonpeptide antigens in vitro are potential results that would indicate successful immunization.

2. Testing whether Vγ2 Vδ2 T cell responses are innate or adaptive. To answer the question of whether Vγ2Vδ2 T cells mount innate or adaptive immune responses, monkeys that show initial responses to one or more HMBPP vaccines described above will be rechallenged 2 months after primary immunization with the same vaccine. If the response is greater, this would suggest that HMBPP immunization alone or as a prime-boost combination will increase Vγ2Vδ2 T cell function. If there is no increase, this could indicate that the benefit of these vaccines would be more as an adjuvant to augment the immunogenicity of other antigens.

3. Dose escalation trials: Based on the results of the initial vaccinations, a vaccine that elicits the strongest response will be selected. A dose escalation trial using this selected vaccine will then be performed to determine the optimal amounts of the vaccine to give and to determine if there is any toxicity. Three groups of monkeys (3 individuals/group) will be immunized with HMBPP at 100 μg/kg, 400 μg/kg, and 1600 μg/kg. Blood will be drawn as in experiment 1. If the live vaccines are the strongest vaccines, the inoculum may be varied by 3 fold for 1 dose for *Salmonella typhimurium* SL7207 lytB⁻ or for multiple oral doses separated by 2 days for *Salmonella typhi* Ty21a lytB⁻.

4. Alter $\gamma_C$ cytokine from IL-2 to IL-15: Previous i.v. immunization of humans with the bisphosphonates, pamidronate and zoledronate, and of monkeys with Phosphostim (bromohydrin-pyrophosphate) were given with IL-2 as a source of T cell growth factor. Vγ2Vδ2 T cell responses to pure nonpeptide antigens (as opposed to bacterial lysates that contain TLR ligands) are dependent on exogenous growth factors such as IL-2, IL-7, IL-15, or IL-21 because γδ T cells are poor producers of IL-2. (See Wesch, D., S. Marx, and D. Kabelitz. 1997. Comparative analysis of αβ and γδ T cell activation by *Mycobacterium tuberculosis* and isopentenyl pyrophosphate. *Eur. J. Immunol.* 27: 952-6; Marx, S., D. Wesch, and D. Kabelitz. 1997. Activation of human γδ T cells by *Mycobacterium tuberculosis* and Daudi lymphoma cells—Differential regulatory effect of IL-10 and IL-12. *J. Immunol.* 158: 2842-8; and unpublished results). IL-15 is reported to be qualitatively different than IL-2 in that it supports the proliferation and survival of memory T cells. We previously reported that IL-15 greatly enhances the expansion and IFN-γ secretion of Vγ2Vδ2 T cells in vitro (see García et al. supra) and have now found that the majority of adult Vγ2Vδ2 T cells are memory cells that respond better with IL-15 in the hu-PBMC-SCID-beige mouse model. For these experiments, 3 monkeys will be immunized with HMBPP/adjuvant substituting IL-15 for the standard IL-2. We predict that the use of IL-15 will preserve Vγ2Vδ2 T cell responsiveness because they will not be deleted as in repeated intravenous immunizations. If we see positive effects of IL-15 in vitro, we will pursue studies examining coadministration of DNA vaccines encoding IL-15 since this has been reported to enhance CD8 αβ T cell responses in monkeys infected with SIV. (See Calarota, S. A., M. Otero, K. Hermanstayne, M. Lewis, M. Rosati, B. K. Felber, G. N. Pavlakis, J. D. Boyer, and D. B. Weiner. 2003. Use of interleukin 15 to enhance interferon-γ production by antigen-specific stimulated lymphocytes from rhesus macaques. *J. Immunol. Methods* 279: 55-67).

Example 2

Construction of Recombinant Attenuated Microbes that Overproduce HMBPP

Construction and Characterization of the *Salmonella enterica* Serovar *Typhimurium* SL7207 lytB-cam pMMV22 spec$^r$ Strain.

FIG. 10 provides a general scheme for engineering *Salmonella* or other bacteria to overproduce HMBPP by complementation with the mevalonate pathway and deletion of lytB. The plasmid pMMV22spec$^r$ was constructed as indicated in FIG. 11 based on the low copy number plasmid pMW118. As indicated, the plasmid pMMV22spec$^r$ includes the genes encoding for mevalonate kinase, diphosphomevalonate decarboxylase, phosphomevalonate kinase, and isopentenyl diphosphate isomerase, which are derived from *Streptomyces* sp. Strain CL190. As discussed in Example 1, *S. Typhimurium* SL7207 was used as the starting strain for the construction because it is a vaccine strain with a mutation in aromatic amino acid biosynthesis. However, other microbes can and have been utilized such as *Shigella* spp., *Vibrio* spp., *M. Bovis* BCG, and other vaccine strains of microbes that use the deoxyxylulose pathway for IPP synthesis. The plasmid pMMV22spec$^r$ was electroporated into this strain and selected by growth for spectinomycin resistance which is present on the plasmid. (See general scheme in FIG. 12). A temperature-sensitive plasmid, pKD46, encoding the lambda exo beta, gamma genes that facilitate recombination of linear DNA was next electroporated into *S. Typhimurium* SL7207 pMMV22spec$^r$. Transformants were selected for growth in the presence of ampicillin where the gene for ampicillin resistance is present on the plasmid pKD46.

The selected *S. Typhimurium* SL7207 pMMV22spec$^r$ pKD46 strain was then used as a recipient for electroporation with a PCR fragment that encoded the gene for chloramphenicol resistance and was flanked by 50 bp of DNA from the 5' end of the lytB gene on one end and was flanked by 50 bp of DNA from the 3' end of the lytB gene on the other end. (See general schemed in FIG. 12). Electroporation of ~1-2 µg of this PCR DNA yielded 1 colony that grew on L agar supplemented with chloramphenicol 25 µg/ml and spectinomycin 50 µg/ml and 50 µg/ml of mevalonic acid. This one colony was characterized preliminarily and found to require mevalonic acid for growth. Subsequently, it was found to have the expected phenotype of a lytB mutant where the PCR DNA had recombined with the endogenous lytB gene to create a deletion of a portion of the endogenous lytB gene and an insertion of the gene for chloramphenicol resistance within the endogenous lytB gene.

Deletion of lytB in the *Salmonella enterica* serovar *Typhimurium* vaccine strain SL7207 complemented by the mevalonate pathway leads to very high levels of intracellular HMBPP as compared with LytB. (See FIG. 13). Bioactivity levels were 7.2 fold higher than those achieved with complementation with inducible LytB. 1 unit/ml is equivalent to 6 pM HMBPP.

A live bacterial vaccine was tested in SCID-beige mice xenotransplanted with human peripheral blood mononuclear cells. (See general scheme in FIG. 14). SCID-beige mice were reconstituted with $3\times10^7$ PBMC i.p. and challenged with $7.5\times10^5$ or $2.6\times10^6$ lytB- *Salmonella*. On d9 the peritoneum was lavaged and Vγ2Vδ2 T cells determined by flow cytometry. Immunization by lytB- *Salmonella enterica* serovar Typhimurium vaccine strain SL7207 complemented by the mevalonate pathway led to expansion of Vγ2Vδ2 T cells in huPBL-SCID-beige mice. (See FIG. 15).

Construction of the *Salmonella enterica* Serovar *Typhimurium* SL 7207 lytB-cam pMMV19km$^r$ Strain and the *Salmonella enterica* Serovar *Typhimurium* SL 7207 lytB-cam pTMV19km$^r$ Strain.

The plasmid pMMV19km$^r$ was constructed as indicated in FIG. 16 based on the low copy number plasmid pMW118. As indicated, the plasmid pMMV19km$^r$ includes the genes encoding for mevalonate kinase, diphosphomevalonate decarboxylase, phosphomevalonate kinase, isopentenyl diphosphate isomerase, HMG-CoA reductase, and HMG-CoA synthase, which are derived from *Streptomyces* sp. Strain CL190.

The plasmid pTMV19km$^r$ was constructed as indicated in FIG. 17 based on the high copy number plasmid pTTQ18. As indicated, the plasmid pTMV19km$^r$ includes the genes encoding for mevalonate kinase, diphosphomevalonate decarboxylase, phosphomevalonate kinase, isopentenyl diphosphate isomerase, HMG-CoA reductase, and HMG-CoA synthase, which are derived from *Streptomyces* sp. Strain CL190.

The plasmid pMMV19km$^r$ or pTMV19km$^r$ were electroporated into *S. Typhimurium* SL7207. (See FIG. 12). As discussed above, *S. Typhimurium* SL7207 was used as the starting strain for the construction because it is a vaccine strain with a mutation in aromatic amino acid biosynthesis. However, other microbes can and have been utilized such as *Shigella* spp., *Vibrio* spp., *M. Bovis* BCG, and other vaccine strains of microbes that use the deoxyxylulose pathway for IPP synthesis. Transformants were selected for growth in the presence of kanamycin where the gene for kanamycin resistance is present on the plasmid. Next, a temperature-sensitive plasmid, pKD46, encoding the lambda exo beta, gamma genes that facilitate recombination of linear DNA was electroporated into the *S. Typhimurium* SL7207 recombinant. Transformants were selected for growth in the presence of ampicillin where the gene for ampicillin resistance is present on the plasmid pKD46.

The double transformants then were used as a recipient for electroporation with a PCR fragment that encoded the gene for chloramphenicol resistance and was flanked by 50 bp of DNA from the 5' end of the lytB gene on one end and was flanked by 50 bp of DNA from the 3' end of the lytB gene on the other end. (See FIG. 12). Colonies were selected based on growth on agar supplemented with fosmidomycin that blocks the MEP pathway and switches the bacterial isoprenoid metabolism from MEP to the mevalonate pathway), kanamycin, and ampicillin. Next, arabinose was added to induce the recombinases followed by introduction of the lytB targeting PCT fragment. Chloramphenicol then was utilized to select for recombinants. Selected colonies subsequently were found to have the expected phenotype of a lytB mutant where the PCR DNA had recombined with the endogenous lytB gene to create a deletion of a portion of the endogenous lytB gene and an insertion of the gene for chloramphenicol resistance within the endogenous lytB gene. (See FIG. 18). The resulting clones were tested for antibiotic resistance, growth rate, and bioactivity for Vγ2Vδ2 T cells.

Characteristics of lytB- Deletion Mutants of *Salmonella enterica* Serovar *Typhimurium* Strain SL7207 Complemented with the pTMV19km$^r$ Plasmid Containing the Full Mevalonate Pathway.

Mutant and wild type bacteria were grown overnight and then diluted into LB media. (See FIG. 19). OD600 absorbance was measured over 96 hours. The mutant bacteria did not require mevalonate for growth and grew at essentially identical rates as the wild type bacteria suggesting that they are not overly attenuated for use as live vaccination.

Assessing Vaccine Bacteria for Biological Activity for Vγ2V 2 T Cells.

The biological activity of vaccine bacteria for Vγ2Vδ2 T cells is assessed by performing the following steps: (a) Grow bacteria to stationary phase; (b) Harvest bacteria and culture supernatants; (c) Sonicate bacteria (1 L bacteria/10 ml); (d) Heat sonicates and supernatants for 5 min in boiling water bath; (e) Centrifuge on microfuge; (f) Filter sterilize; (g) Test sonicates and supernatants for stimulation of proliferation of a Vγ2Vδ2 T cell clone using Va2 APC; and (h) Standardize bioactivity units using the control antigens, IPP, HMBPP, and monoethyl pyrophosphate. The lytB- mutant bacteria were observed to have greatly increased biological activity for Vγ2Vδ2 T cells. (See FIG. 20).

Vaccine candidates may be further tested in monkeys. For example, vaccine candidates may be assessed for their ability to stimulate δγ T cells in vivo by introducing live bacteria to rhesus monkeys (e.g., intranasally or orally).

Example 3

Preferential Recognition of a Microbial Metabolite by Human Vγ2Vδ2 T Cells

Reference is made to Puan et al., "Preferential recognition of a microbial metabolite by human Vγ2Vδ2 T cells," International Immunology 2007, available on-line on Feb. 2, 2007, and incorporated herein by reference in its entirety. Reference is made to FIGS. 21-26.

Introduction

Vγ2Vδ2 T cells are a unique subset of human T lymphocytes comprising 1-4% of total adult peripheral blood T cells (1, 2). They expand during a variety of prokaryotic and eukaryotic protozoan infections such as tuberculosis (3-5), leprosy (6), typhoid fever (7), brucellosis (8), tularemia (9-11), ehrlichiosis (12), malaria (13, 14), and toxoplasmosis (15). Studies in a human peripheral blood lymphocyte-SCID mouse model (hu-PBL-SCID) demonstrated that Vγ2Vδ2 T cells help provide immunity against *Escherichia coli, Morganella morganii,* and *Staphylococcus aureus* infections (16). Moreover, using rhesus monkeys, it was shown that Vγ2Vδ2 T cells expand during resolution of *M. tuberculosis* and *M. bovis* BCG infections, suggesting that γδ T cells also play a role in immunity against mycobacteria (17).

Figure 12:
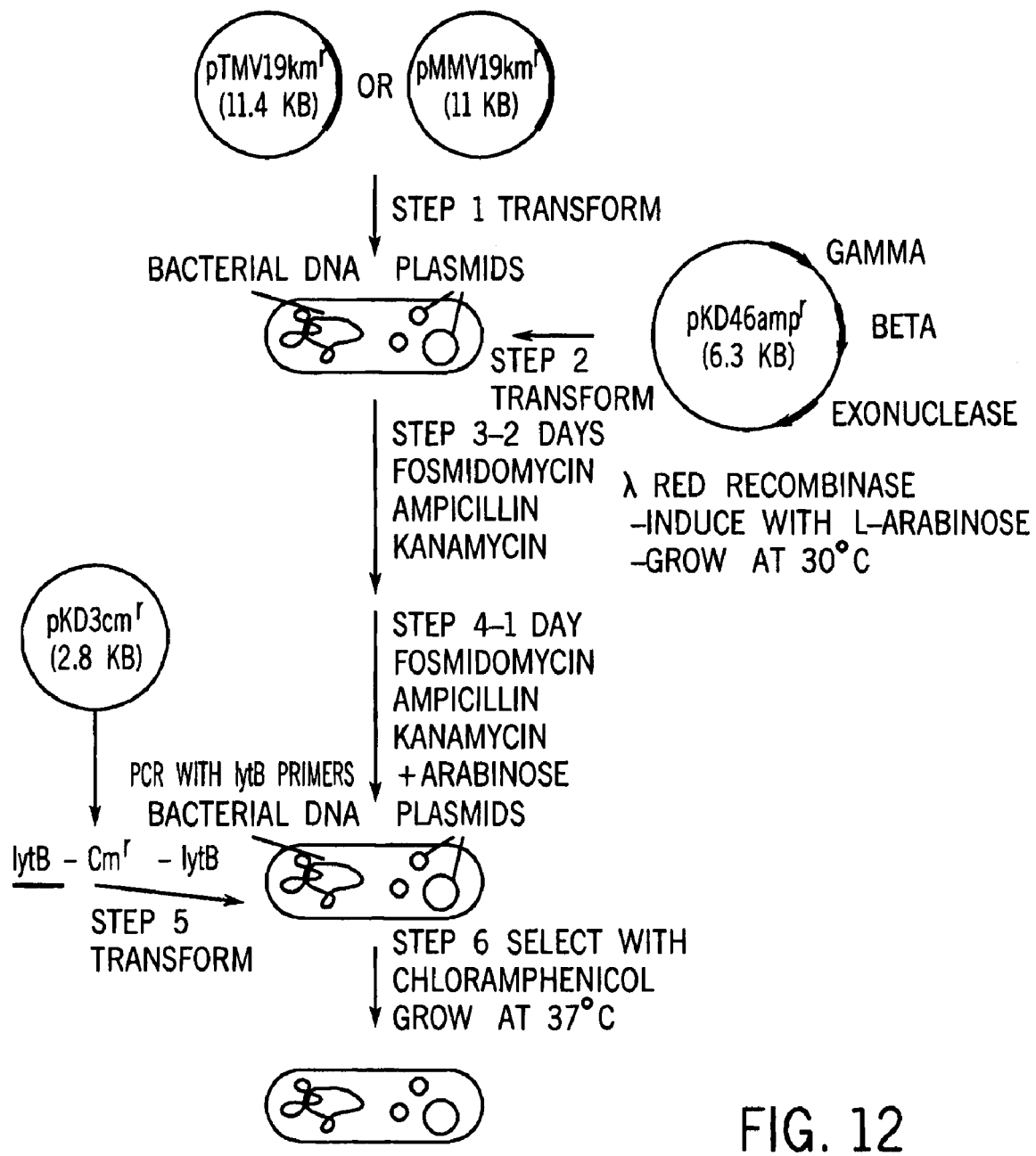
FIG. 12. General scheme for the deletion of the lytB gene for generation of live bacterial vaccines for human Vγ2Vδ2 T cells. Enzymes of the mevalonate pathway from *Streptomyces* sp. strain CL190 were cloned into the pTTQ18 or pMW119 plasmids and used to complement for the lose of the LytB gene in *Salmonella*, *Shigella*, *Vibrio*, *M. bovis* BCG, and other vaccine strains of bacteria that use the deoxyxylulose pathway for IPP synthesis. After transformation of complementing plasmids, the pKD46 ampr was transformed. Bacteria were then grown with fosmidomycin that blocks the MEP pathway (to switch the bacterial isoprenoid metabolism from MEP to the mevalonate pathway), ampicillin (for retention of the recombinase enzymes,) and kanamycin (for retention of the mevalonate pathway plasmid). Next, arabinose was added to induce the recombinases followed by introduction of the lytB targeting construct. Chlorampenicol was used to select for lytB deletion mutants. The resulting clones were tested for antibiotic resistance, growth rate, and bioactivity for Vγ2Vδ2 T cells.
Figure 13:
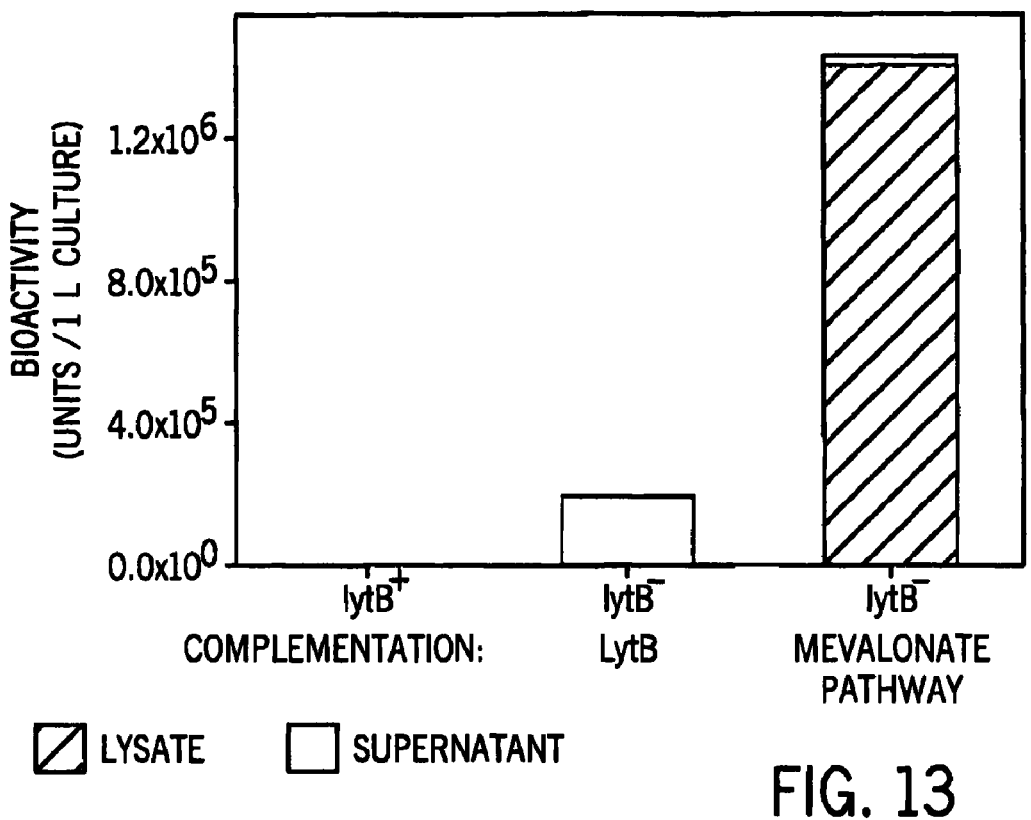
FIG. 13. Deletion of lytB in the *Salmonella enterica* serovar *Typhimurium* vaccine strain SL7207 complemented by the mevalonate pathway leads to very high levels of intracellular HMBPP as compared with LytB. Bioactivity levels were 7.2 fold higher than those achieved with complementation with inducible LytB. 1 unit/ml is equivalent to 6 pM HMBPP.
Figure 14:
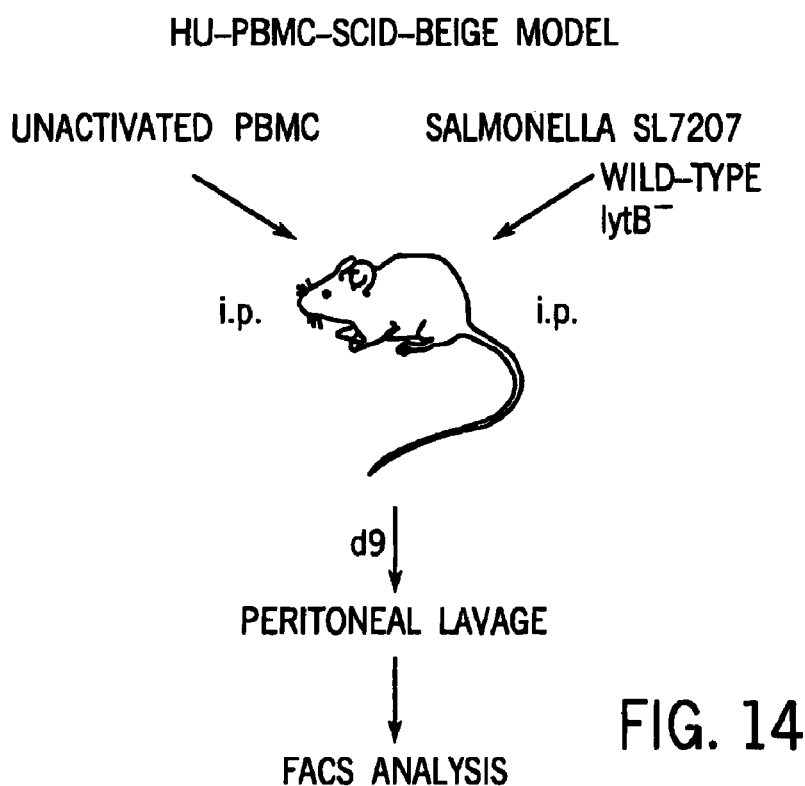
FIG. 14. General scheme for testing live bacterial vaccine in SCID-beige mice xenotransplanted with human peripheral blood mononuclear cells. SCID-beige mice are reconstituted with $3$-$5 \times 10^7$ PBMC i.p. and immunized with varying numbers of lytB-*Salmonella*. On d9 the peritoneum is lavaged and Vγ2Vδ2 T cells determined by flow cytometry.
Figure 15:
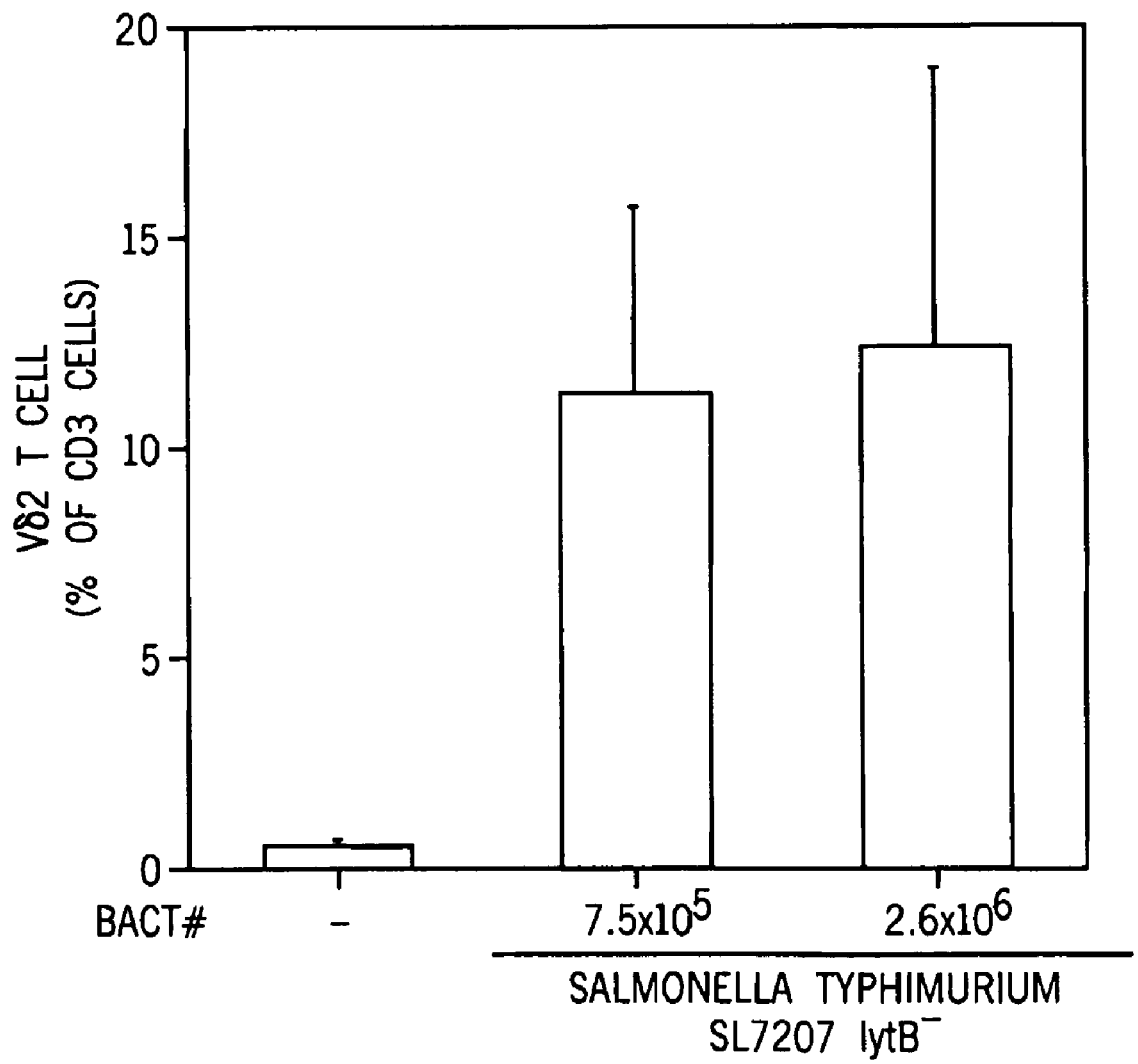
FIG. 15. Immunization by lytB- *Salmonella enterica* serovar *Typhimurium* vaccine strain SL7207 complemented by the mevalonate pathway leads to expansion of Vγ2Vδ2 T cells in huPBL-SCID-beige mice. SCID-beige mice were reconstituted with $3 \times 10^7$ PBMC i.p. and challenged with $7.5 \times 10^5$ or 2.6×10⁶ lytB-*Salmonella*. On d9 the peritoneum was lavaged and Vγ2Vδ2 T cells determined by flow cytometry.
Figure 16:
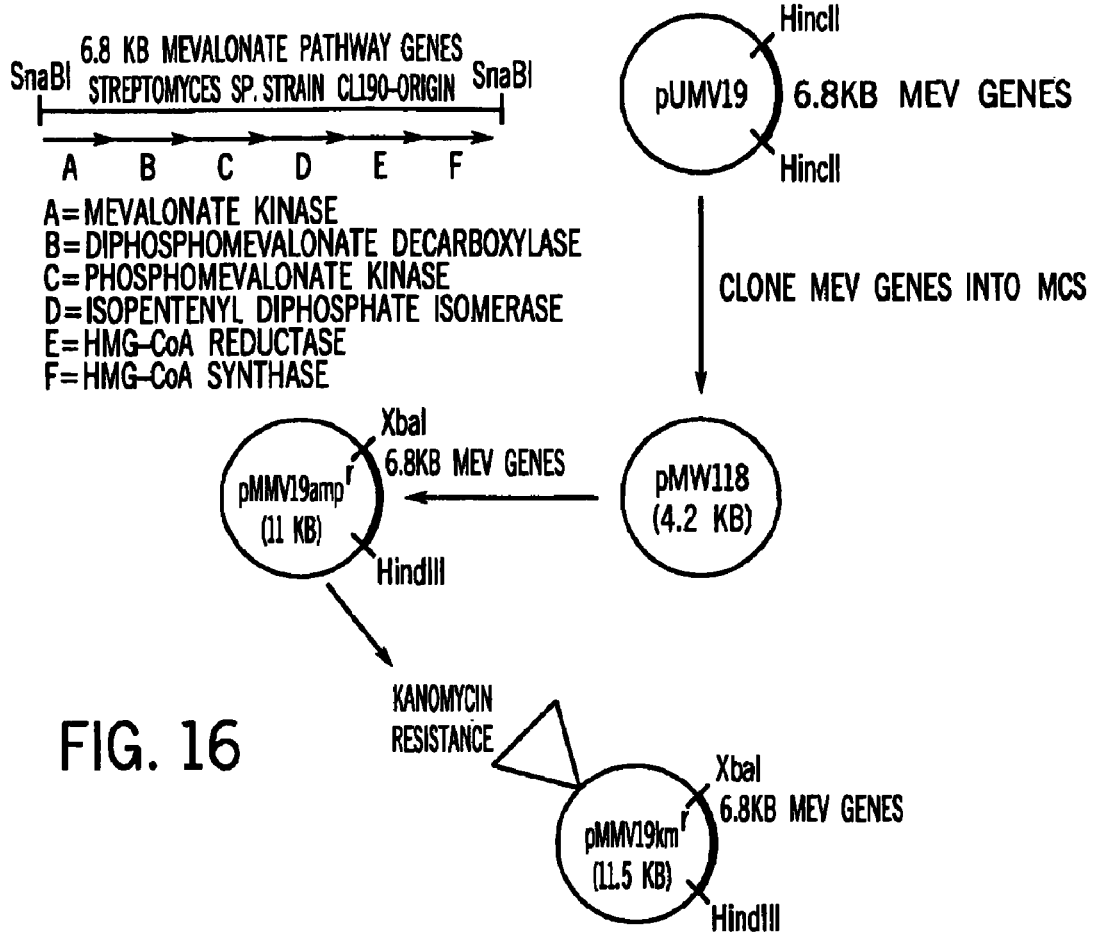
FIG. 16. Cloning scheme for creating pMMV19km$^r$ based on low copy number plasmid pMW118. The six mevalonate pathway genes were derived from *Streptomyces* sp. strain CL190.
Figure 17:
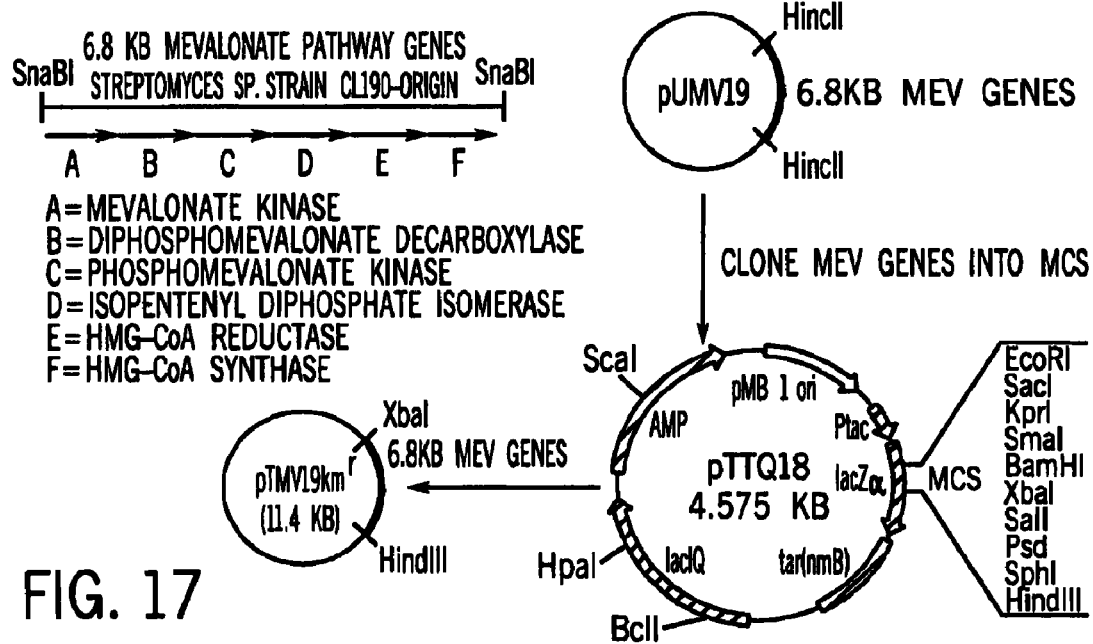
FIG. 17. Cloning scheme for creating pTMV19km$^r$ based on high copy number plasmid pTTQ18. The six mevalonate pathway genes were derived from *Streptomyces* sp. strain CL190.
Figure 18:
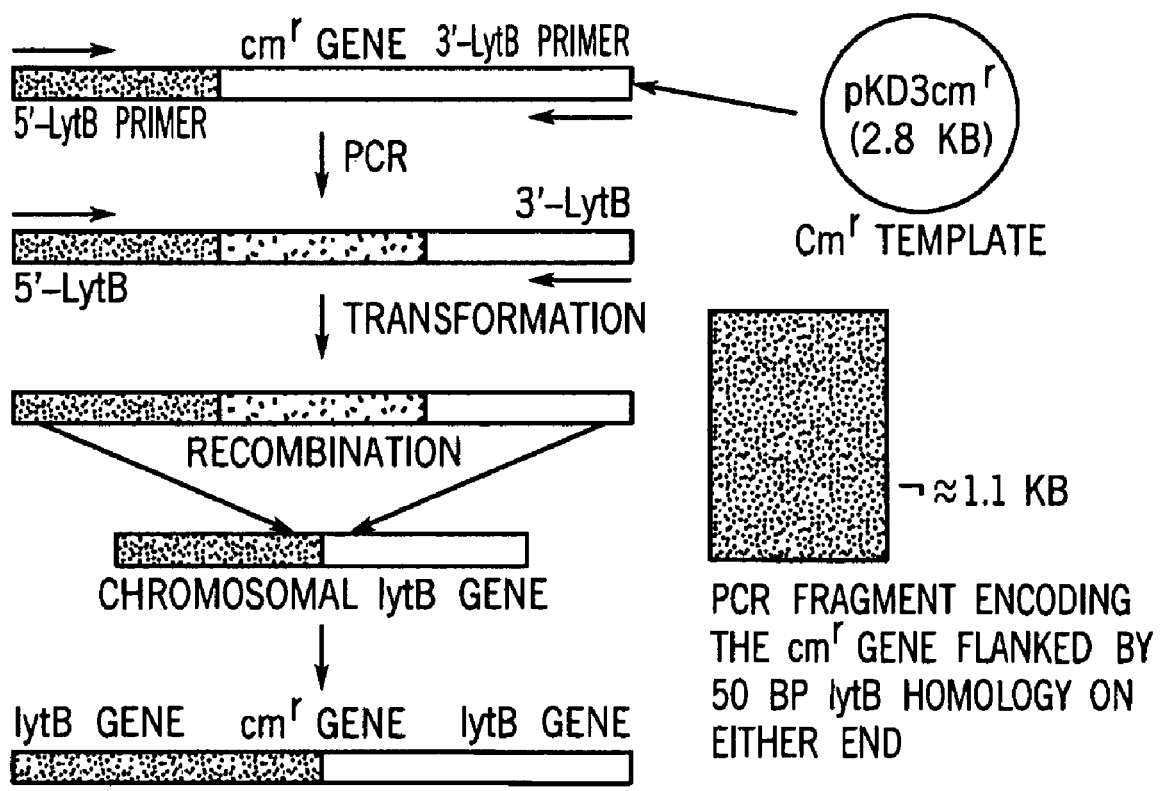
FIG. 18. Deletion of the lytB gene by homologous recombination using λ red recombinase. LytB/cm primers were used in PCR to amplify the chloramphenicol resistance gene from the pKD3cmr plasmid as indicated in FIG. 12. The resulting lytB targeting construct (i.e., PCR product) was then transformed into bacteria containing either the pTMV19km$^r$ or pMMV19km$^r$ mevalonate pathway plasmid and the pKD46 amp$^r$ λ red recombinase plasmid. Bacteria were grown on fosmidomycin to block the MEP pathway and switch bacterial isoprenoid metabolism to the mevalonate pathway prior to lytB deletion. The recombinase enzymes were induced by adding arabinose, which subsequently targeted recombination of the lytB-chloramphenicol construct into the bacterial genome to knock out lytB.
Figure 19:
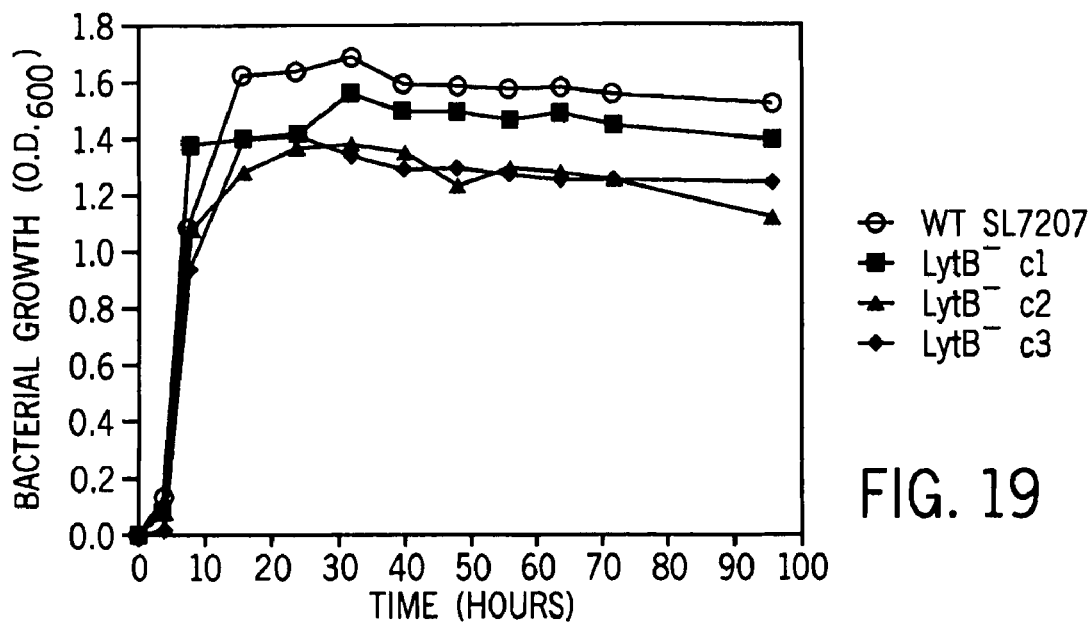
FIG. 19. Identical growth rates were observed for mutant *Salmonella enterica* serovar *Typhimurium* SL7207 bacteria using the pTMV19km$^r$ plasmid containing the full mevalonate pathway compared with wild type bacteria without lytB deletion.
Figure 20:
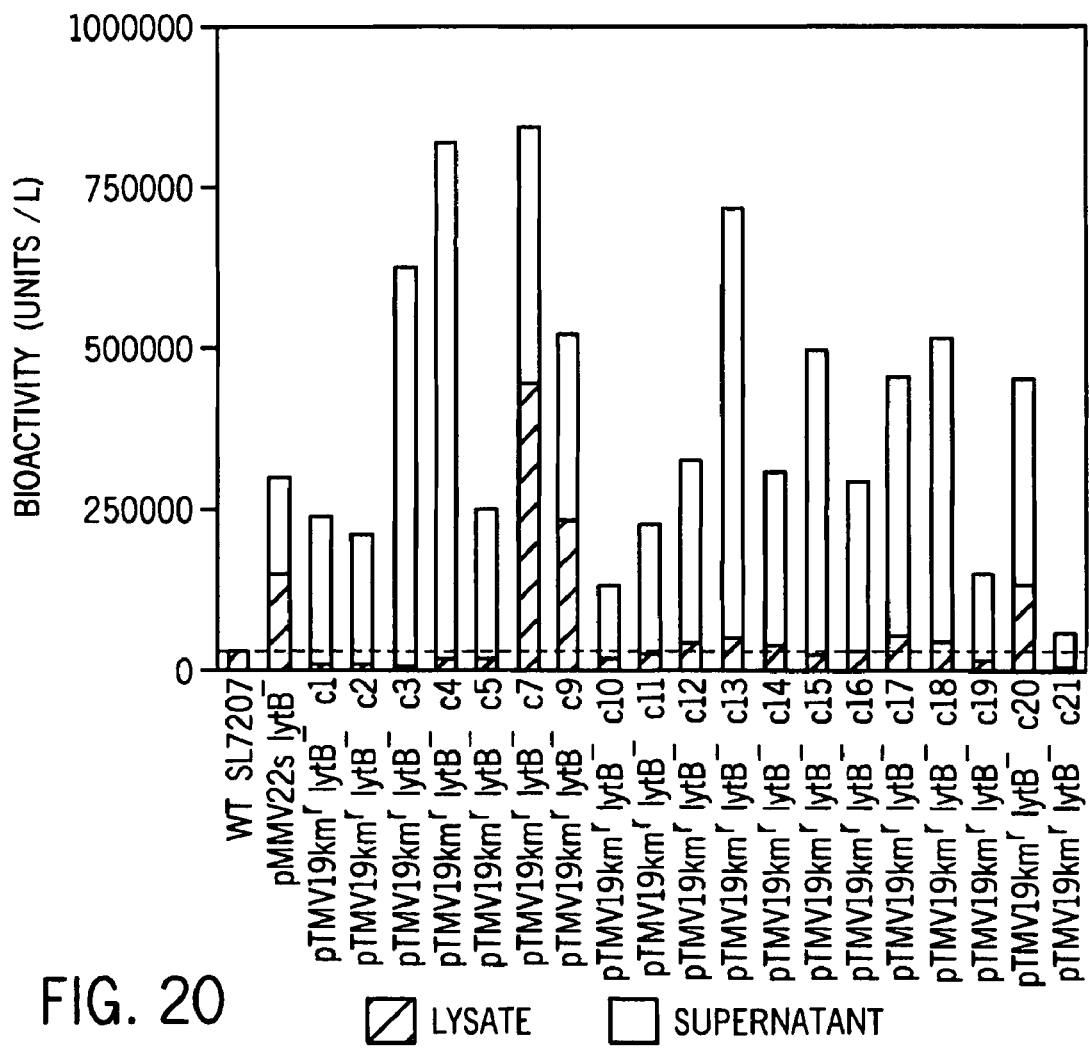
FIG. 20. Deletion of lytB in the *Salmonella enterica* serovar *Typhimurium* SL7207 vaccine strain complemented by the mevalonate pathway leads to very high production of HMBPP as compared with lytB+ wild type bacteria.

The first natural antigen structurally identified for Vγ2Vδ2 T cells was isopentenyl pyrophosphate (IPP), a metabolite all organisms use to synthesize isoprenoid compounds. Despite the presence of endogenous IPP in humans, there is no evidence that Vγ2Vδ2 T cells mediate autoimmunity, suggesting that they can distinguish between pathogen and host prenyl pyrophosphates under normal conditions (18). Two distinct pathways for IPP synthesis have been delineated that appear to contribute to this specificity (19, 20). The mevalonate pathway is found in most eukaryotes, Archaebacteria, some Eubacteria, and the cytosol of plants. The second pathway, the 2-C-methyl-D-erythritol 4-phosphate (MEP) pathway (also termed the deoxyxylulose phosphate pathway), is found in most Eubacteria, apicomplexan protozoa, cyanobacteria, and plant chloroplasts. In the MEP pathway seven enzymes have been identified: Dxs, Dxr, YgbP, YchB, YgbB, GcpE, and LytB (FIG. 12). A MEP pathway metabolite, (E)-4-hydroxy-3-methyl-but-2-enyl pyrophosphate (HMBPP) (21, 22) (also termed hydroxy-dimethylallyl pyrophosphates (HDMAPP)), has been shown to have potent stimulatory activity for Vγ2Vδ2 T cells (23). Also, the in vitro stimulatory activity of *E. coli* could be diminished by deletion of the Dxs and GcpE enzymes in the MEP pathway (24) and increased by deletion of the LytB enzyme which is downstream from HMBPP (25). *Mycoplasma* species that retain MEP pathway enzymes are also able to expand Vγ2Vδ2 T cells in vitro (26). Finally, *Listeria monocytogenes,* that uses both pathways to make isoprenoid intermediates, loses in vitro bioactivity for Vγ2Vδ2 T cells when GcpE is deleted whereas deletion of mevalonate kinase or HMG-CoA reductase did not affect bioactivity (27). Deletion of LytB in *Listeria monocytogenes* increases bioactivity 7-fold, a much smaller increase than that noted in *E. coli* (27). These findings suggest that HMBPP may act as an antigen that allows Vγ2Vδ2 T cells to distinguish exogenous from endogenous prenyl pyrophosphate antigens.

Although HMBPP appears to be a major microbial antigen, its relationship to other described phosphoantigens, termed TUBag1, TUBag2, TUBag3, and TUBag4 (28), is unclear. The structure of TUBag1 isolated from *M. fortuitum* has been reported as 3-formyl-1-butyl pyrophosphate (3-FBPP) (29). However, this compound has an identical molecular weight and chemical composition to HMBPP. The TUBag3 and TUBag 4 antigens are reported to be 3-formyl-butyl conjugates to TTP and UTP (28, 30) but little is known about the presence and relative amounts of unconjugated to nucleotide-conjugated phosphoantigens in bacteria. A closely related structure, 3-formyl-1-pentyl pyrophosphate (3-FPPP) has been proposed for the second phosphoantigen, TUBag2, isolated from *E. coli* (31) and mycobacteria (2, 32). Also, lysates of Gram positive cocci that use the mevalonate pathway, such as *Staphylococcus aureus* and Group A, B, and C *Streptococcus,* stimulate Vγ2Vδ2 T cells (33, 34, and data not shown) suggesting that an additional phosphoantigen (perhaps IPP) exists besides HMBPP and 3-FBPP as the major antigen for bacteria using the mevalonate pathway.

The synthesis of 3-FBPP (proposed as TUBag1) was recently reported. Synthetic 3-FBPP was found to have only moderate stimulatory activity ($EC_{50}\%=\sim3$ μM) rather than the high stimulatory activity previously reported ($EC_{50}\%=\sim5$-50 nM) and that its NMR spectra does not match that reported for the natural antigen (35). Moreover, with was found that the 275 Dalton compound in mycobacteria that was proposed to be 3-formyl-pentyl pyrophosphate (TUBag2) is actually 6-phosphogluconate, a compound without biological activity for Vγ2Vδ2 T cells (35). Thus, none of the TUBag antigens are 3-formyl-alkyl pyrophosphates leading to uncertainty about their structures and the relative importance of the different phosphoantigens.

To further clarify the structure and relative importance of natural phosphoantigens in different bacteria and to confirm the importance of MEP pathway enzymes in determining in vitro and in vivo stimulation of Vγ2Vδ2 T cells, bacterial antigens were isolated and mutations that affect bacterial antigen levels were identified. We find that unconjugated HMBPP is the major bacterial antigen in multiple species using the MEP pathway. Consistent with this, mutations that affect bacterial antigen levels were primarily in enzymes of the MEP pathway or genes regulating this pathway. No evidence for additional enzymes that could produce 3-FBPP was found. The HMBPP metabolite was highly preferentially recognized over IPP by Vγ2Vδ2 T cells including neonatal γδ T cells. Moreover, in the human-PBL-SCID-beige mouse model, only a bacterial mutant with high levels of HMBPP expanded Vγ2Vδ2 T cells. These findings demonstrate a major role for HMBPP in determining activation of Vγ2Vδ2 T cells for bacteria using the MEP pathway.

Materials and Methods

Antigens

Ethyl pyrophosphate (EPP) was synthesized as described (1). Bromohydrin pyrophosphate (BrHPP) was provided by Eric Oldfield (University of Illinois, Urbana-Champagne). HMBPP was synthesized as described (36).

Derivation and Maintenance of γδ T Cell Clones

T cell clones were propagated by periodic re-stimulation as described (37). The 12G12, DG.SF68, and CP.1.15 Vγ2Vδ2 T cell clones have been described (1). AC.2 and AC.8 are fetal liver clones (37) whereas CB.32.26 is a cord blood clone (38).

Purification and Characterization of the Major Antigen from *M. smegmatis* and *M. fortuitum*

Antigen was purified from 34 liters of *M. smegmatis* and 4 liters of *M. fortuitum* culture grown in Middlebrook 7H9 broth. The culture supernatants were passed though a carbon-Celite column (2) followed by tangential ultrafiltration (1,000 m.w. cut-off, Pall-Filtron, Northborough, Mass., USA). Minimal bioactivity (5-10%) was lost during these steps. Compounds in the ultrafiltrates were separated on a Q-Sepharose-Fast flow column (5×30 cm) by FPLC using an ammonium acetate gradient. Bioactive fractions were identified by their ability to stimulate the proliferation of a Vγ2Vδ2 T-cell clone and then pooled. The single peak of bioactivity was further purified by HPLC using a DEAE-5PW column (150×21.5 mm, Bio-Rad, Hercules, Calif., USA) followed by a Mono Q column (Amersham Pharmacia Biotech, Piscataway, N.J., USA) eluted with a triethylammonium bicarbonate gradient. The antigen was further purified using a Luna C18 column (250×4.6 mm, Phenomenex, Torrance, Calif., USA) under ion pairing conditions with a tertiary solvent system. Solvent A: 100 mM triethylammonium bicarbonate (TEAB), pH 8.0 (prepared by bubbling $CO_2$ through 100 mM TEA until pH 8.0); solvent B: 100 mM TEAB in 10% (v/v) methanol; and solvent C: 100 mM TEAB in 50% (v/v) methanol. The column was eluted as follows: 0-10 min isocratic in solvent A at 1 ml/min; 10-70 min linear gradient 0-10% B in A at 1 ml/min; 70-75 min linear gradient 10-50% C in A at 0.5 ml/min; 75-90 min isocratic 50% C in A at 0.5 ml/min. One minute fractions were collected from which 1 µl of each fraction was tested for stimulation of a Vγ2Vδ2 T cell clone. Note that since this is a volatile buffer system, there is some variation in retention times for identical compounds. Each 1 min fraction was assayed for bioactivity with a γδ T cell clone and analyzed by electrospray ionization tandem mass spectrometry in the negative mode (precursor-ion and product-ion analyses) to identify and quantitate phosphate-containing compounds as previously reported (2). Electrospray ionization tandem mass spectrometry (ES MS/MS) spectra were obtained in negative ion mode using API-III, API 300, and API Qstar Pulsar I mass spectrometers (Applied Biosystems/MDS Sciex, Ontario, Canada), as described (2). The measured accurate mass of the compounds was determined by Fourier Transform Ion Cyclotron Resonance (FT-ICR) mass spectrometry using electrospray ionization in the negative ionization mode on the 7 Tesla spectrometer at the Environmental Molecular Sciences Laboratory. Internal calibration employing IPP and geranyl pyrophosphate was used for accurate mass measurements.

Mutation of E. coli W3110 Bacteria

E. coli mutants that carry point mutations in ygbP, ychB, ygbB, and gcpE were derived from E. coli W3110 following treatment with N-methyl-N'-nitro-N-nitrosoguanidine as described (39-42). The mutant bacteria were engineered for isoprenoid metabolism through a partial mevalonate pathway by transformation of the parent bacteria with the pTMV20KM plasmid (which includes the Streptomyces sp. strain CL190 mevalonate pathway genes, mevalonate kinase, phosphomevalonate kinase, diphosphomevalonate decarboxylase, and isopentenyl disphosphate isomerase plus a kanamycin resistance gene (43)). Since genes upstream of mevalonate are not included, addition of mevalonate (0.1 mg/ml) into the media was required for growth (FIG. 12). The DK310 LytB$^{G120D}$ (pTMV20KM) strain was derived from the isopentenyl diphosphate isomerase disruptant strain, DK310, by treatment with N-methyl-N'-nitro-N-nitrosoguanidine and transformation with pTMV20KM (44). The dxr mutant was derived by the insertion of a kanamycin resistance gene into the coding sequence of dxr as described (45) except that the parent bacteria were transformed with the pTMV19 plasmid which includes the Streptomyces sp. strain CL190 mevalonate pathway genes found in pTMV20 plus the HMG-CoA reductase and HMG-CoA synthase genes (43) and addition of mevalonate (0.1 mg/ml) into the media. The mutation for each strain is detailed in Table 1. "Leaky" mutants were identified by plating bacteria on LB plates lacking mevalonate and culturing overnight at 37° C. followed by 10 days at room temperature.

Transposon Mutagenesis of the DK310 LytB$^{G120D}$ Mutant

Mutant strains were generated by transposon-mediated mutagenesis of the DK310 LytB$^{G120D}$ (pTMV20KM) bacteria using the EZ:TN™ <DHFR-1> Tnp Transposome™ kit (Epicentre, Madison, Wis., USA) (44). Bacterial mutants thus generated were arrayed in a 96 well format and about 15,000 were screened for the loss of bioactivity with the 12G12 Vγ2Vδ2 T cell clone and for their ability to grow in the absence of mevalonate. To ensure the complete loss of activity, bacteria were further grown at room temperature for 4-7 days. Genomic DNA was isolated from mutants using a MasterPure™ DNA purification kit (Epicentre) and directly sequenced with a pair of primers specific to each end of the transposon at the University of Iowa DNA sequencing facility. The genomic transposition sites were located using BLAST programs maintained at the NCBI web site of the National Library of Medicine.

Preparing Bacterial Supernatants and Sonicates

To test bacterial supernatants and sonicates for their ability to stimulate Vγ2Vδ2 T cells, E. coli bacteria were grown to late stationary phase in 1 liter of LB media in 2.6 liter fluted Fernback flasks by incubating for ~24 h at 37° C. in an Innova 4400 shaker oscillating at 225 rev/min, this maximizes bioactivity. The bacteria were harvested by centrifugation at 380×g for 15 min at 4° C. The culture supernatant was removed and the bacteria washed twice with PBS. Bacteria from 1 L of culture were suspended in 10 ml of PBS and continuously probe sonicated for 10 minutes on ice at a 4.5 setting (Sonic Dismembrator Model 550, Fisher Scientific). The sonicated bacteria were centrifuged at 300×g for 15 min at 4° C. The supernatants from the sonicated bacteria and the culture supernatants were heated in a boiling water bath for 5 minutes, cooled on ice for 5 min, centrifuged at 16,000×g for 30 minutes at 4° C., filter sterilized with a 0.22 µm filter, and frozen at −80° C. Note that the heating caused precipitation of protein and other bacterial components that inhibit T cell proliferation and that give falsely low estimates of bioactivity but did not affect the overall bioactivity for Vγ2Vδ2 T cells (44). Heating also dissociates prenyl pyrophosphates from proteins and other bacterial components that prevent the passage of prenyl pyrophosphates through membrane ultrafiltration units with molecular cutoffs greater than 1,000-3,000 Daltons.

Vγ2 Vδ2 T Cell Proliferation Assay and the Quantitation of Bacterial Bioactivity for Vγ2 Vδ2 T Cells.

T cell proliferation assays were performed as previously described (1). Mean proliferation and standard error of mean of triplicate cultures are shown. To quantitate bioactivity, the reciprocal dilution of the bacterial supernatant or sonicate that gave half-maximal proliferation was determined relative to a standard ethyl pyrophosphate antigen preparation (44). One unit of bioactivity was the amount of antigen in 1 ml that gave half-maximal antigen-induced proliferation of a Vγ2Vδ2 T cell clone (usually DG.SF68 or CP. 1.15) and corresponds to an HMBPP concentration of 31.6 pM or 31.6 femtomoles/ml and an IPP concentration of 3 µM or 3 nmoles/ml.

Expansion of Vγ2 Vδ2 T Cells by Nonpeptide Antigens

PBMC were isolated either from leukopacs or buffy coats by density centrifugation over Ficoll-Hypaque (Amersham Pharmacia Biotech). 1×10$^5$ of PBMC were cultured in 96-well round-bottom plates in complete RPMI 1640 (37) alone or in complete RPMI 1640 with 50 µM IPP or 0.316 µM HMBPP. On day 3, 100 µl of supernatant were replaced with complete medium supplemented with 1.7% human serum and 1 nM recombinant human IL-2 (Chiron Corporation, Emeryville, Calif., USA). On day 7, the PBMC were harvested, counted, stained with anti-Vδ2 (BB3, gift from A. Moretta) and anti-CD3 (HIT3a, BD Pharmingen, San Diego, Calif., USA) monoclonal antibodies (mAbs), and analyzed by 2-color flow cytometry. The Institutional Review Board at the University of Iowa approved these studies.

Expansion of Vγ2 Vδ2 T Cells by Live Bacteria

E. coli wild-type, LytB$^{G120D}$, and LytB$^{G120D}$ yhjK$^-$ bacteria were grown to mid-log phase and stored in LB broth containing 10% glycerol at −80° C. until use. To determine colony forming units, bacteria were washed once with PBS and grown on LB plates. For the transwell assay, $1-3\times10^6$ bacteria were added in 0.1 ml RPMI 1640 medium to the inner wells (Corning Costar, Kennebunk, Me., USA). The inner well was separated from the outer well by a 0.4 μm membrane. $2\times10^6$ PBMC were added to the outer well in 0.9 ml of complete medium. After 4 h, the inner wells were removed leaving the PBMC in culture. On day 3, half of medium was replaced with complete medium supplemented with human serum and rIL-2. On day 6, the PBMC were harvested, counted, and Vγ2Vδ2 T cells determined by flow cytometry using anti-Vδ2 and anti-CD3 mAbs.

Vγ2Vδ2 T Cell Proliferation in Human-PBL-SCID-beige Mice

Homozygous C.B-Igh-1$^b$/GbmsTac-Prkdc$^{SCID}$-Lyst$^{bg}$N7 (C.B-17 SCID-beige) male mice (age 5-6 weeks old) were purchased from Taconic (Germantown, N.Y., USA) and maintained in microisolator cages. Animals were fed autoclaved food and water and all manipulations were performed in laminar flow cabinets. In vivo expansion of γδ T cells was performed in SCID-beige mice using either HMBPP-activated or unactivated PBMC. To assess the effector capability of Vγ2Vδ2 T cells, PBMC were activated for 24 h in vitro with 0.316 μM HMBPP, washed, and $2.5-3\times10^7$ cells injected i.p. into each mouse in 0.5 ml of RPMI. To assess the in vivo stimulatory capability of mutant bacteria, unactivated PBMC were used. Two h later, each SCID-beige mouse was injected i.p. with either wild-type or LytB$^{G120D}$ (termed lytB$^-$ in the figures) E. coli at $1\times10^6$-$1\times10^7$ bacteria in 0.5 ml of RPMI medium. Alternatively, varying amounts of HMBPP were given in 0.25 ml of PBS. 5000 I.U. of recombinant human IL-2 (Chiron, Emeryville, Calif., USA) was given i.p. every other day starting on day 0. On day 9, the mice were sacrificed and peritoneal cells were harvested by washing the peritoneum with 4 ml of PBS. The peritoneal cells were counted and analyzed by flow cytometry using anti-Vδ2 and anti-CD3 monoclonal antibodies to determine the percentage of Vγ2Vδ2 T cells among human CD3$^+$ T cells. The Institutional Animal Care and Use Committee of the University of Iowa approved all animal protocols. Data were tested for statistically significant differences using the non-parametric Mann-Whitney U test.

Results

Purification of the Major Antigen for Vγ2Vδ2 T Cells from *Mycobacteria*

Figure 21A:
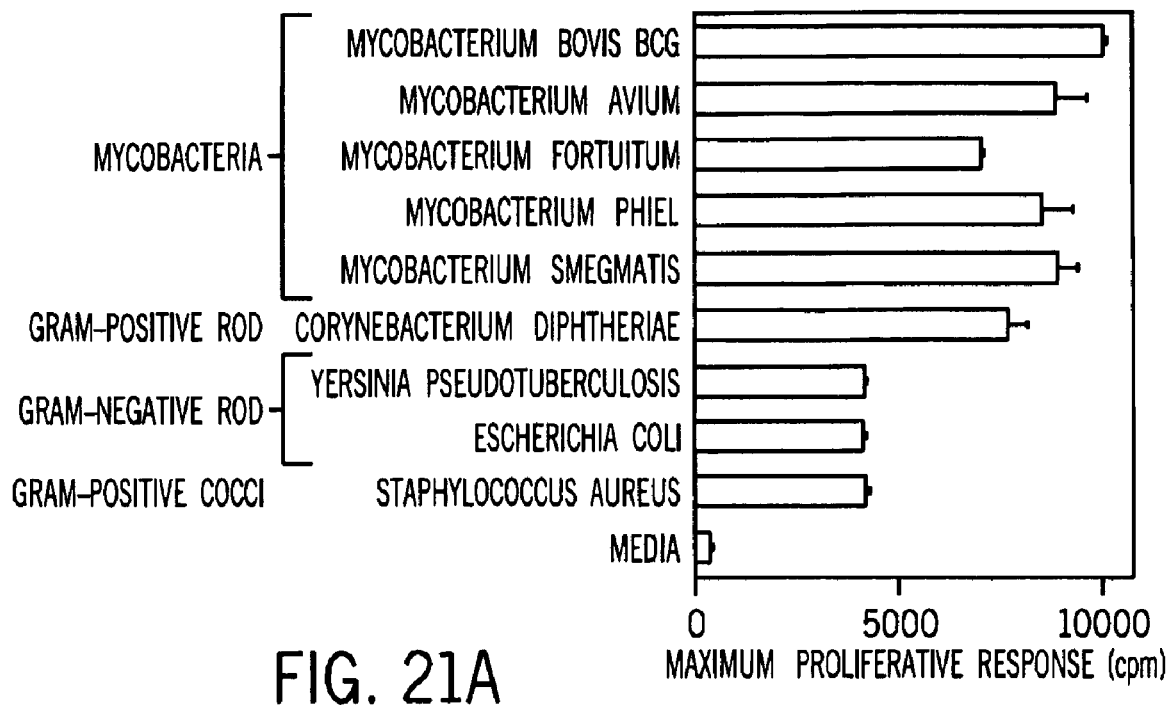
FIG. 21. Characterization of the major bacterial nonpeptide antigen for Vγ2Vδ2 T cells. (A) Vγ2Vδ2 T cell clone, CP. 1.15, stimulation with various bacterial sonicates. (B) The major mycobacterial phosphoantigen has a molecular weight of 262 Daltons. The major phosphoantigen was purified from *M. smegmatis* and *M. fortuitum* by several chromatographic steps followed by ion-pairing reverse-phase chromotography on a Luna C18 column. Bioactive fractions were identified by their stimulation of a Vγ2Vδ2 T cell clone and analyzed by ES MS/MS for ions containing phosphate residues. Note the strict correlation between bioactivity and the presence of an [M-H]⁻ ion of m/z 261 (corresponding to a 262 Dalton molecular weight). (C) The m/z 261 ion contains a pyrophosphate moiety and has the chemical composition of $C_5H_{11}O_8P_2$. The m/z 261 ion was analyzed by tandem mass spectrometry revealing a m/z 159 product ion corresponding to a pyrophosphate moiety. The chemical composition was determined from the accurate molecular mass measured by FT-ICR MS. A $C_5H_{11}O_8P_2$ composition for the m/z 261 ion was consistent with the calculated mass to within +0.72 parts per million. (D) The m/z 261 ion is common to *Mycobacteria* and the Gram-negative rod bacteria, *Y. enterocolitica*. Antigens were purified from lysates of *M. tuberculosis* and *Y. enterocolitica* and from culture supernatants of *M. smegmatis* and *M. fortuitum*. The biologically active fractions were resolved by ion pairing chromatography on a Luna C18 column. Note that since this is a volatile buffer system, there is some variation in retention times for identical compounds. (E) The m/z 261 ion is common to *M. smegmatis* and *E. coli*. The biologically active fractions were resolved by ion pairing chromatography on a Luna C18 column. (F) Phosphoantigen levels during bacterial growth. (top) Bioactivity levels during *M. smegmatis* growth. Stationary phase was achieved at day 2-3. Intracellular bioactivity was not determined but in stationary phase cultures constituted <5% of total bioactivity. (middle) Bioactivity levels during *M. fortuitum* growth. This mycobacterium grows slower than *M. smegmatis*. Data is from (49) and is included for comparison. (bottom) Bioactivity levels during *E. coli* growth. Note that phosphoantigen levels are maximal during the late stationary phase of growth when the majority of the bioactivity is in the culture supernatant.

Although previous studies showed that mycobacterial lysates contain nonpeptide antigens that stimulate γδ T cells, there are questions about the relative importance of HMBPP, 3-FBPP, and IPP as well as the relative abundance of unconjugated and nucleotide-conjugated compounds (1, 2, 28, 46-48). Therefore, we prepared lysates from various bacteria, including mycobacteria (the BCG vaccine strain of *M. bovis*, opportunistic (*M. avium* and *M. fortuitum*) and environmental (*M. smegmatis*) species), Gram-positive and -negative rods, and Gram-positive cocci, and evaluated them for their ability to stimulate Vγ2Vδ2 T cells. Despite their divergent origins, all bacterial lysates stimulated Vγ2Vδ2 T cells including the lysate from *S. aureus*, a bacterium that uses the mevalonate pathway for IPP synthesis (FIG. 21A).

Figure 21C:
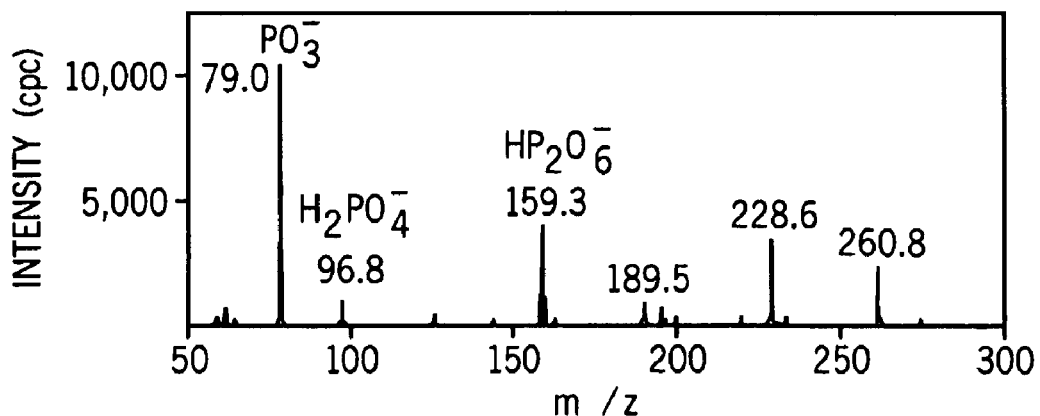
Figure 21B:
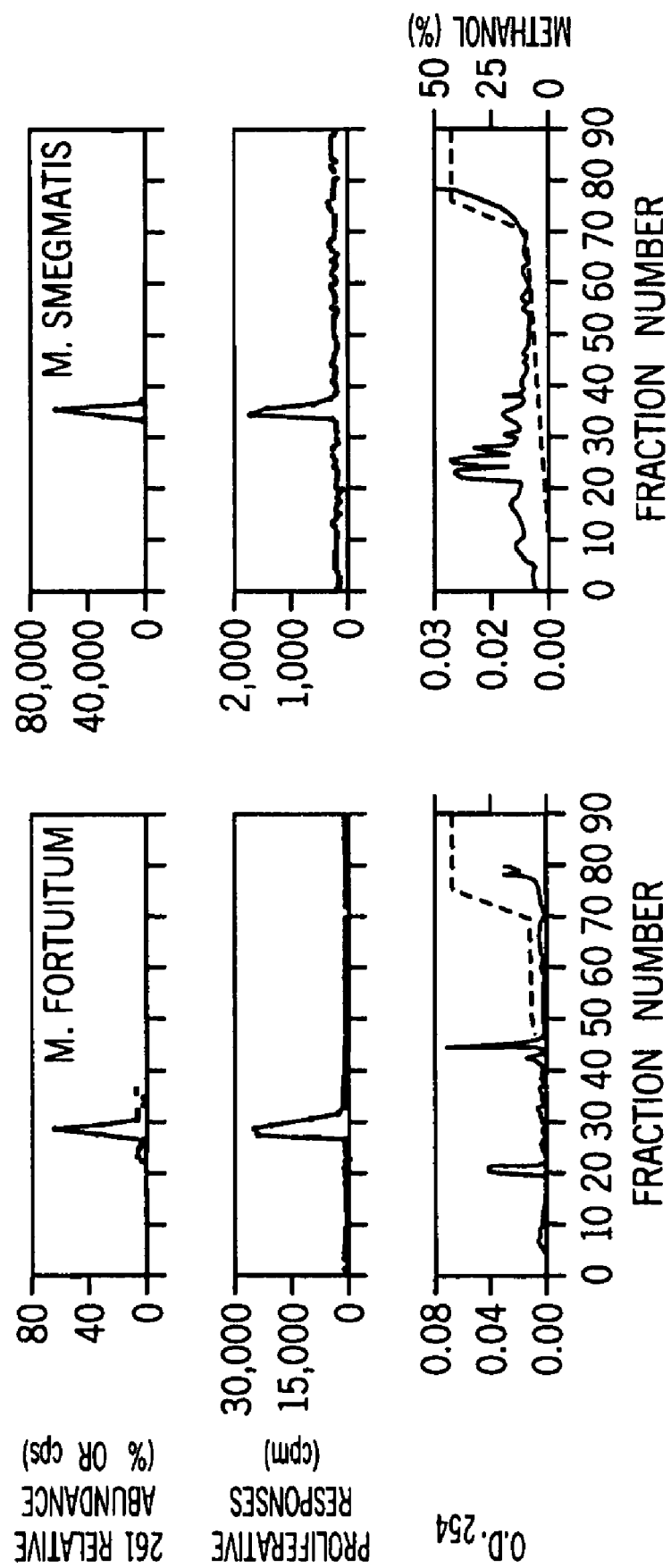

To identify the compound(s) responsible for bioactivity in bacteria, the major peak of bioactivity was purified from *M. fortuitum* and *M. smegmatis*. 90-95% of the antigenic activity in the supernatant from *M. smegmatis* passed through an activated charcoal-Celite column that retains nucleotide, nucleotide-conjugated, and hydrophobic compounds (1). Thus, nucleotide-conjugated antigens, such as the 5'-UTP-conjugated antigen reported for *M. fortuitum* (30) and the 5'-dTTP-conjugated antigen reported for *M. tuberculosis* (28), accounted for, at most, 5-10% of bioactivity in *M. smegmatis*. Unlike antigenic activity from lysates of heat-killed *M. tuberculosis* (FIG. 21D), subsequent anion exchange and ion-pairing reverse phase chromatography revealed only one peak of bioactivity from both *M. fortuitum* and *M. smegmatis*. This peak of bioactivity for Vγ2Vδ2 T cells on ion-pairing reverse-phase chromatography (FIG. 21B, middle panels) correlated with the presence of an ion with a mass to charge ratio (m/z)=261 ([M-H]$^-$) (FIG. 21B, upper panels). Further characterization of the m/z 261 ion using product-ion analysis by electrospray ionization tandem mass spectrometry (ES MS/MS) revealed that the m/z 261 ion is pyrophosphorylated, as evidenced by the presence of products ions at m/z 159 (corresponding to $HP_2O_6^-$), m/z 97 (corresponding to $H_2PO_4^-$), and m/z 79 (corresponding to $PO_3^-$) (FIG. 21C). The measured accurate mass of the m/z 261 ion was 260.993655 as determined by Fourier transform ion cyclotron resonance mass spectrometry (FT-ICR MS). Based on this weight, the m/z 261 ion matched most closely a chemical composition of $C_5H_{11}O_8P_2$ (+0.72 ppm error) (FIG. 21C). This is identical to the negative ion [M-H]$^-$ of HMBPP and of 3-FBPP. Synthetic HMBPP and 3-FBPP had nearly identical major ions on collision induce dissociation using an ion trap mass spectrometer (data not shown and 32) precluding the use of this technique to distinguish between the two compounds. Therefore, the major antigen could be either HMBPP or 3-FBPP.

Figure 21D:
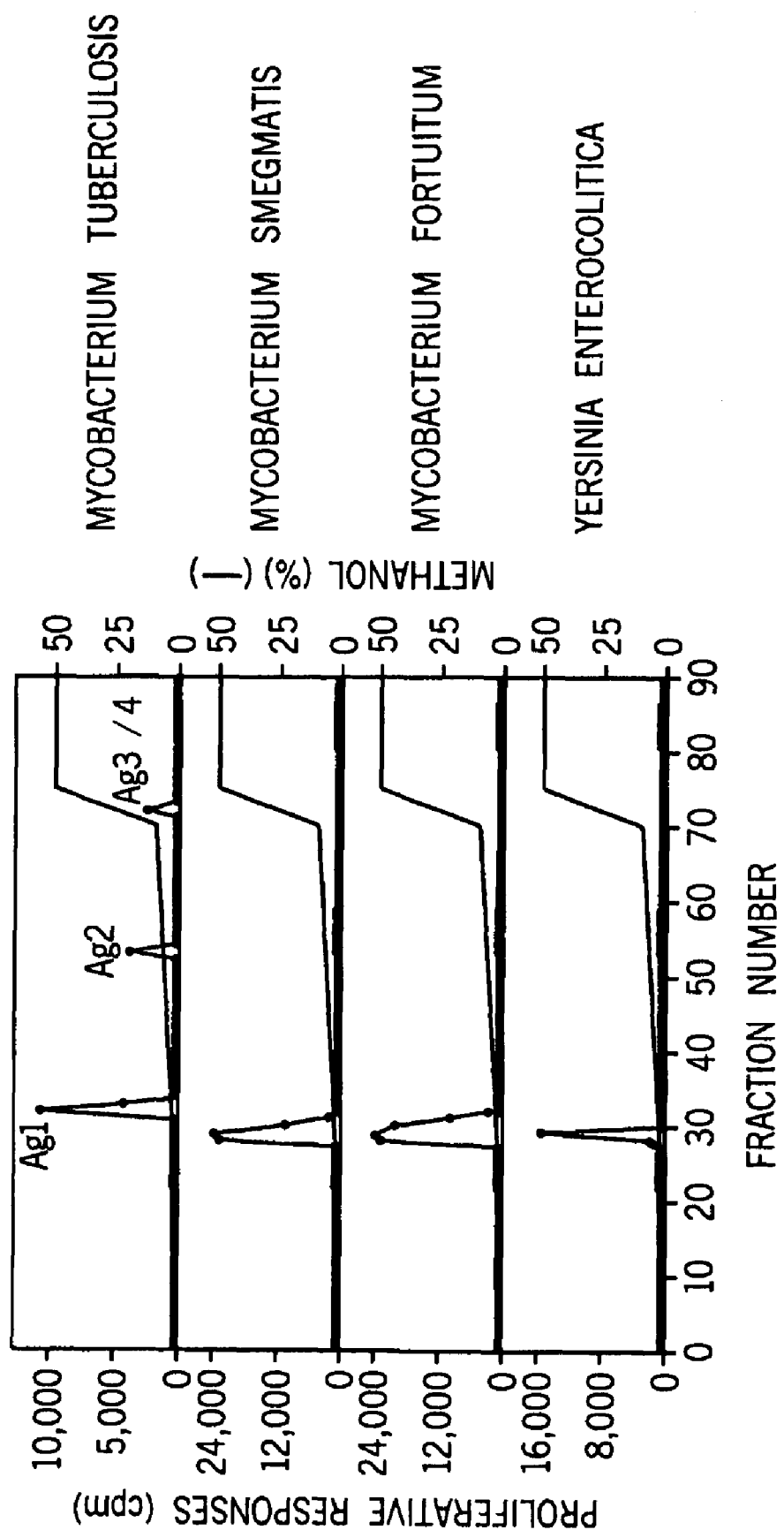
Figure 21E:
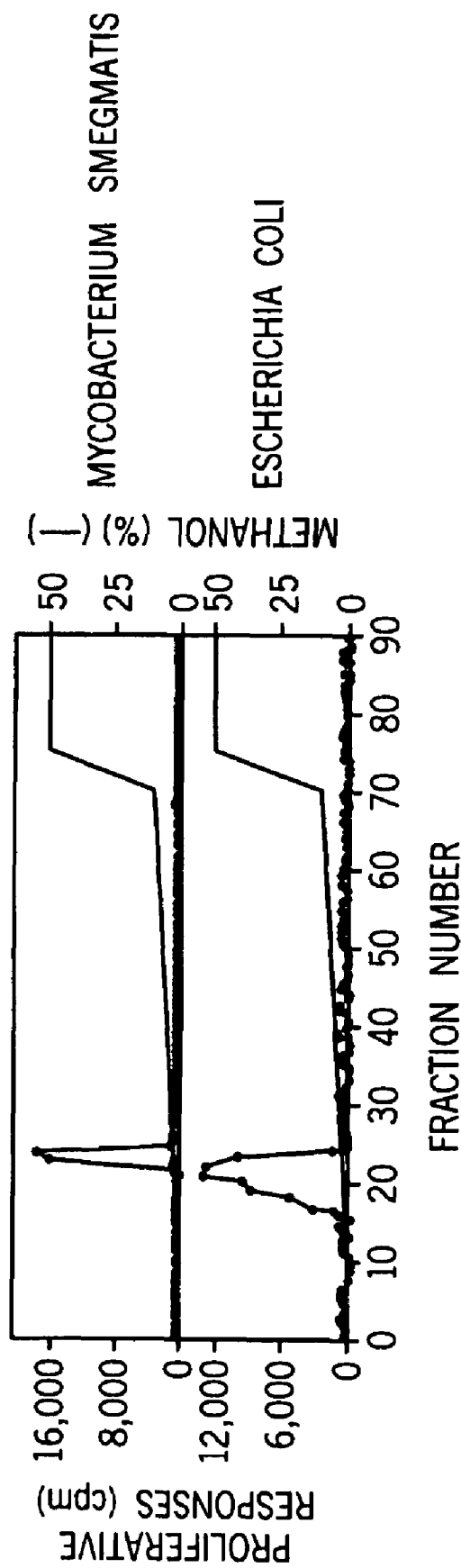
Figure 21F:
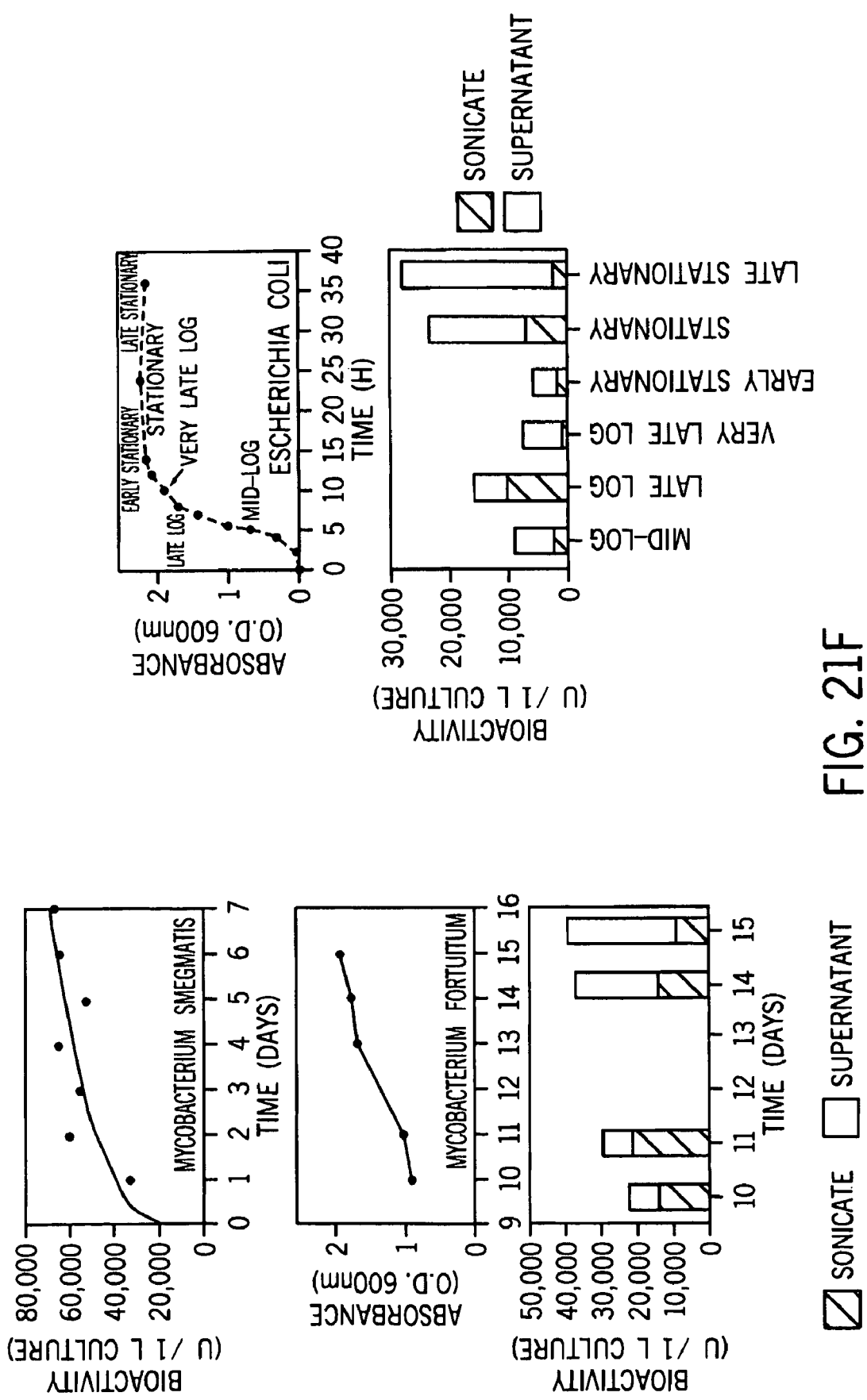

The m/z 261 ion of *M. smegmatis* and *M. fortuitum* had similar retention times to TUBag1 in *M. tuberculosis* and the major antigen in *Y. enterocolitica* (FIG. 21D) and *E. coli* (FIG. 21E). Note, that there were minor variations in retention times for identical compounds due to the use of a volatile buffer. Nucleotide conjugated compounds were not produced by either *E. coli* or *Y. enterocolitica* since only 1 peak of bioactivity was isolated (FIGS. 21D and 21E). To determine if the level of bioactivity was related to the bacterial growth phase, cultures of *M. smegmatis*, *M. fortuitum* (data from 49), and *E. coli* were grown and bioactivity for Vγ2Vδ2 T cells quantitated for different growth phases. In all three bacteria, antigen levels were highest in the late stationary phase with most of the bioactivity present in the culture supernatants (FIG. 21F). The presence of bioactivity in the culture supernatants of actively growing bacteria confirms earlier studies (30, 49) although it is not clear whether the major antigen is actively secreted or just released by dying bacteria. In some other bacterial species, antigenic activity is retained in the cytoplasm (data not shown). Since the highest levels of bioactivity are found in late stationary phase cultures, bioactivity levels for bacteria were determined at this time point.

Figure 22A:
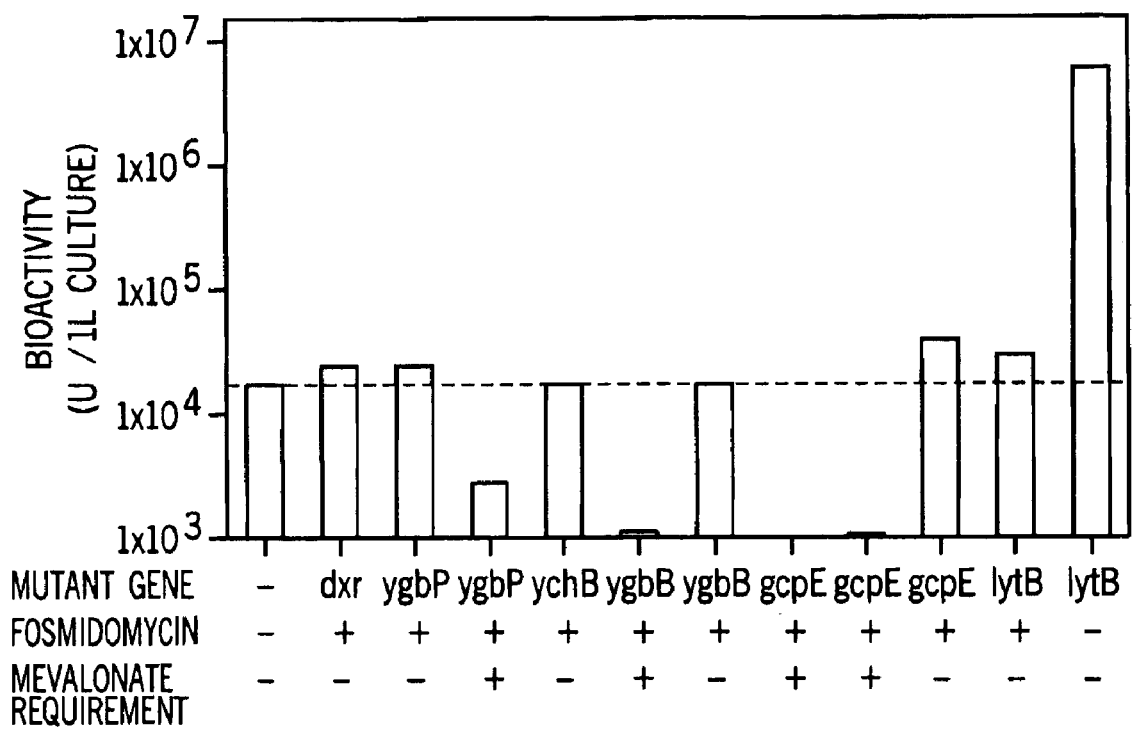
FIG. 22. Bioactivity of *E. coli* with mutations in the MEP pathway. (A) Loss of bioactivity of *E. coli* with mutations in the MEP pathway correlates with mevalonate-dependent growth. Sonicates and culture supernatant were prepared from 1 L of wild-type *E. coli* and MEP pathway-defective *E. coli* strains complemented with the mevalonate kinase, phosphomevalonate kinase, diphosphomevalonate decarboxylase, and isopentenyl disphosphate isomerase genes from the mevalonate pathway. Fosmidomycin (FMM, 20 µg/ml) was included to partially block the dxr enzyme and mevalonate (1 mg/ml) was added to support isoprenoid biosynthesis through the mevalonate pathway by enzymes introduced into the bacteria. One unit of bioactivity corresponds to 31.6 femtomoles of HMBPP per ml. The order of the mutants (left to right) is the same as Table I. Note that only those bacteria with complete lack of mevalonate-independent growth had low levels of bioactivity, despite the presence of fosmidomycin in all mutant cultures. (B) Bioactivity of LytB$^{G120D}$ mutant *E. coli* mutated by transposons. Mutants were screened for bioactivity for Vγ2Vδ2 T cells and for mevalonate-dependent growth. Mutants are as in Table II.

Mutation of Genes in the MEP Pathway Identifies HMBPP as the Primary Bacterial Antigen for Vγ2 Vδ2 T Cells Given its product ion spectra, chemical composition, and the complete delineation of the MEP pathway, we hypothesized that the m/z 261 ion phosphoantigen was HMBPP rather than 3-FBPP. To test this hypothesis using a genetic approach, we made *E. coli* strains with mutations in enzymes of the MEP pathway, the pathway that produces HMBPP and IPP in *E. coli* (Table I). Since this pathway is essential for viability, these mutants were derived from an *E. coli* strain that was first modified to contain a partial mevalonate pathway. The mevalonate pathway synthesizes IPP in mammals but does not make HMBPP or any other MEP pathway intermediate (FIG. 12). Mutations in MEP pathway enzymes upstream from HMBPP (YgbP, YgbB, and GcpE), that completely abrogated growth in the absence of mevalonate, also markedly reduced bioactivity of Vγ2Vδ2 T cells (FIG. 22A and Table I). Conversely, when the downstream enzyme LytB was mutated, the bacteria showed a 300-1.500-fold increase in Vγ2Vδ2 T cell bioactivity (FIG. 22A). As expected, this elevated level of bioactivity found in LytB$^{G120D}$ mutant bacteria could be reduced to wild-type levels by adding fosmidomycin (FMM), a specific inhibitor of the upstream enzyme, deoxyxylulose-5-phosphate reductoisomerase (dxr). The level of HMBPP appears to be tightly regulated since bacteria with point mutations that greatly slowed but did not completely eliminate growth had similar bioactivity levels as wild type bacteria in late stationary phase cultures (Table 1). The requirement for GcpE for biological activity confirms previous results (24, 25) and we now show that other enzymes in the pathway are similarly required.

Figure 22B:
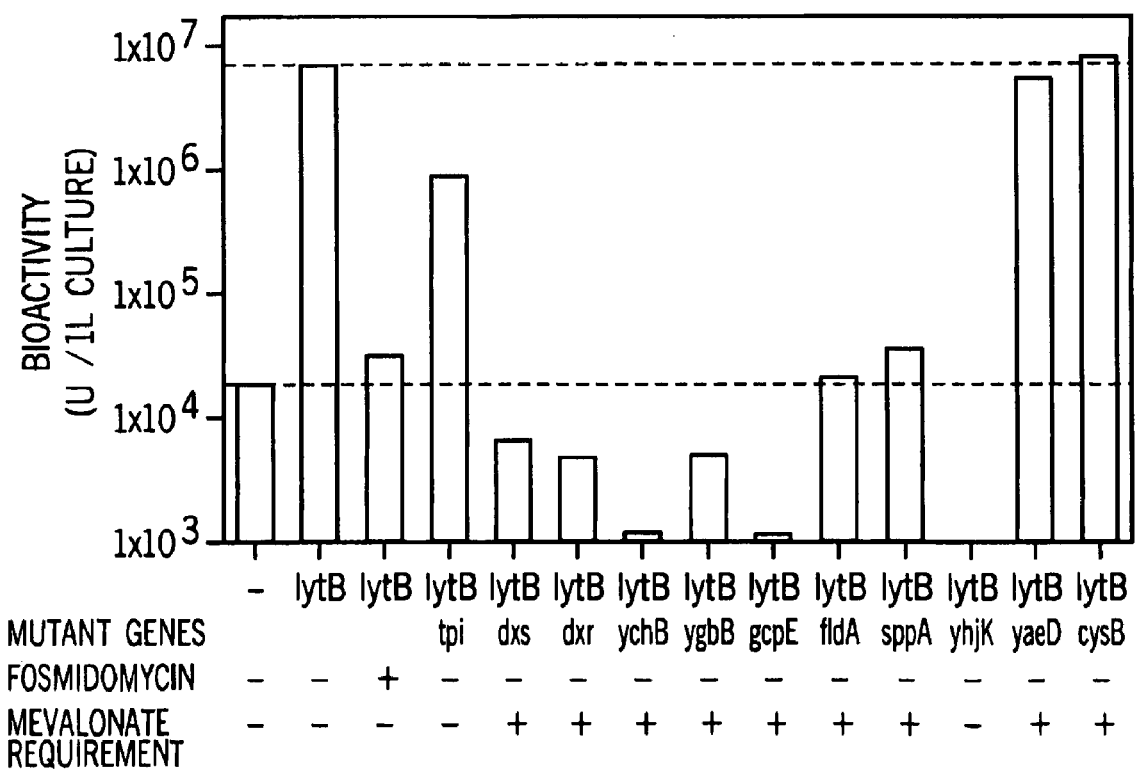

As it is possible that 3-FBPP is produced as a side metabolite from HMBPP by a novel enzyme, we performed transposon mutagenesis of the LytB$^{G120D}$ strain that accumulates high levels of bioactivity to identify genes required for bioactivity. Since transposons can insert throughout the bacterial genome, this technique should identify genes required for bioactivity for Vγ2Vδ2 T cells potentially including genes not in the MEP pathway. Approximately 15,000 mutants were screened for their bioactivity for γδ T cells and for their ability to grow independently of mevalonate (Table II). Twenty-seven clones had lower bioactivity compared to the LytB$^{G120D}$ bacteria (FIG. 22B). Direct genomic sequencing of these mutants revealed that 23 of the 27 of those mutants had a transposon inserted into a known gene in the MEP pathway identifying 5 out of 6 upstream enzymes from HMBPP. These mutants did not grow in the absence of mevalonate, since they lacked the ability to synthesize IPP through the MEP pathway (Table II and FIG. 22B).

Two additional genes, fldA and sppA, were found to be important in the synthesis of HMBPP. fldA encodes flavodoxin I that functions as an electron donor for GcpE in the synthesis of HMBPP (21). sppA (not previously reported) encodes a signal peptide peptidase that cleaves signal peptides and may be required for enzyme activity. Mutation of triose phosphate isomerase (tpi) also reduced bioactivity since it is required to convert dihydroxyacetone phosphate to glyceraldehyde-3-phosphate, a precursor for the MEP pathway. Mutation of yhjK reduced bioactivity of the LytB$^{G120D}$ mutant but when deleted in wild-type *E. coli* γδ bioactivity and bacterial growth were normal (unpublished data). yhjK encodes a transmembrane signaling protein that likely regulates cyclic diguanylate monophosphate levels and that may, in turn, regulate HMBPP pool size only in the LytB$^{G120D}$ strain. Two mutants, cysB and yaeD, required mevalonate for growth but their HMBPP levels remained unaltered. yaeD encodes a phosphatase involved in LPS synthesis; cysB encodes a protein involved in the regulation of cysteine synthesis and may be required for activity of the mutant LytB$^{G120D}$ enzyme. Importantly, no enzyme that could convert HMBPP to 3-FBPP was identified. These genetic studies complement our structural analysis (FIG. 22) and functional tests on synthetic 3-FBPP (35) and suggest that HMBPP, rather than 3-FBPP, is the major antigen for bacteria using the MEP pathway.

Figures 23A, 23B:
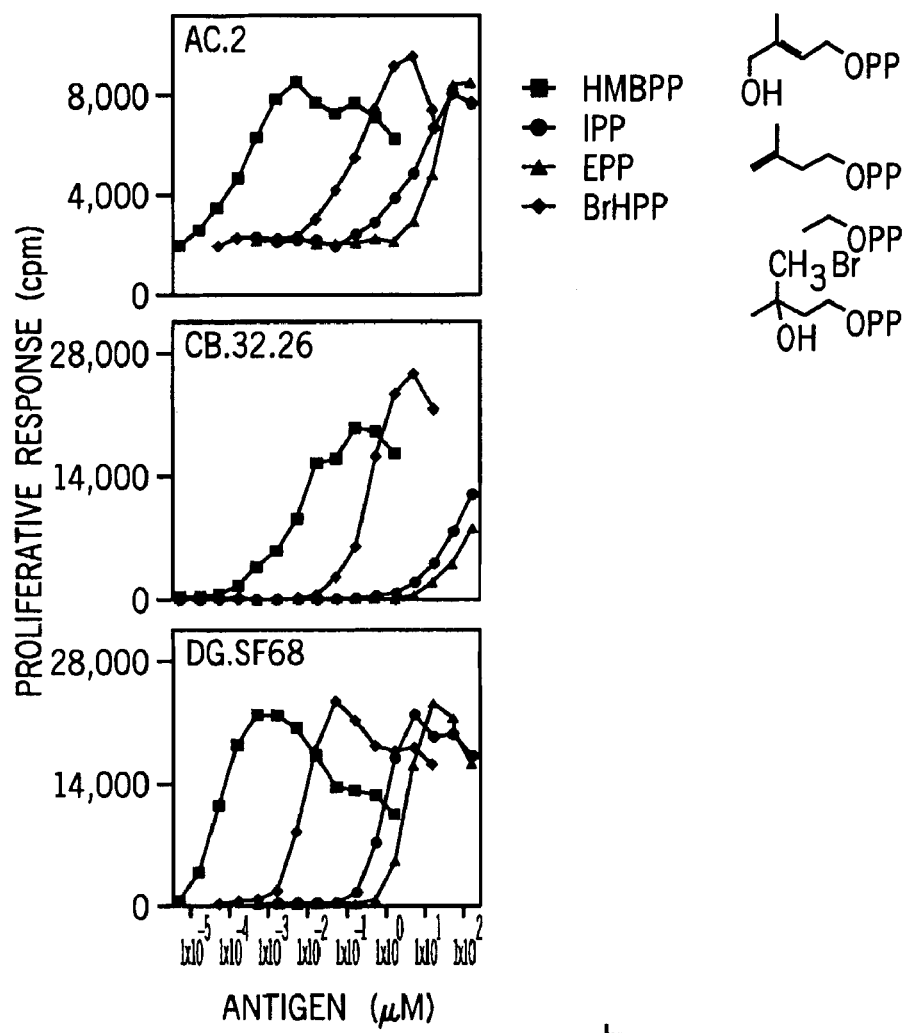
FIG. 23. HMBPP is the most immunogenic nonpeptide antigen for Vγ2Vδ2 T cells. (A) HMBPP is the most immunogenic natural phosphoantigen. Vγ2Vδ2 T cell clones from fetal liver (AC.2), cord blood (CB.32.26), and adult synovial fluid (DG.SF68) were cultured for 48 h with different concentrations of the indicated antigens in the presence of mitomycin C-treated Va-2 cells. Proliferation was measured by ³H-thymidine incorporation. Error bars are +/−1 standard error of the mean. (B) HMBPP expands Vγ2Vδ2 T cells in PBMC. PBMC were cultured in either medium alone, or medium supplemented with 50 µM IPP or 0.316 µM HMBPP. On day 7, PBMC were harvested and analyzed by two-color flow cytometry using anti-Vδ2 and anti-CD3 specific mAbs.

HMBPP is a Highly Potent Phosphoantigen and its Recognition can be Mediated by Vγ2 Vδ2 T Cell TCRs that are Present at Birth To verify that HMBPP stimulates Vγ2Vδ2 T cells, synthetic HMBPP was tested for its ability to stimulate several Vγ2Vδ2 T cell clones including fetal liver clones (AC.2 and AC.8) that use the invariant Vγ2 (Vγ9) chain (50); a cord blood clone, CB32.26 (38); and adult clones, 12G12, DG.SF68, and CP.1.15. For all clones, HMBPP was 30,000-fold more antigenic than IPP (FIG. 23A, half-maximal proliferation for HMBPP and IPP for the AC.2 and DG.SF68 clones was 36 pM and 1 µM, respectively, and unpublished data) and 100-300-fold more antigenic than bromohydrin pyrophosphate, a synthetic phosphoantigen. To confirm that the Vγ2Vδ2 TCR mediated HMBPP recognition, a Vγ2Vδ2 TCR transfectant, DBS43, was tested and found to release IL-2 in response to HMBPP (unpublished data). HMBPP also stimulated the expansion of Vγ2Vδ2 T cells from normal donors (FIG. 23B). The fetal liver clones AC.2 and AC.8 use the invariant Vγ2 chain that is found in 10-30% of adult Vγ2Vδ2 TCR (50). Reactivity to HMBPP by fetal and cord blood clones confirms ours and other's earlier studies showing that cord blood Vγ2Vδ2 T cells respond to HMBPP in mycobacterial lysates and to IPP, and that these responses are present at birth (38, 51-53). These results suggest that reactivity to HMBPP is a property of most Vγ2Vδ2 T cells, including those expressing invariant Vγ2 chains.

Figure 24:
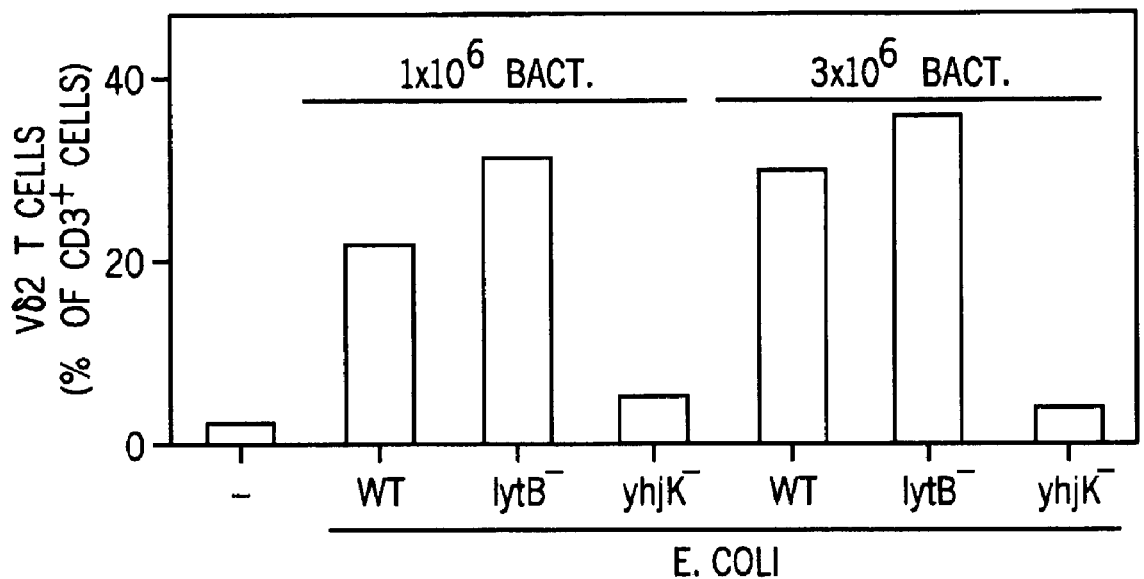
FIG. 24. Bacterial HMBPP levels determine in vitro expansion of Vγ2Vδ2 T cells. 1 or 3×10⁶ live wt or mutant bacteria were added to the inner well of a transwell where they were separated from PBMC in the outer well by a 0.4 µm membrane. After 4 h, the inner wells were removed. On day 6, PBMC were harvested, counted, and Vγ2Vδ2 T cells determined by flow cytometry using anti-Vδ2 and anti-CD3 mAbs. Data shown are from 1 donor and are representative of results with 7 donors.

Bacterial HMBPP Levels Determine the Magnitude of in vitro and in vivo Expansion of Vγ2Vδ2 T Cells If HMBPP is a major determinant of Vγ2Vδ2 T cell reactivity to bacteria, we reasoned that increasing HMBPP levels would results in stronger Vγ2Vδ2 T cell responses. To determine if the levels of HMBPP in bacteria influence Vγ2Vδ2 T-cell expansion in vitro, PBMC were co-cultured with live LytB$^{G120D}$ that overproduce HMBPP, LytB$^{G120D}$ yhjK$^-$ mutant bacteria that had extremely low bioactivity levels, and wild-type bacteria with moderate bioactivity levels in a transwell system. Vγ2Vδ2 T cells expanded slightly more with LytB$^{G120D}$ bacteria than with wild-type, but much less with LytB$^{G120D}$ yhjK$^-$ bacteria that had extremely low levels of bioactivity (FIG. 24).

Since Vγ2Vδ2 T cells and prenyl pyrophosphate recognition is restricted to primates, direct testing in vivo is difficult. The hu-PBL-SCID-beige model provides a small animal model where human PBMC are transplanted into immunodeficient SCID-beige mice. Transplanted Vγ2Vδ2 T cells have been shown to proliferate when preactivated with antigen prior to transplantation where they help provide immunity to infection with bacteria through their production of IFN-γ (16). Therefore, we used this model system to determine the effects of differing levels of bacterial HMBPP on the expansion of Vγ2Vδ2 T cells in vivo.

Figure 25A:
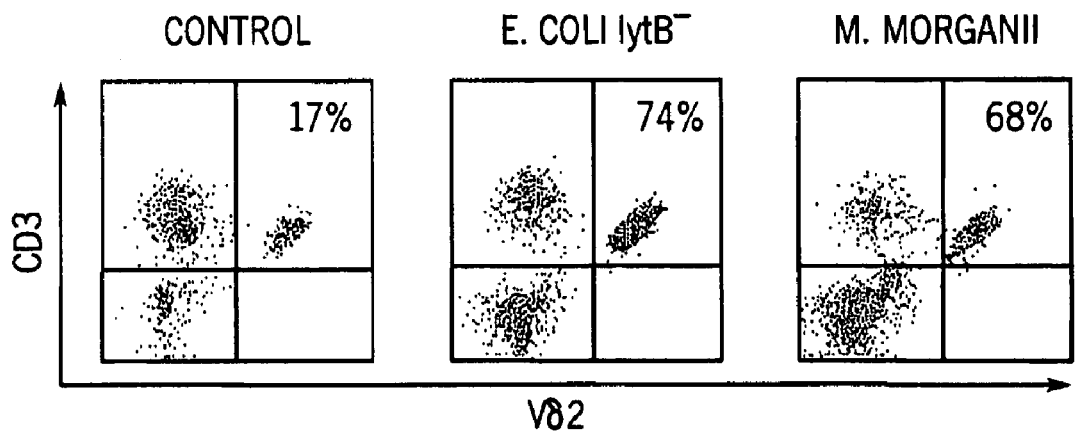
FIG. 25. Bacterial HMBPP levels determine in vivo expansion of unactivated Vγ2Vδ2 T cells in the hu-PBL-SCID-biege mouse model. (A, B) *E. coli* LytB$^{G120D}$ or *Morganella morganii* expand HMBPP-activated Vγ2Vδ2 T cells in a dose dependent manner. SCID-beige mice were reconstituted with 3×10⁷ HMBPP-activated PBMC i.p. and subsequently challenged with increasing numbers of *E. coli* LytB$^{G120D}$ or *M. morganii* bacteria. After 9 days, cells were harvested and Vγ2Vδ2 T cells determined by two-color flow cytometry. (A) Two-color flow cytometric analysis of representative mice with or without bacteria. (B) Bacterial dose response of HMBPP-activated Vγ2Vδ2 T cells. Total Vγ2Vδ2 T cells were up to 3-fold greater in mice receiving bacteria. (C) Expansion of HMBPP-activated Vγ2Vδ2 T cells by both wild type and LytB$^{G120D}$ *E. coli*. SCID-beige mice were reconstituted with HMBPP-activated PBMC as in (A). Note the similar increases in Vδ2+ T cells in mice receiving wild-type bacteria and LytB$^{G120D}$ bacteria that have elevated levels of HMBPP. (D) Expansion of unactivated Vγ2Vδ2 T cells is dependent on HMBPP levels. SCID-beige mice were reconstituted with unactivated PBMC followed by infection with either wild-type or LytB$^{G120D}$ bacteria. Left and right panels represent two independent experiments with three mice per group and ten mice per group respectively. *p<0.01. Note that only mice receiving the LytB$^{G120D}$ bacteria showed expansion of Vγ2Vδ2 T cells.
Figure 25B:
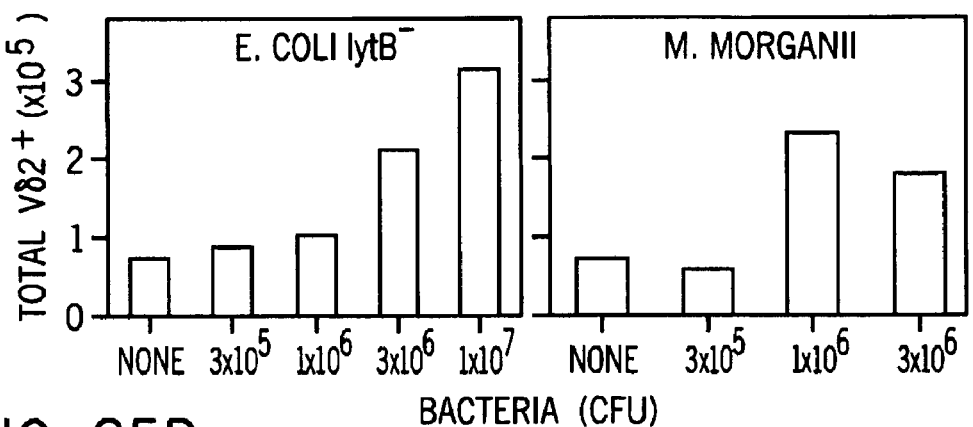
Figure 25C:
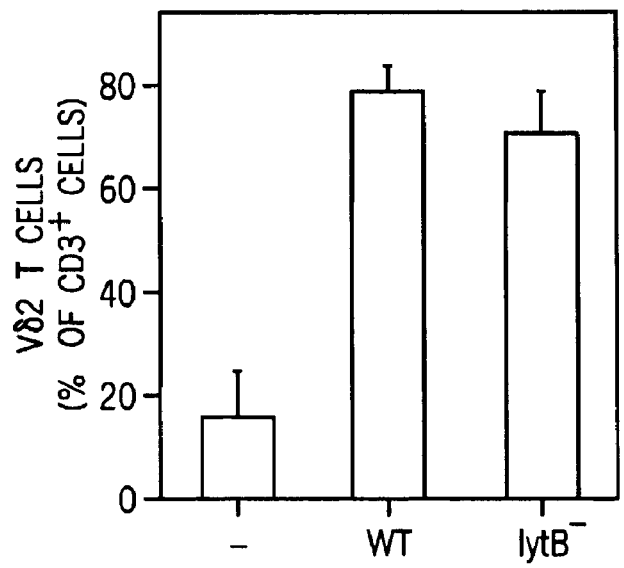

SCID-beige mice were engrafted with HMBPP-activated PBMC (containing 1-5% Vγ2Vδ2$^+$ T cells) and subsequently infected with bacteria. Peritoneal cells were harvested 9 days later and analyzed by flow cytometry. Mice that received HMBPP-activated PBMC, followed by either LytB$^{G120D}$ *E. coli* (that have very high bioactivity) or *Morganella morganii*, (with more modest levels of bioactivity) showed expansion of Vδ2$^+$ T cells that was dose dependent but not significantly different between the two bacteria (FIG. 25A, B). Similarly, wild-type and LytB$^{G120D}$ bacteria elicited roughly similar levels of Vδ2$^+$ T cell expansion. This result is consistent with previous in vitro studies showing that LPS alone could stimulate antigen-activated Vγ2Vδ2 T cells to expand and secrete IFN-γ (54). These findings suggest that after nonpeptide antigen stimulation in vitro subsequent in vivo Vγ2Vδ2 T cell expansion is less dependent on antigen levels.

Figure 25D:
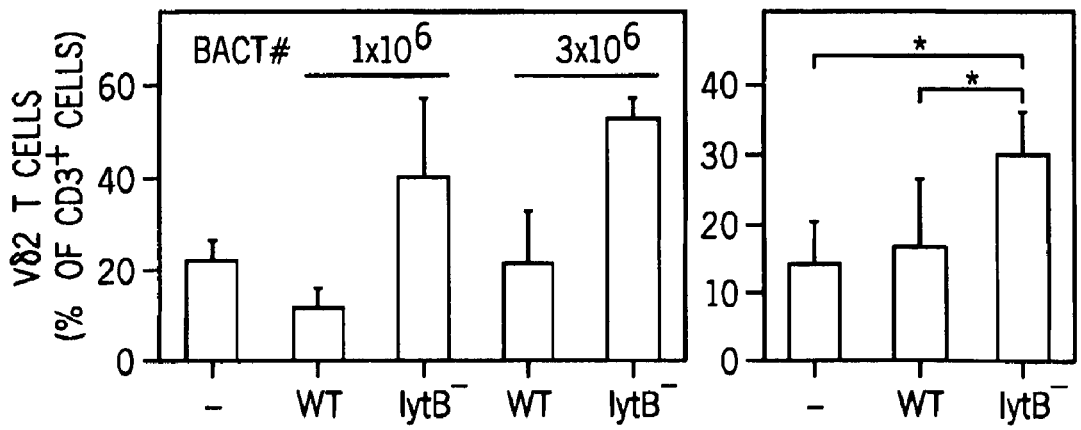

In contrast, when unactivated PBMC were used for engraftment, significantly higher levels of Vδ2$^+$ T cell expansion were found only with infection with LytB$^{G120D}$ *E. coli* as compared to wild-type *E. coli* or non-infected controls (FIG. 25D, right). Vδ2$^+$ T cell expansion was also dependent on bacterial numbers, as shown in an independent experiment with a different donor (FIG. 25D, left). These expansions occurred in the absence of exogenously added IL-2. Thus, bacterial HMBPP levels likely play an important role in determining in vivo responses by Vγ2Vδ2 T cells.

Figure 26:
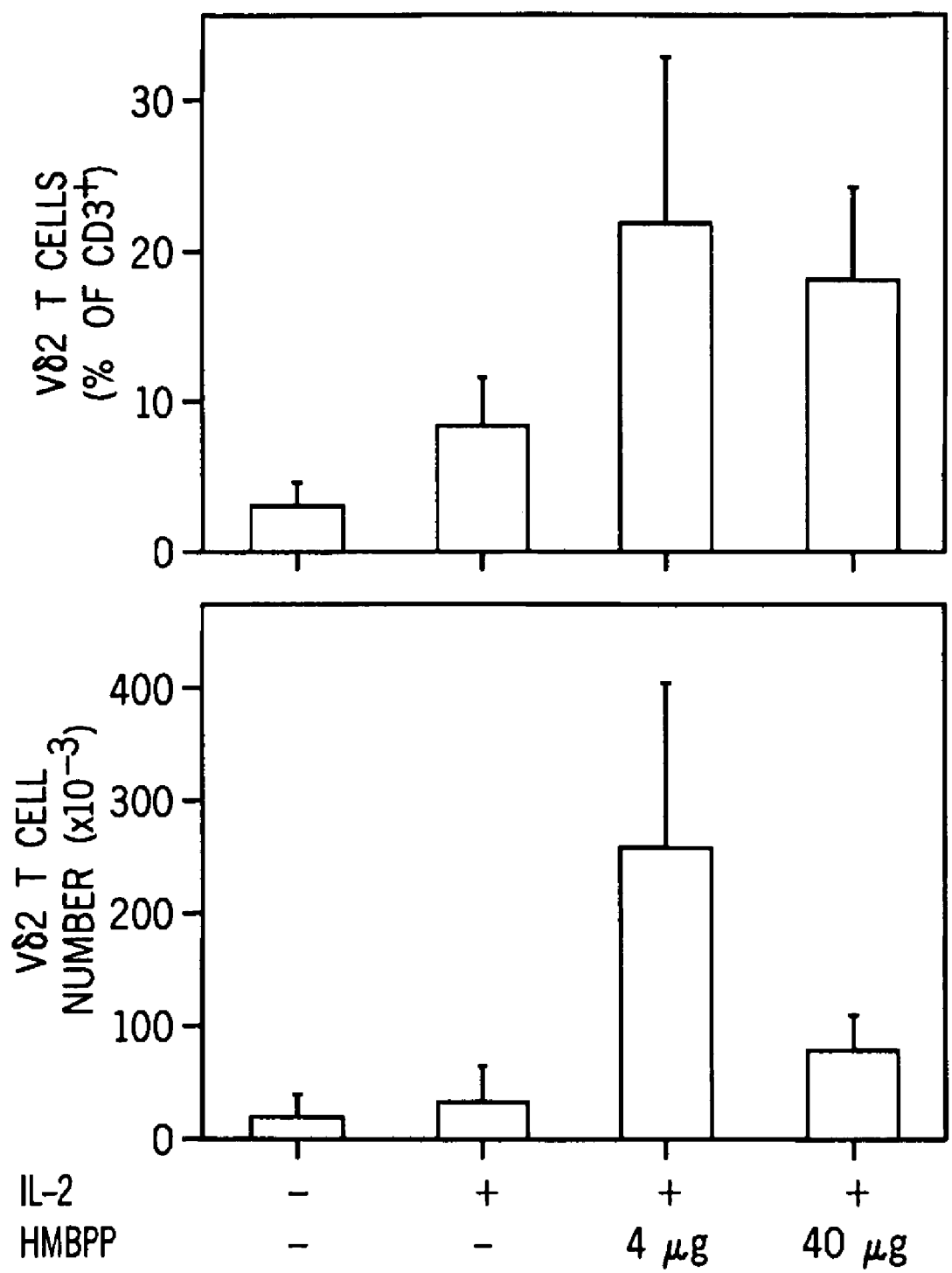
FIG. 26. Synthetic HMBPP stimulates in vivo expansion of Vγ2Vδ2 T cells. SCID-beige mice were reconstituted with 3×10$^7$ unactivated PBMC i.p. and subsequently challenged with varying amounts of HMBPP. 5000 I.U. of human IL-2 was given i.p. every other day starting on day 0. After 9 days, cells were harvested by peritoneal lavage and the expansion of Vγ2Vδ2 T cells assessed by two-color flow cytometry: (top) Vγ2Vδ2 T cells as % of CD3+ T cells; (bottom) total Vγ2Vδ2 T cell numbers. Similar increases in Vγ2Vδ2 T cells (as a % of CD3+ T cells) were noted in two additional experiments.

To determine if HMBPP could directly stimulate Vγ2Vδ2 T cells in vivo, unactivated PBMC were transplanted into SCID-beige mice and then stimulated with synthetic HMBPP. HMBPP stimulated the expansion of resting Vγ2Vδ2 T cells such that their absolute numbers and percentage of CD3 T cells were significantly increased (FIG. 26). Unlike expansions with bacterial infection, this expansion was dependent on exogenous IL-2 (data not shown).

Discussion

In this study, we show that the level of HMBPP in bacteria is a major factor in determining in vivo responses in the hu-PBL-SCID-beige mouse model by Vγ2Vδ2 T cells. We find that HMBPP is the primary antigen for Vγ2Vδ2 T cells in mycobacteria and in the Gram negative rods, *Escherichia coli* and *Yersinia enterocolitica*. We confirm and extend previous studies by showing that mutations in all 6 enzymes upstream of HMBPP in the MEP pathway abolished or greatly diminished bioactivity, whereas mutation of the downstream LytB enzyme greatly increased bioactivity. Infection with the LytB$^{G120D}$ mutant also expanded Vγ2Vδ2 T cells in the hu-PBL-SCID-beige mouse model. The magnitude of the Vγ2Vδ2 T cell expansion was related to the HMBPP levels in the bacteria, and synthetic HMBPP was highly active on a molar basis in stimulating Vγ2Vδ2 T cells both in vitro and in vivo. Since the MEP pathway is widely distributed in many important human pathogens including *Mycobacteria*, Gram-negative bacteria, and apicomplexan protozoa, recognition by Vγ2Vδ2 T cells of a metabolite in this pathway allows Vγ2Vδ2 T cells to combat infection by a broad range of microbial pathogens.

Our study also helps to address the question of the structure of the 262 Dalton phosphoantigen (TUBag1). On transposon mutagenesis of the LytBG$^{120D}$ *E. coli* mutant, no genes were identified that could encode an enzyme that would produce 3-FBPP. Moreover, our studies on synthetic 3-FBPP (35) show that this compound has only low to moderate activity for Vγ2Vδ2 T cells rather than the high activity reported for TUBag1 (29) and has a different NMR spectra than that reported for TUBag1 (29). Similarly, the 275 Dalton compound from mycobacteria that was proposed as 3-formylpentyl pyrophosphate is actually 6-phosphogluconate, a biologically inactive compound (35). Nucleotide conjugated forms of TUBag1 do not contribute significant amounts of bioactivity in both Gram negative rods and rapid growing mycobacteria. Also, none of the other metabolites in the MEP pathway have significant bioactivity for Vγ2Vδ2 T cells (31). Taken together and with other reported genetic studies and structural studies on phosphoantigens (23, 24, 26, 27, 55, 56), we conclude that HMBPP is most likely the 262 Dalton antigen isolated from mycobacteria and from Gram negative rods that use the MEP pathway.

Using transposon and chemical mutagenesis, we have identified all of the genes of enzymes in the MEP pathway as affecting bioactivity levels for Vγ2Vδ2 T cells. Mutations in any of these genes blocked bacterial growth on media without mevalonate, and decreased bioactivity of the LytB$^{G120D}$ mutant to wild-type levels. We also found that the fldA gene, encoding flavodoxin I, was essential both for the MEP pathway and for bioactivity. Flavodoxin contains a flavin mononucleotide and donates electrons to a number of iron-containing proteins (57, 58). One protein that likely requires flavodoxin activity is GcpE, a [4Fe-4S] protein that, via two one-electron transfers, catalyses the synthesis of HMBPP (59). After disrupting the fldA gene, HMBPP was not produced and bacteria stopped growing; complementation of mutants with flavodoxin restored growth (44). LytB is also a [4Fe-4S] protein (60) and flavodoxin may be required for its enzymatic activity. Although the mutants had lower bioactivity for Vγ2Vδ2 T cells, the ability of mutant bacteria to stimulate Vγ2Vδ2 T cells was not completely abolished. This bioactivity is probably due to either HMBPP produced by residual MEP enzyme activity or to IPP. Consistent with this latter hypothesis, Eubacteria that use the mevalonate pathway, such as *Staphylococcus* and *Streptococcus*, also contain a phosphoantigen that is likely to be IPP (unpublished data, 33, 34).

The Vγ2Vδ2 TCR mediates recognition of HMBPP (61) and Vγ2Vδ2 T cells do not require antigenic selection to enrich for rare reactive clones. We previously showed that in cord blood, Vγ2Vδ2 T cells expand to high numbers when cultured with *M. tuberculosis* lysates (51) and that cord blood Vγ2Vδ2 T cell clones isolated without antigenic stimulation respond to nonpeptide antigens (38). Here we demonstrate that fetal liver clones and a cord blood clone respond to HMBPP like adult Vγ2Vδ2 T cells. This strong reactivity for HMBPP is found in many cord blood and fetal Vγ2Vδ2 clones (38) including those carrying the germline encoded invariant Vγ2 gene sequence (such as AC.2 and AC.8) (50). This invariant Vγ2 junctional sequence is commonly expressed by Vγ2Vδ2 T cells since it was found in 11-30% of Vγ2Jγ1.2 rearrangements from 9 children (50), in 10-17.6% of Vγ2Jγ1.2 rearrangements from 5 adults (62), and in 6.5% of functional Vγ2Jγ1.2 rearrangements before and 11.9% after IPP stimulation of 1 donor (63). There is also likely to be selection for more reactive Vγ2Vδ2 T cells during infancy as evidenced by the predominance of Vγ2Vδ2 T cells expressing Vγ2 chains using the Jγ1.2 region and with a hydrophobic residue in the CDR3δ region that are not commonly seen in fetal Vγ2Vδ2 T cells (64).

A recent estimate of precursor frequency of naive CD8 T cells specific for the H-2 D$^b$-restricted GP33-41 epitope of lymphocytic choriomeningitis virus was 1 in 200,000 (65), whereas Vγ2Vδ2 T cells constitute 1 in 618 T cells in cord blood (38) and 1 in 25-100 T cells in adults HMBPP (1, 66, 67). Since most Vγ2Vδ2 T cell clones isolated from adults by sorting and lectin stimulation respond to mycobacterial lysates (10 reactive/10 clones, C. M. unpublished observation, 11/14 clones (68), and 25/26 clones (67) for 46/50 clones (92%)), it is likely that the majority of adult Vγ2Vδ2 T cells respond to HMBPP. Thus, unlike αβ T cells specific for peptides, a previous encounter with a specific bacteria is not required to amplify adult HMBPP-specific Vγ2Vδ2 T cells since earlier infections or exposure to endogenous IPP has amplified further the already high percentage of reactive Vγ2Vδ2 T cells (69). This ability of Vγ2Vδ2 T cells to recognize HMBPP may be vital in containing infections prior to the onset of adaptive αβ T cell and B-cell responses.

Since murine γδ T cells do not respond to prenyl pyrophosphate antigen, the hu-PBL-SCID-beige mouse model offers a small animal model to study human Vγ2Vδ2 T cell functions in vivo. Previous studies using the hu-PBL-SCID model frequently relied on the prior activation of PBMC in vitro with an agonistic anti-CD3 antibody (70). In another study, Vγ2Vδ2 T cells were activated in vitro with the alkylamine, isobutylamine, prior to transfer to generate Vγ2Vδ2 T cell responses in vivo (16). Activating PBMC with HMBPP in vitro increased the responsiveness of the Vγ2Vδ2 T cells to subsequent infection with different *E. coli* bacteria. This is analogous to CD8$^+$ αβ T cells where initial priming with antigen ex vivo sensitizes them for greater proliferation and differentiation (71, 72). In contrast, the elevated levels of HMBPP found with mutant LytB$^{G120D}$ *E. coli* stimulated Vγ2Vδ2 T cell expansion in SCID-beige mice engrafted without requiring preactivation with antigen or exogenously added IL-2. Similarly, synthetic HMBPP was able to expand transferred Vγ2Vδ2 T cells in hu-PBL-SCID-beige mice but this expansion required exogenously added IL-2 similar to the requirement noted for in vivo stimulation of primates and human Vγ2Vδ2 T cells (73-75).

Despite their broad reactivity for prenyl pyrophosphates, our study shows that Vγ2Vδ2 T cells can distinguish between foreign (HMBPP) and self (IPP) phosphoantigens that are structurally very similar. Although both IPP and HMBPP stimulate similar responses at optimal concentrations, HMBPP is ~30,000-fold more potent on a molar basis. This recognition of HMBPP can be mediated by Vγ2Vδ2 TCRs using a germline encoded, invariant Vγ2 chain allowing a significant proportion of cord blood Vγ2Vδ2 T cells to recognize foreign pathogens. Furthermore, Vγ2Vδ2 T cells expand early (between the age of 1-3 years (69)) leading to their conversion to a memory phenotype. As a result, by adulthood over 98% of circulating Vγ2Vδ2 T cells are memory T cells (data not shown and 76). Thus, in humans over 3 years old, Vγ2Vδ2 T cells can mount memory responses to primary infections of bacteria and protozoa for which the rest of the adaptive immune system (αβ T cells and follicular B cells) is naïve. This ability parallels that of marginal zone B cells that are programmed to mount rapid and intense antibody responses to blood-borne pathogens (77, 78). Similar to Vγ2Vδ2 T cells, some marginal zone B cells use their invariant or $V_H$-restricted antibody receptors to recognize non-peptide antigens found in both pathogens and self. But for some marginal zone B cells the targets are phosphorylcholine (phospholipids) or polysaccharide compounds (79).

The ability of Vγ2Vδ2 T cells to preferentially recognize a foreign metabolite is also reminiscent of pattern recognition by Toll-like receptors (TLR) of the innate immune system. Each TLR recognizes conserved structures produced by or in response to different microbes (80). Moreover, like Vγ2Vδ2 TCR recognition of endogenous IPP, some TLRs, such as TLR9, also recognize endogenous DNA under certain conditions (81). The microbial TLR ligands are abundant, distributed in a wide array of microorganisms, and predominantly non-peptidic. Similarly, HMBPP is present in a wide array of both prokaryotic and eukaryotic microorganisms that use the MEP pathway. Vγ2Vδ2 T cells also express TLR2 and the recognition of nonpeptide antigens is enhanced by the presence of TLR ligands either directly (82) or indirectly through their stimulation of IFN-α/β from antigen presenting cells (83, 84).

Vγ2Vδ2 T cells may be particularly important in immunity to infections caused by intracellular bacteria or protozoa that subvert the innate and adaptive immune systems. Many of the infections that expand Vγ2Vδ2 T cells are by intracellular microbes (reviewed in 85, 86) and the expansion of Vγ2Vδ2 T cells correlated with clearance of mycobacteria in rhesus monkeys (17). In the hu-PBL-SCID mouse model, Vγ2Vδ2 T cells also help to protect mice from infections with E. coli, S. aureus, and M. morganii by the production IFN-γ and other cytokines (16). Vγ2Vδ2 T cells can recognize cells infected with M. tuberculosis, M. bovis BCG, and Salmonella typhimurium (7, 87-89) and kill the infected cells through perforin- and Fas ligand-dependent pathways (90-93). Released bacteria and malarial parasites can then be killed by granulysin (88, 90, 93-97). Activated Vγ2Vδ2 T cells secrete a variety of cytokines and chemokines (chemokine production is reviewed in 98). Most Vγ2Vδ2 T cells secrete $T_H1$ cytokines such as IFN-γ, TNF-α, and other inflammatory cytokines (37, 99). They also secrete inflammatory chemokines such as MIP-1α (CCL3), MIP-1β (CCL4), lymphotactin (XCL1), and RANTES (CCL5) (100-102). Vγ2Vδ2 T cells can also kill bacteria by secreting the cathelicidin, LL-37, which has an anti-bacterial effect on Brucella suis (103). Besides their direct role in microbial immunity, Vγ2Vδ2 T cells may also be important for the maintenance of tissue integrity and to speed tissue repair through the production of connective tissue growth factors (104, 105) and metalloproteinases (106). They may also serve to regulate αβ T cell and innate immune responses as has been shown in mice (reviewed in 107, 108).

Besides responding to HMBPP, Vγ2Vδ2 T cells also recognize the endogenous IPP metabolite when overproduced by certain tumor cells (109) or by pharmacological inhibition of farnesyl pyrophosphate synthase by bisphosphonates or alkylamines (109-111). This overproduction of IPP appears to determine Vγ2Vδ2 T cell recognition of some B cell tumors (109). Vγ2Vδ2 T cells also recognize and kill a wide variety of tumor cells including prostate carcinomas, renal cell carcinomas, nasopharyngeal carcinomas, and colon carcinomas probably through non-TCR mediated, NK receptor recognition (112-116). Since immunotherapy with Vγ2Vδ2 T cells can control B cell malignancies (75), Vγ2Vδ2 T cells may naturally perform tumor surveillance and could be used for immunotherapy of a number of different cancers.

In summary, the preferential recognition of the exogenous isoprenoid metabolite, HMBPP, over endogenous isoprenoids is likely to play a central role in the immune function of Vγ2Vδ2 T cells and parallels antigen recognition by adaptive marginal zone B cells and pattern recognition by innate cells. Exploiting this unique property of Vγ2Vδ2 T cells may result in new vaccines for bacterial infections and new immunotherapies for malignancies.

All publications and patent applications cited in this specification are herein incorporated by reference as if each individual publication or patent application were specifically and individually indicated to be incorporated by reference.

TABLE I

Mutations in enzymes in the MEP pathway of E. coli K12 W3110

| Gene | Name | Mutation | Mutation Location | Growth w/o mevalonate[a] | Bioactivity (U/L) |
|---|---|---|---|---|---|
| — | wt | none | — | ++++ | 18,182 |
| dxr | W3110 dxr⁻ | insertion of a kanamycin resistance gene | BalI site, nucleotide 365-370 | ++[b] | 26,087 |
| ygbP | NMW33 | single point | $^{120}$L (TTG) to $^{120}$F (TTT) | ++ | 26,087 |
| ygbP | NMW34 | stop codon | $^{28}$Q (CAA) to Stop codon (TAA) | − | 2,800 |
| ychB | NMW29 | double point | $^{112}$A (GCC) to $^{112}$V (GTC) and $^{153}$A (GCC) to $^{153}$V (GTC) | ++ | 20,000 |

TABLE I-continued

Mutations in enzymes in the MEP pathway of *E. coli* K12 W3110

| Gene | Name | Mutation | Mutation Location | Growth w/o mevalonate[a] | Bioactivity (U/L) |
|---|---|---|---|---|---|
| ygbB | NMW25 | stop codon | $^{81}$W (TGG) to Stop codon (TGA) | − | 1,096 |
| ygbB | NMW31 | single point | $^{21}$G (GGT) to $^{21}$D (GAT) | ++ | 20,000 |
| gcpE | NMW12 | single point | $^{139}$G (GGA) to $^{139}$Q (GAA) | − | <100 |
| gcpE | NMW15 | single point | $^{133}$R (CGT) to $^{133}$C (TGT) | − | 1,044 |
| gcpE | NMW19 | single point | $^{211}$S (TCC) to $^{211}$F (TTC) | + | 54,545 |
| lytB[c] | LytB$^{G120D}$ | single point | $^{120}$G (GST) to $^{120}$D(GAT) | + | 6,369,231 |

[a]Growth was assessed in the absence of mevalonate by incubating plates overnight at 37° C. and then sealing and incubating at room temperature for 10 days. Note that mutations that allow growth are associated with wild-type levels of bioactivity. Bacterial colony size 4+ = >8 mm; 3+ = 6-8 mm; 2+ = 4-6 mm; 1+ = 1-4 mm.
[b]Growth of the dxr⁻ strain is due to the presence of low numbers of revertants.
[c]LytB mutant was strain DK310 LytB$^{G120D}$ (pTMV20KM).

TABLE II

Transposon mutants of DK310 LytB$^{G120D}$ *E. coli* bacteria[a]

| Gene | # of isolates | Product | Fold reduction in Vγ2Vδ2 T cell bioactivity | Mevalonate required for growth | Function |
|---|---|---|---|---|---|
| tpi | 1 | triose phosphate isomerase | 8 | no | isomerizes dihydroxy-acetone-phosphate to glyceraldehyde-3-phosphate |
| dxs | 14 | deoxyxylulose synthase | 1,183 | yes | synthesizes deoxyyxlulose-5-phosphate |
| dxr | 1 | deoxyxylulose reductoisomerase | 1,650 | yes | synthesizes ME4P |
| ychB | 2 | CDP-ME kinase | 6,822 | yes | synthesizes CDP-ME2P |
| ygbB | 2 | MECDP synthase | 1,650 | yes | synthesizes ME-2,4cPP |
| gcpE | 4 | HMBPP synthase | 7,226 | yes | synthesizes HMBPP |
| fldA | 1 | flavodoxin A | 374 | yes | electron transferase |
| sppA | 1 | signal peptide protease A | 220 | yes | signal peptide protease |
| yhjK | 1 | transmembrane receptor | 24,220 | no | regulates c-di-GMP levels |
| yaeD | 1 | phosphatase | 1 | yes | cell wall synthesis |
| cysB | 1 | transcription factor | 0 | yes | regulates cysteine synthesis |

[a]Abbreviations used:
c-di-GMP, cyclic diguanylate guanosine monophosphate;
CDP-ME, 4-diphosphocytidyl-2-C-methyl-D-erythritol;
MECDP, 2-C-methyl-D-erythritol 2,4-cyclodiphosphate;
ME-2,4cPP, 2-C-methyl-D-erythritol 2,4-cyclodiphosphate;
HMBPP, (E)-4-hydroxy-3-methyl-but-2-enyl diphosphate.

NUMERICAL REFERENCES OF EXAMPLE 3

1 Tanaka, Y., Sano, S., Nieves, E., De Libero, G., Roca, D., Modlin, R. L., Brenner, M. B., Bloom, B. R., and Morita, C. T. 1994. Nonpeptide ligands for human γδ T cells. *Proc. Natl. Acad. Sci. USA* 91:8175.

2 Tanaka, Y., Morita, C. T., Tanaka, Y., Nieves, E., Brenner, M. B., and Bloom, B. R. 1995. Natural and synthetic nonpeptide antigens recognized by human γδ T cells. *Nature* 375:155.

3 Balbi, B., Moller, D. R., Kirby, M., Holroyd, K. J., and Crystal, R. G. 1990. Increased numbers of T lymphocytes with γδ-positive antigen receptors in a subgroup of individuals with pulmonary sarcoidosis. *J. Clin. Invest.* 85:1353.

4 Balbi, B., Valle, M. T., Oddera, S., Giunti, D., Manca, F., Rossi, G. A., and Allegra, L. 1993. T-lymphocytes with γδ⁺ Vδ2⁺ antigen receptors are present in increased proportions in a fraction of patients with tuberculosis or with sarcoidosis. *Am. Rev. Respir. Dis.* 148:1685.

5 Barnes, P. F., Grisso, C. L., Abrams, J. S., Band, H., Rea, T. H., and Modlin, R. L. 1992. γδ T lymphocytes in human tuberculosis. *J. Infect. Dis.* 165:506.

6 Modlin, R. L., Pirmez, C., Hofman, F. M., Torigian, V., Uyemura, K., Rea, T. H., Bloom, B. R., and Brenner, M. B. 1989. Lymphocytes bearing antigen-specific γδ T-cell receptors accumulate in human infectious disease lesions. *Nature* 339:544.

7 Hara, T., Mizuno, Y., Takaki, K., Takada, H., Akeda, H., Aoki, T., Nagata, M., Ueda, K., Matsuzaki, G., Yoshikai, Y., and Nomoto, K. 1992. Predominant activation and expansion of Vγ9-bearing γδ cells in vivo as well as in vitro in *Salmonella* infection. *J. Clin. Invest.* 90:204.

8 Bertotto, A., Gerli, R., Spinozzi, F., Muscat, C., Scalise, F., Castellucci, G., Sposito, M., Candio, F., and Vaccaro, R. 1993. Lymphocytes bearing the γδ T cell receptor in acute *Brucella melitensis* infection. *Eur. J. Immunol.* 23:1177.

9 Poquet, Y., Kroca, M., Halary, F., Stenmark, S., Peyrat, M.-A., Bonneville, M., Fournié, J. J., and Sjöstedt, A. 1998. Expansion of Vγ9Vδ2 T cells is triggered by *Francisella tularensis*-derived phosphoantigens in tularemia but not after tularemia vaccination. *Infect. Immun.* 66:2107.

10 Sumida, T., Maeda, T., Takahashi, H., Yoshida, S., Yonaha, F., Sakamoto, A., Tomioka, H., Koike, T., and Yoshida, S. 1992. Predominant expansion of Vγ9/Vδ2 T cells in a tularemia patient. *Infect. Immun.* 60:2554.

11 Kroca, M., Tärnvik, A., and Sjöstedt, A. 2000. The proportion of circulating γδT cells increases after the first week of onset of tularaemia and remains elevated for more than a year. *Clin. Exp. Immunol.* 120:280.

12. Caldwell, C. W., Everett, E. D., McDonald, G., Yesus, Y. W., and Roland, W. E. 1995. Lymphocytosis of γ/δ T cells in human ehrlichiosis. *Am. J. Clin. Pathol.* 103:761.
13. Ho, M., Webster, H. K., Tongtawe, P., Pattanapanyasat, K., and Weidanz, W. P. 1990. Increased γδ T cells in acute *Plasmodium falciparum* malaria. *Immunol. Lett.* 25:139.
14. Perera, M. K., Carter, R., Goonewardene, R., and Mendis, K. N. 1994. Transient increase in circulating γ/δ T cells during *Plasmodium vivax* malarial paroxysms. *J. Exp. Med.* 179:311.
15. Scalise, F., Gerli, R., Castellucci, G., Spinozzi, F., Fabietti, G. M., Crupi, S., Sensi, L., Britta, R., Vaccaro, R., and Bertotto, A. 1992. Lymphocytes bearing the γδ T-cell receptor in acute toxoplasmosis. *Immunology* 76:668.
16. Wang, L., Kamath, A., Das, H., Li, L., and Bukowski, J. F. 2001. Antibacterial effect of human Vγ2Vδ2 T cells in vivo. *J. Clin. Invest.* 108:1349.
17. Shen, Y., Zhou, D., Qiu, L., Lai, X., Simon, M., Shen, L., Kou, Z., Wang, Q., Jiang, L., Estep, J., Hunt, R., Clagett, M., Sehgal, P. K., Li, Y., Zeng, X., Morita, C. T., Brenner, M. B., Letvin, N. L., and Chen, Z. W. 2002. Adaptive immune response of Vγ2Vδ2+ T cells during mycobacterial infections. *Science* 295:2255.
18. Eberl, M., Hintz, M., Reichenberg, A., Kollas, A.-K., Wiesner, J., and Jomaa, H. 2003. Microbial isoprenoid biosynthesis and human γδ T cell activation. *FEBS Lett.* 544:4.
19. Rohmer, M. 2003. Mevalonate-independent methylerythritol phosphate pathway for isoprenoid biosynthesis. Elucidation and distribution. *Pure Appl. Chem.* 75:375.
20. Eisenreich, W., Bacher, A., Arigoni, D., and Rohdich, F. 2004. Biosynthesis of isoprenoids via the non-mevalonate pathway. *Cell. Mol. Life. Sci.* 61:1401.
21. Hecht, S., Eisenreich, W., Adam, P., Amslinger, S., Kis, K., Bacher, A., Arigoni, D., and Rohdich, F. 2001. Studies on the nonmevalonate pathway to terpenes: the role of the GcpE (IspG) protein. *Proc. Natl. Acad. Sci. USA* 98:14837.
22. Rohdich, F., Hecht, S., Gartner, K., Adam, P., Krieger, C., Amslinger, S., Arigoni, D., Bacher, A., and Eisenreich, W. 2002. Studies on the nonmevalonate terpene biosynthetic pathway: metabolic role of IspH (LytB) protein. *Proc. Natl. Acad. Sci. USA* 99:1158.
23. Hintz, M., Reichenberg, A., Altincicek, B., Bahr, U., Gschwind, R. M., Kollas, A.-K., Beck, E., Wiesner, J., Eberl, M., and Jomaa, H. 2001. Identification of (E)-4-hydroxy-3-methyl-but-2-enyl pyrophosphate as a major activator for human γδ T cells in *Escherichia coli*. *FEBS Lett.* 509:317.
24. Altincicek, B., Moll, J., Campos, N., Foerster, G., Beck, E., Hoeffler, J. F., Grosdemange-Billiard, C., Rodríguez-Concepción, M., Rohmer, M., Boronat, A., Eberl, M., and Jomaa, H. 2001. Human γδ T cells are activated by intermediates of the 2-C-methyl-D-erythritol 4-phosphate pathway of isoprenoid biosynthesis. *J. Immunol.* 166:3655.
25. Eberl, M., Altincicek, B., Kollas, A.-K., Sanderbrand, S., Bahr, U., Reichenberg, A., Beck, E., Foster, D., Wiesner, J., Hintz, M., and Jomaa, H. 2002. Accumulation of a potent γδ T-cell stimulator after deletion of the lytB gene in *Escherichia coli*. *Immunology* 106:200.
26. Eberl, M., Hintz, M., Jamba, Z., Beck, E., Jomaa, H., and Christiansen, G. 2004. *Mycoplasma penetrans* is capable of activating Vγ9/Vδ2 T cells while other human pathogenic mycoplasmas fail to do so. *Infect. Immun.* 72:4881.
27. Begley, M., Gahan, C. G., Kollas, A.-K., Hintz, M., Hill, C., Jomaa, H., and Eberl, M. 2004. The interplay between classical and alternative isoprenoid biosynthesis controls γδ T cell bioactivity of *Listeria monocytogenes*. *FEBS Lett.* 561:99.
28. Constant, P., Davodeau, F., Peyrat, M.-A., Poquet, Y., Puzo, G., Bonneville, M., and Fournié, J.-J. 1994. Stimulation of human γδ T cells by nonpeptidic mycobacterial ligands. *Science* 264:267.
29. Belmant, C., Espinosa, E., Poupot, R., Peyrat, M.-A., Guiraud, M., Poquet, Y., Bonneville, M., and Fournié, J.-J. 1999. 3-formyl-1-butyl pyrophosphate a novel mycobacterial metabolite-activating human γδ T cells. *J. Biol. Chem.* 274:32079.
30. Poquet, Y., Constant, P., Halary, F., Peyrat, M.-A., Gilleron, M., Davodeau, F., Bonneville, M., and Fournié, J.-J. 1996. A novel nucleotide-containing antigen for human blood γδ T lymphocytes. *Eur. J. Immunol.* 26:2344.
31. Feurle, J., Espinosa, E., Eckstein, S., Pont, F., Kunzmann, V., Fournié, J. J., Herderich, M., and Wilhelm, M. 2002. *Escherichia coli* produces phosphoantigens activating human γδ T cells. *J. Biol. Chem.* 277:148.
32. Pont, F., Luciani, B., Belmant, C., and Fournié, J. J. 2001. Characterization of phosphoantigens by high-performance anion-exchange chromatography-electrospray ionization ion trap mass spectrometry and nanoelectrospray ionization ion trap mass spectrometry. *Anal. Chem.* 73:3562.
33. Munk, M. E., Gatrill, A. J., and Kaufmann, S. H. E. 1990. Target cell lysis and IL-2 secretion by γ/δ T lymphocytes after activation with bacteria. *J. Immunol.* 145:2434.
34. Bender, A. and Kabelitz, D. 1992. Preferential activation of peripheral blood Vγ9+ γ/δ T cells by group A, B and C but not group D or F streptococci. *Clin. Exp. Immunol.* 89:301.
35. Zhang, Y., Y., S., Yin, F., Broderick, E., Siegel, K., Goddard, A., Nieves, E., Pasa-Tolic, L., Tanaka, Y., Wang, H., Morita, C. T., and Oldfield, E. 2006. Structural studies of Vγ2Vδ2 T cell phosphoantigens. *Chem. Biol.* 13:985.
36. Giner, J.-L. 2002. A convenient synthesis of (E)-4-hydroxy-3-methyl-2-butenyl pyrophosphate and its [4-$^{13}$C]-labeled form. *Tetrahedron Lett.* 43:5457.
37. Morita, C. T., Verma, S., Aparicio, P., Martinez-A., C., Spits, H., and Brenner, M. B. 1991. Functionally distinct subsets of human γ/δ T cells. *Eur. J. Immunol.* 21:2999.
38. Morita, C. T., Parker, C. M., Brenner, M. B., and Band, H. 1994. T cell receptor usage and functional capabilities of human γδ T cells at birth. *J. Immunol.* 153:3979.
39. Takahashi, S., Kuzuyama, T., Watanabe, H., and Seto, H. 1998. A 1-deoxy-D-xylulose 5-phosphate reductoisomerase catalyzing the formation of 2-C-methyl-D-erythritol 4-phosphate in an alternative nonmevalonate pathway for terpenoid biosynthesis. *Proc. Natl. Acad. Sci. USA* 95:9879.
40. Takagi, M., Kuzuyama, T., Kaneda, K., Watanabe, H., Dairi, T., and Seto, H. 2000. Studies on the nonmevalonate pathway: formation of 2-C-methyl-D-erythritol 2,4-cyclodiphosphate from 2-phospho-4-(cytidine 5'-diphospho)-2-C-methyl-D-erythritol. *Tetrahedron Lett.* 41:3395.
41. Kuzuyama, T., Takagi, M., Kaneda, K., Watanabe, H., Dairi, T., and Seto, H. 2000. Studies on the nonmevalonate pathway: conversion of 4-(cytidine 5'-diphospho)-2-C-methyl-D-erythritol to its 2-phospho derivative by 4-(cytidine 5'-diphospho)-2-C-methyl-D-erythritol kinase. *Tetrahedron Lett.* 41:2925.
42. Kuzuyama, T., Takagi, M., Kaneda, K., Dairi, T., and Seto, H. 2000. Formation of 4-(cytidine 5'-diphospho)-2-C-methyl-D-erythritol from 2-C-methyl-D-erythritol 4-phosphate by 2-C-methyl-D-erythritol 4-phosphate cytidylyltransferase, a new enzyme in the nonmevalonate pathway. *Tetrahedron Lett.* 41:703.

43. Kaneda, K., Kuzuyama, T., Takagi, M., Hayakawa, Y., and Seto, H. 2001. An unusual isopentenyl diphosphate isomerase found in the mevalonate pathway gene cluster from *Streptomyces* sp. strain CL190. *Proc. Natl. Acad. Sci. USA* 98:932.

44. Puan, K.-J., Wang, H., Dairi, T., Kuzuyama, T., and Morita, C. T. 2005. fldA is an essential gene required in the 2-C-methyl-D-erythritol 4-phosphate pathway for isoprenoid biosynthesis. *FEBS Lett.* 579:3802.

45. Kuzuyama, T., Takahashi, S., and Seto, H. 1999. Construction and characterization of *Escherichia coli* disruptants defective in the yaeM gene. *Biosci. Biotechnol. Biochem.* 63:776.

46. Hacker, G., Kromer, S., Heeg, K., Ivanyi, J., Wagner, H., and Pfeffer, K. 1992. Opportunist mycobacteria express ligands that stimulate production of human Vγ9Vδ2 T lymphocytes. *Infect. Immun.* 60:2753.

47. Pfeffer, K., Schoel, B., Gulle, H., Kaufmann, S. H. E., and Wagner, H. 1990. Primary responses of human T cells to mycobacteria: a frequent set of γ/δ T cells are stimulated by protease-resistant ligands. *Eur. J. Immunol.* 20:1175.

48. Pfeffer, K., Schoel, B., Plesnila, N., Lipford, G. B., Kromer, S., Deusch, K., and Wagner, H. 1992. A lectin-binding, protease-resistant mycobacterial ligand specifically activates Vγ9+ human γδ T cells. *J. Immunol.* 148: 575.

49. Morita, C. T., Beckman, E. M., Bukowski, J. F., Tanaka, Y., Band, H., Bloom, B. R., Golan, D. E., and Brenner, M. B. 1995. Direct presentation of nonpeptide prenyl pyrophosphate antigens to human γδ T cells. *Immunity* 3:495.

50. Delfau, M.-H., Hance, A. J., Lecossier, D., Vilmer, E., and Grandchamp, B. 1992. Restricted diversity of Vγ9-JP rearrangements in unstimulated human γ/δ T lymphocytes. *Eur. J. Immunol.* 22:2437.

51. Panchamoorthy, G., McLean, J., Modlin, R. L., Morita, C. T., Ishikawa, S., Brenner, M. B., and Band, H. 1991. A predominance of the T cell receptor Vγ9Vδ2 subset in human mycobacteria-responsive T cells suggests germline gene encoded recognition. *J. Immunol.* 147:3360.

52. Fisch, P., Malkovsky, M., Kovats, S., Sturm, E., Braakman, E., Klein, B. S., Voss, S. D., Morrissey, L. W., DeMars, R., Welch, W. J., Bolhuis, R. L. H., and Sondel, P. M. 1990. Recognition by human Vγ9/Vδ2 T cells of a GroEL homolog on Daudi Burkitt's lymphoma cells. *Science* 250: 1269.

53. Montesano, C., Gioia, C., Martini, F., Agrati, C., Cairo, C., Pucillo, L. P., Colizzi, V., and Poccia, F. 2001. Antiviral activity and anergy of γδ T lymphocytes in cord blood and immuno-compromised host. *J. Biol. Regul. Homeost. Agents* 15:257.

54. Wang, L., Das, H., Kamath, A., Li, L., and Bukowski, J. F. 2002. Human Vγ2Vδ2 T cells augment migration-inhibitory factor secretion and counteract the inhibitory effect of glucocorticoids on IL-1β and TNF-α production. *J. Immunol.* 168:4889.

55. Jomaa, H., Feurle, J., Luhs, K., Kunzmann, V., Tony, H. P., Herderich, M., and Wilhelm, M. 1999. Vγ9/Vδ2 T cell activation induced by bacterial low molecular mass compounds depends on the 1-deoxy-D-xylulose 5-phosphate pathway of isoprenoid biosynthesis. *FEMS Immunol Med Microbiol* 25:371.

56. Reichenberg, A., Hintz, M., Kletschek, Y., Kuhl, T., Haug, C., Engel, R., Moll, J., Ostrovsky, D. N., Jomaa, H., and Eberl, M. 2003. Replacing the pyrophosphate group of HMB-PP by a diphosphonate function abrogates its potential to activate human γδ T cells but does not lead to competitive antagonism. *Bioorg. Med. Chem. Lett.* 13:1257.

57. Simondsen, R. P. and Tollin, G. 1980. Structure-function relations in flavodoxin. *Mol. Cell. Biochem.* 33:13.

58. Osborne, C., Chen, L. M., and Matthews, R. G. 1991. Isolation, cloning, mapping, and nucleotide sequencing of the gene encoding flavodoxin in *Escherichia coli*. *J. Bacteriol.* 173:1729.

59. Seemann, M., Bui, B. T., Wolff, M., Tritsch, D., Campos, N., Boronat, A., Marquet, A., and Rohmer, M. 2002. Isoprenoid biosynthesis through the methylerythritol phosphate pathway: the (E)-4-hydroxy-3-methylbut-2-enyl diphosphate synthase (GcpE) is a [4Fe-4S] protein. *Angew. Chem. Int. Ed. Engl.* 41:4337.

60. Gräwert, T., Kaiser, J., Zepeck, F., Laupitz, R., Hecht, S., Amslinger, S., Schramek, N., Schleicher, E., Weber, S., Haslbeck, M., Buchner, J., Rieder, C., Arigoni, D., Bacher, A., Eisenreich, W., and Rohdich, F. 2004. IspH protein of *Escherichia coli*: studies on iron-sulfur cluster implementation and catalysis. *J. Am. Chem. Soc.* 126:12847.

61. Bukowski, J. F., Morita, C. T., Tanaka, Y., Bloom, B. R., Brenner, M. B., and Band, H. 1995. Vγ2Vδ2 TCR-dependent recognition of non-peptide antigens and Daudi cells analyzed by TCR gene transfer. *J. Immunol.* 154:998.

62. Tamura, N., Holroyd, K. J., Banks, T., Kirby, M., Okayama, H., and Crystal, R. G. 1990. Diversity in junctional sequences associated with the common human Vγ9 and Vδ2 gene segments in normal blood and lung compared with the limited diversity in a granulomatous disease. *J. Exp. Med.* 172:169.

63. Evans, P. S., Enders, P. J., Yin, C., Ruckwardt, T. J., Malkovsky, M., and Pauza, C. D. 2001. In vitro stimulation with a non-peptidic alkylphosphate expands cells expressing Vγ2-Jγ1.2/Vδ2 T-cell receptors. *Immunology* 104:19.

64. Davodeau, F., Peyrat, M. A., Hallet, M. M., Houde, I., Vie, H., and Bonneville, M. 1993. Peripheral selection of antigen receptor junctional features in a major human γδ subset. *Eur. J. Immunol.* 23:804.

65. Blattman, J. N., Antia, R., Sourdive, D. J., Wang, X., Kaech, S. M., Murali-Krishna, K., Altman, J. D., and Ahmed, R. 2002. Estimating the precursor frequency of naive antigen-specific CD8 T cells. *J. Exp. Med.* 195:657.

66. Kabelitz, D., Bender, A., Schondelmaier, S., Schoel, B., and Kaufmann, S. H. E. 1990. A large fraction of human peripheral blood γ/δ+ T cells is activated by *Mycobacterium tuberculosis* but not by its 65-kD heat shock protein. *J. Exp. Med.* 171:667.

67. Davodeau, F., Peyrat, M.-A., Hallet, M.-M., Gaschet, J., Houde, I., Vivien, R., Vie, H., and Bonneville, M. 1993. Close correlation between Daudi and mycobacterial antigen recognition by human γδ T cells and expression of V9JPC1γ/V2DJCδ-encoded T cell receptors. *J. Immunol.* 151:1214.

68. De Libero, G., Casorati, G., Giachino, C., Carbonara, C., Migone, N., Matzinger, P., and Lanzavecchia, A. 1991. Selection by two powerful antigens may account for the presence of the major population of human peripheral γ/δ T cells. *J. Exp. Med.* 173:1311.

69. Parker, C. M., Groh, V., Band, H., Porcelli, S. A., Morita, C., Fabbi, M., Glass, D., Strominger, J. L., and Brenner, M. B. 1990. Evidence for extrathymic changes in the T cell receptor γ/δ repertoire. *J. Exp. Med.* 171:1597.

70. Murphy, W. J., Conlon, K. C., Sayers, T. J., Wiltrout, R. H., Back, T. C., Ortaldo, J. R., and Longo, D. L. 1993. Engraftment and activity of anti-CD3-activated human peripheral blood lymphocytes transferred into mice with severe combined immune deficiency. *J. Immunol.* 150:3634.

71. Wong, P. and Pamer, E. G. 2001. Antigen-independent CD8 T cell proliferation. *J. Immunol.* 166:5864.

72 Mercado, R., Vijh, S., Allen, S. E., Kerksiek, K., Pilip, I. M., and Pamer, E. G. 2000. Early programming of T cell populations responding to bacterial infection. *J. Immunol.* 165:6833.

73 Casetti, R., Perretta, G., Taglioni, A., Mattei, M., Colizzi, V., Dieli, F., D'Offizi, G., Malkovsky, M., and Poccia, F. 2005. Drug-induced expansion and differentiation of Vγ9Vδ2 T cells in vivo: the role of exogenous IL-2. *J. Immunol.* 175:1593.

74 Sicard, H., Ingoure, S., Luciani, B., Serraz, C., Fournié, J.-J., Bonneville, M., Tiollier, J., and Romagné, F. 2005. In vivo immunomanipulation of Vγ9Vδ2 T cells with a synthetic phosphoantigen in a preclinical nonhuman primate model. *J. Immunol.* 175:5471.

75 Wilhelm, M., Kunzmann, V., Eckstein, S., Reimer, P., Weissinger, F., Ruediger, T., and Tony, H.-P. 2003. γδ T cells for immune therapy of patients with lymphoid malignancies. *Blood* 102:200.

76 De Rosa, S. C., Andrus, J. P., Perfetto, S. P., Mantovani, J. J., Herzenberg, L. A., and Roederer, M. 2004. Ontogeny of γδ T cells in humans. *J. Immunol.* 172:1637.

77 Lopes-Carvalho, T. and Kearney, J. F. 2004. Development and selection of marginal zone B cells. *Immunol. Rev.* 197:192.

78 Pillai, S., Cariappa, A., and Moran, S. T. 2005. Marginal zone B cells. *Annu. Rev. Immunol.* 23:161.

79 Kearney, J. F. 2005. Innate-like B cells. *Springer Semin. Immunopathol.* 26:377.

80 Takeda, K., Kaisho, T., and Akira, S. 2003. Toll-like receptors. *Annu. Rev. Immunol.* 21:335.

81 Leadbetter, E. A., Rifkin, I. R., Hohlbaum, A. M., Beaudette, B. C., Shlomchik, M. J., and Marshak-Rothstein, A. 2002. Chromatin-IgG complexes activate B cells by dual engagement of IgM and Toll-like receptors. *Nature* 416:603.

82 Deetz, C. O., Hebbeler, A. M., Propp, N. A., Cairo, C., Tikhonov, I., and Pauza, C. D. 2006. Gamma interferon secretion by human Vγ2Vδ2 T cells after stimulation with antibody against the T-cell receptor plus the Toll-Like receptor 2 agonist 83 Pam$_3$Cys. *Infect. Immun.* 74:4505.

83 Rothenfusser, S., Hornung, V., Krug, A., Towarowski, A., Krieg, A. M., Endres, S., and Hartmann, G. 2001. Distinct CpG oligonucleotide sequences activate human γδ T cells via interferon-α/-β. *Eur. J. Immunol.* 31:3525.

84 Kunzmann, V., Kretzschmar, E., Herrmann, T., and Wilhelm, M. 2004. Polyinosinic-polycytidylic acid-mediated stimulation of human γδ T cells via CD11c dendritic cell-derived type I interferons. *Immunology* 112:369.

85 Morita, C. T., Mariuzza, R. A., and Brenner, M. B. 2000. Antigen recognition by human γδ T cells: pattern recognition by the adaptive immune system. *Springer Semin. Immunopathol.* 22:191.

86 Morita, C. T., Jin, C., Sarikonda, G., and Wang, H. 2007. Nonpeptide antigens, presentation mechanisms, and immunological memory of human Vγ2Vδ2 T cells: discriminating friend from foe through the recognition of prenyl pyrophosphate antigens. *Immunol. Rev.* 215:59.

87 Havlir, D. V., Ellner, J. J., Chervenak, K. A., and Boom, W. H. 1991. Selective expansion of human γδ T cells by monocytes infected with live *Mycobacterium tuberculosis*. *J. Clin. Invest.* 87:729.

88 Worku, S. and Hoft, D. F. 2003. Differential effects of control and antigen-specific T cells on intracellular mycobacterial growth. *Infect. Immun.* 71:1763.

89 Boom, W. H., Chervenak, K. A., Mincek, M. A., and Ellner, J. J. 1992. Role of the mononuclear phagocyte as an antigen-presenting cell for human γδ T cells activated by live *Mycobacterium tuberculosis*. *Infect. Immun.* 60:3480.

90 Spada, F. M., Grant, E. P., Peters, P. J., Sugita, M., Melián, A., Leslie, D. S., Lee, H. K., van Donselaar, E., Hanson, D. A., Krensky, A. M., Majdic, O., Porcelli, S. A., Morita, C. T., and Brenner, M. B. 2000. Self recognition of CD1 by γδ T cells: Implications for innate immunity. *J. Exp. Med.* 191:937.

91 Tsukaguchi, K., Balaji, K. N., and Boom, W. H. 1995. CD4$^+$ αβ T cell and γδ T cell responses to *Mycobacterium tuberculosis*. Similarities and differences in Ag recognition, cytotoxic effector function, and cytokine production. *J. Immunol.* 154:1786.

92 Ottones, F., Dornand, J., Naroeni, A., Liautard, J. P., and Favero, J. 2000. Vγ9Vδ2 T cells impair intracellular multiplication of *Brucella suis* in autologous monocytes through soluble factor release and contact-dependent cytotoxic effect. *J. Immunol.* 165:7133.

93 Dieli, F., Troye-Blomberg, M., Ivanyi, J., Fournié, J.-J., Bonneville, M., Peyrat, M. A., Sireci, G., and Salerno, A. 2000. Vγ91Vδ2 T lymphocytes reduce the viability of intracellular *Mycobacterium tuberculosis*. *Eur. J. Immunol.* 30:1512.

94 Elloso, M. M., van der Heyde, H. C., vande Waa, J. A., Manning, D. D., and Weidanz, W. P. 1994. Inhibition of *Plasmodium falciparum* in vitro by human γδ T cells. *J. Immunol.* 153:1187.

95 Dieli, F., Troye-Blomberg, M., Ivanyi, J., Fournié, J. J., Krensky, A. M., Bonneville, M., Peyrat, M. A., Caccamo, N., Sireci, G., and Salerno, A. 2001. Granulysin-dependent killing of intracellular and extracellular *Mycobacterium tuberculosis* by Vγ9/Vδ2 T lymphocytes. *J. Infect. Dis.* 184:1082.

96 Oliaro, J., Dudal, S., Liautard, J., Andrault, J. B., Liautard, J. P., and Lafont, V. 2005. Vγ9Vδ2 T cells use a combination of mechanisms to limit the spread of the pathogenic bacteria *Brucella*. *J Leukoc. Biol.* 77:652.

97 Farouk, S. E., Mincheva-Nilsson, L., Krensky, A. M., Dieli, F., and Troye-Blomberg, M. 2004. γδ T cells inhibit in vitro growth of the asexual blood stages of *Plasmodium falciparum* by a granule exocytosis-dependent cytotoxic pathway that requires granulysin. *Eur. J. Immunol.* 34:2248.

98 Jin, C. and Morita, C. T. 2006. Chemokine biology of NK cells and γδ T cells. In Mosser, B., Letts, G. L., and Neote, K., eds., *Chemokine Biology—Basic Research and Clinical Applications. vol. 1: Immunobiology of Chemokines*. Birkhäuser, Basel.

99 García, V. E., Sieling, P. A., Gong, J.-H., Barnes, P. F., Tanaka, Y., Bloom, B. R., Morita, C. T., and Modlin, R. L. 1997. Single cell cytokine analysis of γδ T cell responses to nonpeptide mycobacterial antigens. *J. Immunol.* 159:1328.

100 Poccia, F., Battistini, L., Cipriani, B., Mancino, G., Martini, F., Gougeon, M. L., and Colizzi, V. 1999. Phosphoantigen-reactive Vγ9Vδ2 T lymphocytes suppress in vitro human immunodeficiency virus type 1 replication by cell-released antiviral factors including CC chemokines. *J. Infect. Dis.* 180:858.

101 Cipriani, B., Borsellino, G., Poccia, F., Placido, R., Tramonti, D., Bach, S., Battistini, L., and Brosnan, C. F. 2000. Activation of C—C β-chemokines in human peripheral blood γδ T cells by isopentenyl pyrophosphate and regulation by cytokines. *Blood* 95:39.

102 Tikhonov, I., Deetz, C. O., Paca, R., Berg, S., Lukyanenko, V., Lim, J. K., and Pauza, C. D. 2006. Human Vγ2Vδ2 T cells contain cytoplasmic RANTES. *Int. Immunol.* 18:1243.

103 Dudal, S., Turriere, C., Bessoles, S., Fontes, P., Sanchez, F., Liautard, J., Liautard, J. P., and Lafont, V. 2006. Release of LL-37 by activated human Vγ9Vδ2 T cells: a microbicidal weapon against *Brucella suis*. *J. Immunol.* 177:5533.

104 Workalemahu, G., Foerster, M., Kroegel, C., and Braun, R. K. 2003. Human γδ-T lymphocytes express and synthesize connective tissue growth factor: effect of IL-15 and TGF-β1 and comparison with αβ-T lymphocytes. *J. Immunol.* 170:153.

105 Workalemahu, G., Foerster, M., and Kroegel, C. 2004. Expression and synthesis of fibroblast growth factor-9 in human γδ T-lymphocytes. Response to isopentenyl pyrophosphate and TGF-β1/IL-15. *J. Leukoc. Biol.* 75:657.

106 Workalemahu, G., Foerster, M., and Kroegel, C. 2006. Expression of metalloproteinase-7 (matrilysin) in human blood and bronchoalveolar gamma/delta T-lymphocytes. Selective upregulation by the soluble non-peptidic mycobacterial phosphoantigen (isopentenyl pyrophosphate). *J. Cell Physiol.* 207:67.

107 Ziegler, H. K. 2004. The role of γ/δ T cells in immunity to infection and regulation of inflammation. *Immunol Res.* 29:293.

108 Pennington, D. J., Vermijlen, D., Wise, E. L., Clarke, S. L., Tigelaar, R. E., and Hayday, A. C. 2005. The integration of conventional and unconventional T cells that characterizes cell-mediated responses. *Adv. Immunol.* 87:27.

109 Gober, H. J., Kistowska, M., Angman, L., Jeno, P., Mori, L., and De Libero, G. 2003. Human T cell receptor γδ cells recognize endogenous mevalonate metabolites in tumor cells. *J. Exp. Med.* 197:163.

110 Thompson, K. and Rogers, M. J. 2004. Statins prevent bisphosphonate-induced γδ-T-cell proliferation and activation in vitro. *J. Bone Miner. Res.* 19:278.

111 Thompson, K., Rojas-Navea, J., and Rogers, M. J. 2006. Alkylamines cause Vγ9Vδ2 T-cell activation and proliferation by inhibiting the mevalonate pathway. *Blood* 107:651.

112 Liu, Z., Guo, B. L., Gehrs, B. C., Nan, L., and Lopez, R. D. 2005. Ex vivo expanded human Vγ2Vδ2+ γδ-T cells mediate innate antitumor activity against human prostate cancer cells in vitro. *J. Urol.* 173:1552.

113 Zheng, B. J., Chan, K. W., Im, S., Chua, D., Sham, J. S., Tin, P. C., He, Z. M., and Ng, M. H. 2001. Anti-tumor effects of human peripheral γδ T cells in a mouse tumor model. *Int. J. Cancer* 92:421.

114 Choudhary, A., Davodeau, F., Moreau, A., Peyrat, M.-A., Bonneville, M., and Jotereau, F. 1995. Selective lysis of autologous tumor cells by recurrent γδ tumor-infiltrating lymphocytes from renal carcinoma. *J. Immunol.* 154:3932.

115 Viey, E., Fromont, G., Escudier, B., Morel, Y., Da Rocha, S., Chouaib, S., and Caignard, A. 2005. Phosphostim-activated γδ T cells kill autologous metastatic renal cell carcinoma. *J. Immunol.* 174:1338.

116 Corvaisier, M., Moreau-Aubry, A., Diez, E., Bennouna, J., Mosnier, J. F., Scotet, E., Bonneville, M., and Jotereau, F. 2005. Vγ2Vδ2 T cell response to colon carcinoma cells. *J. Immunol.* 175:5481.

We claim:

1. An immunogenic composition comprising: (a) an effective amount of a recombinant attenuated microbe for activating, expanding, or stimulating γδ T cells in a subject, wherein the microbe comprises a mutation in lytB and the microbe comprises one or more heterologous genes for production of mevalonate; and (b) an excipient.

2. The composition of claim 1, wherein the microbe is a bacteria.

3. The composition of claim 2, wherein the bacteria is a *Salmonella* spp.

4. The composition of claim 3, wherein the *Salmonella* spp. is *Salmonella enterica* serovar *Typhimurium* or *Typhi*.

5. The composition of claim 1, wherein the microbe is a protozoa.

6. The composition of claim 1, wherein the mutation results in a mutant lytB polypeptide having enzymatic activity reduced at least about 50% as compared to wild type lytB polypeptide.

7. The composition of claim 1, wherein the mutation results in a mutant lytB polypeptide having enzymatic activity reduced at least about 90% as compared to wild type lytB polypeptide.

8. The composition of claim 1, wherein the mutation is a deletion.

9. The composition of claim 1, wherein the mutation is an insertion.

10. The composition of claim 9, wherein the insertion is a gene for antibiotic resistance.

11. The composition of claim 1, wherein the one or more heterologous genes for production of mevalonate are selected from the group consisting of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

12. The composition of claim 11, wherein the microbe comprises heterologous genes for production of mevalonate including each of 3-hydroxy-3-methyl-glutaryl-coenzyme A (HMG-CoA) synthase, HMG-CoA reductase, isopentenyl diphosphate isomerase, isopentenyl diphosphate isomerase, mevalonate kinase, 5-phospho-mevalonate kinase, and phosphomevalonate decarboxylase.

13. The composition of claim 1, wherein the recombinant attenuated microbe having the mutation in the lytB gene produces an elevated amount of (E)-4-hydroxy-3-methyl-but-enyl-pyrophosphate (HMBPP) relative to a microbe having a wild type lytB gene.

14. The composition of claim 1, wherein the recombinant attenuated microbe having the mutation in the lytB gene accumulates HMBPP.

15. The composition of claim 1, further comprising one or more additional agents for activating, expanding, or stimulating γδ T cells.

16. The composition of claim 15, wherein the additional agent is selected from a group consisting of pyrophosphate compounds, bisphosphonates, and alkylamines.

17. The composition of claim 1, wherein the γδ T cells are human Vγ2Vδ2 T cells.

18. A recombinant attenuated *Salmonella* spp. bacteria, wherein the bacteria comprises a mutation in lytB and the bacteria comprises one or more heterologous genes for production of mevalonate.

19. The bacteria of claim 18, wherein the Salmonella spp. bacteria is *Salmonella enterica* serovar *Typhimurium* or *Typhi*.

20. The bacteria of claim 18, wherein the mutation results in a mutant lytB polypeptide having enzymatic activity reduced at least about 50% as compared to wild type lytB polypeptide.

21. The bacteria of claim 18, wherein the mutation results in a mutant lytB polypeptide having enzymatic activity reduced at least about 90% as compared to wild type lytB polypeptide.

22. The bacteria of claim 18, wherein the mutation is a deletion.

23. The bacteria of claim 18, wherein the mutation is an insertion.

24. The bacteria of claim 23, wherein the insertion is a gene for antibiotic resistance.

25. The bacteria of claim 18, wherein the one or more heterologous genes for production of mevalonate are selected from the group consisting of 3-hydroxy-3-methyl-glutaryl-coenzyme A (HMG-CoA) synthase, HMG-CoA reductase, isopentenyl diphosphate isomerase, mevalonate kinase, 5-phospho-mevalonate kinase, and phosphomevalonate decarboxylase.

26. The bacteria of claim 25, wherein the microbe comprises heterologous genes for production of mevalonate including each of 3-hydroxy-3-methyl-glutaryl- coenzyme A (HMG-CoA) synthase, HMG-CoA reductase, isopentenyl diphosphate isomerase, mevalonate kinase, 5-phospho-mevalonate kinase, and phosphomevalonate decarboxylase.

* * * * *